(12) United States Patent
David et al.

(10) Patent No.: US 7,569,079 B2
(45) Date of Patent: Aug. 4, 2009

(54) POLYCATIONIC MONOCHROMOPHORIC HYDRAZONE COMPOUNDS, DYE COMPOSITIONS COMPRISING SUCH POLYCATIONIC COMPOUNDS AND DYEING PROCESS USING THEM

(75) Inventors: Hervé David, la Varenne Saint Hilaire (FR); Nadège Murguet, Palaiseau (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/081,288

(22) Filed: Apr. 14, 2008

(65) Prior Publication Data

US 2008/0263785 A1    Oct. 30, 2008

Related U.S. Application Data

(60) Provisional application No. 60/924,035, filed on Apr. 27, 2007.

(30) Foreign Application Priority Data

Apr. 13, 2007    (FR) .................................. 07 54454

(51) Int. Cl.
*A61Q 5/10* (2006.01)
*C07D 211/02* (2006.01)
*C07D 233/00* (2006.01)

(52) U.S. Cl. ...................... 8/405; 8/406; 8/408; 8/410; 8/435; 8/568; 8/570; 8/574; 546/249; 548/300.1; 548/400

(58) Field of Classification Search ...................... 8/405, 8/406, 408, 410, 435, 568, 570, 574; 546/249; 548/300.1, 400
See application file for complete search history.

(56) References Cited

U.S. PATENT DOCUMENTS

| | | | |
|---|---|---|---|
| 6,648,924 | B2 | 11/2003 | Miyabe et al. |
| 7,288,121 | B2 | 10/2007 | Greaves et al. |
| 7,410,506 | B2 | 8/2008 | David et al. |
| 2003/0208856 | A1 | 11/2003 | Miyabe et al. |
| 2006/0096043 | A1* | 5/2006 | David et al. ................ 8/409 |
| 2007/0125261 | A1 | 6/2007 | Daubresse et al. |

FOREIGN PATENT DOCUMENTS

| | | |
|---|---|---|
| EP | 1 647 548 | 4/2006 |
| EP | 1 757 660 | 2/2007 |
| WO | WO 2007/122340 | 11/2007 |

OTHER PUBLICATIONS

STIC Search Report dated Sep. 10, 2008.*
English Language Derwent Abstract of non-English language document WO 2007/122340. (2007).
French Search Report for French Application No. 0754454 (French priority application for the present application) dated Dec. 4, 2007, Examiner A. Gregoire.

* cited by examiner

*Primary Examiner*—Eisa B Elhilo
(74) *Attorney, Agent, or Firm*—Finnegan, Henderson, Farabow, Garrett & Dunner LLP

(57) ABSTRACT

The present disclosure relates to polycationic monochromophoric hydrazone compounds of following formula (I):

$$R_1 \underset{(R_2)_m}{\overset{X}{\diagdown}} \overset{X}{\underset{N}{\diagdown}} \underset{R_5}{\overset{N^a}{\diagdown}} \underset{R_6}{\overset{}{\diagdown}} W_1 \overset{d}{\text{—}} Z \text{ An}$$

wherein $W_1$ is a heteroaromatic radical comprising 5 or 6 ring members, optionally condensed with an aromatic ring comprising 6 ring members, comprising a quaternized nitrogen atom and optionally another heteroatom which may or may not be identical to nitrogen; X, which may or may not be identical, is a nitrogen atom or a $CR_2$ group; Z is a cationic group comprising at least one quaternized nitrogen atom. 1The present disclosure also relates to a composition for dyeing human keratin fibers comprising the polycationic compounds disclosed herein, and to a dyeing process using the composition of the present disclosure, and ever further to multicompartment device.

21 Claims, No Drawings

POLYCATIONIC MONOCHROMOPHORIC HYDRAZONE COMPOUNDS, DYE COMPOSITIONS COMPRISING SUCH POLYCATIONIC COMPOUNDS AND DYEING PROCESS USING THEM

CROSS-REFERENCE TO RELATED APPLICATIONS

This application claims benefit of U.S. Provisional Application No. 60/924,035, filed Apr. 27, 2007, the contents of which are incorporated herein by reference. This application also claims benefit of priority under 35 U.S.C. § 119 to French Patent Application No. FR 07 54454, filed Apr. 13, 2007, the contents of which are also incorporated herein by reference.

FIELD OF THE INVENTION

The present application relates to polycationic monochromophoric hydrazone compounds, and to compositions for dyeing human keratin fibers comprising such compounds. It also relates to a dyeing process involving such compositions and also to multicompartment devices.

BACKGROUND OF THE INVENTION

It is known practice to dye keratin fibers, for instance human keratin fibers such as the hair, with dye compositions comprising direct dyes. These compounds are colored and coloring molecules that have a certain affinity for the fibers. It is, for example, known practice to use direct dyes of nitrobenzene, anthraquinone, nitropyridine, azo, xanthene, acridine, azine or triarylmethane type or else aromatic direct dyes comprising a hydrazone function.

Unlike the colorings obtained using oxidation dye precursors which develop the color actually within the fiber, by means of a condensation process in an alkaline oxidizing medium, direct dyes do not penetrate deeply into the keratin fiber, but remain located rather at the surface or in the fiber close to the surface.

Thus, the colorings that result from the use of direct dyes are temporary or semi-permanent colorings since the nature of the interactions which bond the direct dyes to the keratin fiber, and their desorption from the surface and/or from the core of the fiber, are responsible for their poor relative fastness with respect to repeated shampooing, for example. Moreover, these dye-fiber interactions may cause difficulties during use, for instance with regard to the uptake of the dye in the fiber, which can result in insufficiently homogeneous colorings and/or in changes in coloring.

SUMMARY OF THE INVENTION

It has been discovered that it is possible, surprisingly, to increase the affinity of cationic, monochromophoric hydrazone dyes and also their fastness with respect to light or shampooing, even on sensitized hair, by substituting them with at least one cationic group.

DETAILED DESCRIPTION OF THE INVENTION

Thus, the present disclosure relates to polycationic, monochromophoric hydrazone compounds of the following formula (I), tautomeric forms thereof and also acid-addition salts thereof and solvates thereof:

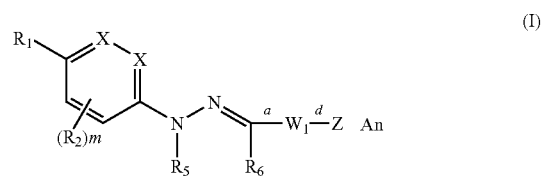

wherein:

$W_1$ is a heteroaromatic radical of following formulae (1) to (8):

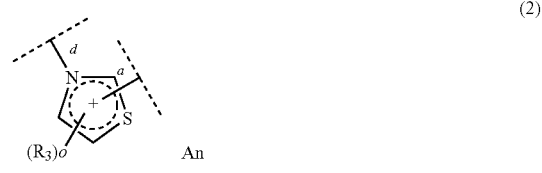

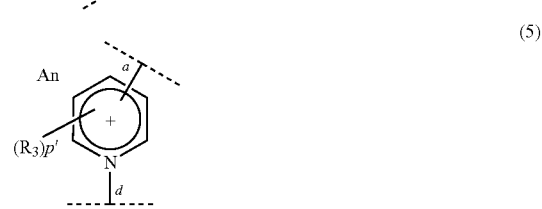

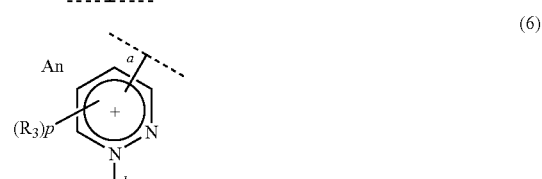

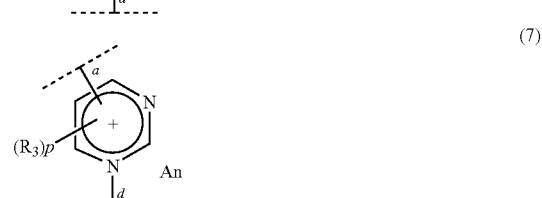

-continued

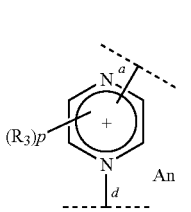

(8)

wherein:
the radical $R_1$ is chosen from:
a hydrogen;
an optionally substituted $C_1$-$C_{20}$ alkyl radical, optionally interrupted with at least one heteroatom and/or with at least one group comprising at least one heteroatom, for example, those chosen from oxygen, nitrogen, sulphur, CO, SO and $SO_2$, and combinations thereof; wherein the alkyl radical does not comprise any nitro, nitroso, peroxo or diazo function;
an alkylcarbonyl radical (R—CO—) in which R is a $C_1$-$C_4$ alkyl radical;
an alkylsulphonyl radical ($RSO_2$—) in which R is a $C_1$-$C_4$ alkyl radical;
an arylsulphonyl radical ($R'SO_2$—) in which R' is an optionally substituted phenyl or benzyl radical;
a (di)(alkyl)aminosulphonyl radical (($R)_2$N—$SO_2$—) in which the R radicals independently are chosen from a hydrogen and a $C_1$-$C_4$ alkyl radical;
a (di)(alkyl)aminocarbonyl radical (($R)_2$N—CO) in which the R radicals independently are chosen from a hydrogen and a $C_1$-$C_4$ alkyl radical;
a halogen atom such as those chosen from bromine, chlorine or fluorine;
a hydroxyl group;
a $C_1$-$C_4$ alkoxy group;
a $C_2$-$C_4$ (poly)hydroxyalkoxy group;
a hydroxycarbonyl group;
an alkoxycarbonyl group (RO—CO—) wherein R is a $C_1$-$C_4$ alkyl radical;
an alkylcarbonyloxy radical (RCO—O—) wherein R is a $C_1$-$C_4$ alkyl radical;
an optionally substituted aryloxy group;
an $NR_7R_8$ group wherein $R_7$ and $R_8$ are chosen, independently of one another, from:
a hydrogen atom;
a $C_1$-$C_4$ alkyl radical, optionally carrying at least one hydroxyl or $C_1$-$C_2$ alkoxy group, it being possible for said alkyl radicals to optionally form, with the nitrogen atom to which they are attached, a saturated or unsaturated, optionally substituted, optionally aromatic heterocycle containing from 5 to 7 ring members, optionally comprising another heteroatom which may be identical to or different from nitrogen;
a phenyl radical; an aminophenyl radical; a 4-N,N-diethylaminophenyl radical; a methoxyphenyl radical;
an alkylcarbonylamino group (RCO—NR'—) wherein the R radical is a $C_1$-$C_4$ alkyl radical and the R' radical is chosen from a hydrogen atom and a $C_1$-$C_4$ alkyl radical;
a ureido group (N($R)_2$—CO—NR'—) wherein the R and R' radicals, independently of one another, are chosen from hydrogen and $C_1$-$C_4$ alkyl radicals;

an alkylthio group (R—S—) wherein the R group is a $C_1$-$C_4$ alkyl radical;
an alkylsulphonylamino group ($RSO_2$—NR'—) wherein the R' radical is chosen from a hydrogen atom and a $C_1$-$C_4$ alkyl radical, and the R radical is a $C_1$-$C_4$ alkyl radical;
a cyano group; and
a trifluoromethyl group ($CF_3$);
The radicals $R_2$ and $R_3$, which may be identical or different, are chosen, independently of one another, from:
a halogen atom;
an optionally substituted $C_1$-$C_{16}$ alkyl radical, optionally interrupted with at least one heteroatom and/or with at least one group comprising at least one heteroatom chosen, for instance, from oxygen, nitrogen, sulphur, CO, SO and $SO_2$, and combinations thereof; wherein the alkyl radical does not comprise any nitro, nitroso, peroxo or diazo functions;
a hydroxyl radical;
a $C_1$-$C_4$ alkoxy radical;
a $C_2$-$C_4$ (poly)hydroxyalkoxy group;
a hydroxycarbonyl radical;
an alkoxycarbonyl radical (RO—CO—) wherein R is a $C_1$-$C_4$ alkyl radical;
an alkylcarbonyloxy radical (RCO—O) wherein R is a $C_1$-$C_4$ alkyl radical;
an optionally substituted aryloxy radical;
an optionally substituted arylamino radical;
an amino radical optionally substituted with one or two $C_1$-$C_4$ alkyl radicals, which may be identical or different, optionally carrying at least one hydroxyl or $C_1$-$C_2$ alkoxy group, it being possible for said alkyl radicals to optionally form, with the nitrogen atom to which they are attached, a saturated or unsaturated, optionally substituted, optionally aromatic heterocycle containing from 5 to 7 ring members, optionally comprising another heteroatom which may be identical to or different from nitrogen;
an alkylcarbonylamino radical (RCO—NR'—) wherein the R radical is a $C_1$-$C_4$ alkyl radical and the R' radical is chosen from a hydrogen and a $C_1$-$C_4$ alkyl radical;
a (di)(alkyl)aminocarbonyl group (($R)_2$N—CO—) wherein the R radicals, independently of one another, are chosen from a hydrogen and a $C_1$-$C_4$ alkyl radical;
a ureido radical (N($R)_2$—CO—NR'—) wherein the R radicals, independently of one another, are chosen from $C_1$-$C_4$ alkyl radicals, and R' is chosen from a hydrogen and a $C_1$-$C_4$ alkyl radical;
a (di)(alkyl)aminosulphonyl radical (($R)_2$N—$SO_2$—) wherein the R radical is chosen from a hydrogen atom and a $C_1$-$C_4$ alkyl radical;
an alkylthio radical (R—S—) wherein the R radical is a $C_1$-$C_4$ alkyl radical;
an alkylsulphonylamino radical ($RSO_2$—NR'—) wherein the R radical is a $C_1$-$C_4$ alkyl radical, and the R' radical is chosen from a hydrogen atom and a $C_1$-$C_4$ alkyl radical;
an alkylsulphonyl radical ($RSO_2$—) wherein the R radical is a $C_1$-$C_4$ alkyl radical;
a cyano radical (—CN); and
a trifluoromethyl radical ($CF_3$);
Two adjacent radicals $R_2$ can form, with one another and with the carbon atoms to which they are attached, a substituted or unsubstituted, aromatic or nonaromatic (hetero)cyclic radical comprising 5 or 6 ring members;
One of the radicals $R_7$ or $R_8$ can form, with the nitrogen atom to which it is attached and with a radical $R_2$ located in the ortho-position with respect to the $NR_7R_8$ group, a substituted or unsubstituted, saturated or unsaturated heterocycle comprising 5 or 6 ring members;

The radicals $R_7$ and $R_8$ can form, with the nitrogen atom to which they are attached and each with a radical $R_2$ located in the ortho-position with respect to the $NR_7R_8$ group, a substituted or unsubstituted, saturated or unsaturated heterocycle comprising 5 or 6 ring members;

m is an integer ranging from 0 to 4; when m is less than 4, the unsubstituted carbon atom(s) carries (carry) a hydrogen atom;

X, independently of one another, is chosen from N and $CR_2$;

o is an integer ranging from 0 to 2; when o is less than 2, the unsubstituted carbon atom(s) carries (carry) a hydrogen atom;

Two adjacent radicals $R_3$ can form, with one another and with the carbon atoms to which they are attached, a substituted or unsubstituted aromatic ring comprising 6 ring members;

The radicals $R_4$, which may be identical or different, are chosen from:
  an optionally substituted $C_1$-$C_{20}$ alkyl radical, optionally interrupted with at least one heteroatom and/or with at least one group comprising at least one heteroatom, for instance, chosen from oxygen, sulphur, CO, SO and $SO_2$, and combinations thereof; wherein the alkyl radical does not comprise any nitro, nitroso, peroxo or diazo function;
  a $C_1$-$C_4$ trimethylsilylalkyl radical;
  an optionally substituted phenyl radical;
  an optionally substituted benzyl radical;

The radical $R_5$ is chosen from:
  a hydrogen;
  an optionally substituted $C_1$-$C_{20}$ alkyl radical, optionally interrupted with at least one heteroatom and/or with at least one group comprising at least one heteroatom, for example, chosen from oxygen, nitrogen, sulphur, CO, SO and $SO_2$, and combinations thereof; wherein the alkyl radical does not comprise any nitro, nitroso, peroxo or diazo function;
  an optionally substituted phenyl radical;
  an optionally substituted benzyl radical;
  an alkylcarbonyl radical (R—CO—) wherein R is a $C_1$-$C_4$ alkyl radical;
  an alkylsulphonyl radical ($RSO_2$—) wherein R is a $C_1$-$C_4$ alkyl radical;
  an arylsulphonyl radical ($R'SO_2$—) wherein R' is an optionally substituted phenyl or benzyl radical;
  a (di)(alkyl)aminosulphonyl radical (($R)_2N$—$SO_2$—) wherein the R radicals are independently chosen from a hydrogen and a $C_1$-$C_4$ alkyl radical;
  a (di)(alkyl)aminocarbonyl radical (($R)_2N$—CO—) in which the R radicals are independently chosen from a hydrogen and a $C_1$-$C_4$ alkyl radical;

$R_5$ can form, with a radical $R_2$ located in the ortho-position with respect to the $NR_5$ group and with the nitrogen atom substituted with $R_5$, a substituted or unsubstituted, saturated or unsaturated heterocycle comprising 5 or 6 ring members;

The radical $R_6$ is chosen from:
  a hydrogen atom;
  an optionally substituted $C_1$-$C_{16}$ alkyl radical, optionally interrupted with at least one heteroatom and/or with at least one group comprising at least one heteroatom, for example, chosen from oxygen, nitrogen, sulphur, CO, SO and $SO_2$, and combinations thereof; wherein the alkyl radical does not comprise any nitro, nitroso, peroxo or diazo function;
  an amino radical optionally substituted with one or two $C_1$-$C_4$ alkyl radicals, which may be identical or different, optionally carrying at least one hydroxyl or $C_1$-$C_2$ alkoxy group, it being possible for said alkyl radicals to optionally form, with the nitrogen atom to which they are attached, an optionally substituted, saturated or unsaturated or aromatic heterocycle comprising 5 or 6 ring members, optionally comprising at least one other heteroatom which may be identical to or different from nitrogen;
  an alkylcarbonylamino radical (RCO—NR'—) wherein the R radical is a $C_1$-$C_4$ alkyl radical and the R' radical is chosen from a hydrogen and a $C_1$-$C_4$ alkyl radical;
  a ureido radical (N(R)$_2$CO—NR'—) wherein the R radicals, independently of one another, are chosen from $C_1$-$C_4$ alkyl radicals, and R' is chosen from a hydrogen and a $C_1$-$C_4$ alkyl radical;
  an alkylsulphonylamino radical ($RSO_2$—NR'—) in which the R radical is a $C_1$-$C_4$ alkyl radical and the R' radical is chosen from hydrogen and a $C_1$-$C_4$ alkyl radical;
  a hydroxycarbonyl radical (HOOC—);
  a $C_1$-$C_4$ alkoxycarbonyl radical (RO—CO—);
  an optionally substituted phenyl radical; and
  an optionally substituted benzyl radical;

p is an integer ranging from 0 to 3; p' is an integer ranging from 0 to 4; when p is less than 3, or p' is less than 4, the unsubstituted carbon atom(s) carries a hydrogen atom;

The bond a links the heteroaromatic radical $W_1$ to the carbon atom of the $CR_6$ group;

Z is a $C_2$-$C_{20}$ alkylene radical comprising at least one quaternized nitrogen atom;

the bond d links the cationic group(s) Z to a nitrogen atom of the heteroaromatic radical $W_1$;

the electroneutrality of the compounds of formula (I) being ensured by at least one cosmetically acceptable anion An or a mixture of cosmetically acceptable anions An, which may or may not be identical.

Another aspect of the present disclosure is a composition for dyeing human keratin fibers, such as the hair, comprising at least one monochromophoric hydrazone compound of formula (I) as described above.

A further aspect of the present disclosure is a process for dyeing human keratin fibers, comprising:
  applying a dye composition to the keratin fibers,
  wherein the dye composition is left to act for a period of time sufficient to obtain a desired effect.

The present disclosure also relates to a multicompartment device with a first compartment comprising a composition according to the present disclosure and a second compartment comprising a composition comprising at least one oxidizing agent.

According to at least one embodiment of the present disclosure, the device comprises a first compartment comprising a composition that comprises at least one polycationic monochromophoric dye of formula (I), a second compartment comprising at least one oxidation dye precursor chosen from at least one oxidation base optionally associated with at least one coupler, and a third compartment comprising a composition comprising at least one oxidizing agent.

As disclosed herein, the compounds comprising a hydrazone function defined above, in addition to the benefits relating to their affinity with the fiber, also may make it possible, with colors that may range up to purple, to broaden the color range conventionally achieved with such dyes.

They are also stable under lightening alkaline conditions.

Moreover, these compounds can constitute synthesis intermediates for dyes comprising several chromophores linked to one another by at least one linker arm.

However, other features and benefits of the present disclosure will emerge more clearly on reading the description and the examples presented below.

In the subsequent text, and unless otherwise indicated, the limits delimiting a range of values are included in this range.

For the purpose of the present disclosure, and unless otherwise indicated:

An alkyl radical is linear or branched.

An alkyl radical or the alkyl part of a radical is said to be "substituted" when it comprises at least one substituent chosen from the groups:
hydroxyl,
$C_1$-$C_4$ alkoxy, $C_2$-$C_4$ (poly)hydroxyalkoxy,
amino optionally substituted with at least one $C_1$-$C_4$ alkyl group, which may be identical or different, optionally carrying at least one hydroxyl group, it being possible for said alkyl radicals to form, with the nitrogen atom to which they are attached, a heterocycle comprising 5 or 6 ring members, and optionally comprising at least one other heteroatom which may or may not be different from nitrogen.

An aryl or heteroaryl radical or the aryl or heteroaryl part of a radical is said to be "substituted" when it comprises at least one substituent carried by a carbon atom, chosen from
a $C_1$-$C_{16}$, such as $C_1$-$C_8$, alkyl radical optionally substituted with at least one radical chosen from the radicals: hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally carrying at least one hydroxyl group, or it being possible for the two radicals to form, with the nitrogen atom to which they are attached, a heterocycle comprising 5 or 7 ring members, for instance 5 or 6 ring members, and optionally comprising another heteroatom which may be identical to or different from nitrogen;
a halogen atom such as chlorine, fluorine or bromine;
a hydroxyl group;
a $C_1$-$C_2$ alkoxy radical; a $C_2$-$C_4$ (poly)hydroxyalkoxy radical;
an amino radical optionally substituted with one or two $C_1$-$C_4$ alkyl radicals, which may be identical or different, optionally carrying at least one hydroxyl or amino group substituted with two optionally substituted $C_1$-$C_2$ alkyl radicals;
an alkylcarbonylamino radical (—NR—COR') in which the R radical is a hydrogen atom or a $C_1$-$C_4$ alkyl radical optionally carrying at least one hydroxyl group, and the R' radical is a $C_1$-$C_2$ alkyl radical;
a (di)(alkyl)aminocarbonyl radical (($R$)$_2$N—CO) in which the R radicals, which may be identical or different, are chosen from a hydrogen atom and a $C_1$-$C_4$ alkyl radical optionally carrying at least one hydroxyl group;
a hydroxycarbonyl radical (HOOC—);
an alkoxycarbonyl radical (RO—CO—) in which the R radical is a $C_1$-$C_4$ alkyl radical;
an alkylsulphonylamino radical (R'SO$_2$—NR—) in which the R radical is chosen from a hydrogen atom and a $C_1$-$C_4$ alkyl radical optionally carrying at least one hydroxyl group, and the R' radical is chosen from a $C_1$-$C_4$ alkyl radical and a phenyl radical;
an aminosulphonyl radical (($R$)$_2$N—SO$_2$—) in which the R radicals, which may be identical or different, are chosen from a hydrogen atom and a $C_1$-$C_4$ alkyl radical optionally carrying at least one hydroxyl group.

The cyclic or heterocyclic part of a nonaromatic radical or a (hetero)cyclic radical is said to be substituted when it comprises at least one substituent carried by a carbon atom, chosen from the groups:
hydroxyl,
$C_1$-$C_4$ alkoxy, $C_2$-$C_4$ (poly)hydroxyalkoxy,
alkylcarbonylamino (RCO—NR'—) in which the R' radical is a hydrogen atom or a $C_1$-$C_4$ alkyl radical optionally carrying at least one hydroxyl group, and the R radical is a $C_1$-$C_2$ alkyl radical or an amino radical substituted with two $C_1$-$C_4$ alkyl groups, which may be identical or different, optionally carrying at least one hydroxyl group, it being possible for said alkyl radicals to form, with the nitrogen atom to which they are attached, a heterocycle comprising 5 or 6 ring members, and optionally comprising at least one other heteroatom which may or may not be different from nitrogen.

As indicated previously, a first aspect of the present disclosure comprises compounds corresponding to abovementioned formula (I).

According to at least one embodiment of the present disclosure, the polycationic compounds are such that $W_1$ is chosen from a heteroaromatic radical of formulae below:

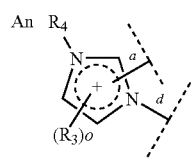

(1)

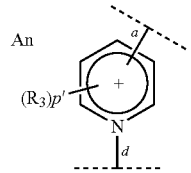

(5)

The radicals $R_3$ and $R_4$, o, p', a and d having the same meanings as indicated above.

In accordance with at least one embodiment of the present disclosure, the polycationic compounds of formula (I) are, for example, such that the radical $R_1$ is chosen from:
a hydrogen;
a $C_1$-$C_4$ alkyl radical, optionally substituted with at least one radical, which may or may not be identical, chosen from the radicals hydroxyl; $C_1$-$C_2$ alkoxy; $C_2$-$C_4$ (poly)hydroxyalkoxy; amino substituted with one or two $C_1$-$C_2$ alkyl(s) which may or may not be identical; thio (—SH); $C_1$-$C_4$ thioalkyl (—RS); ($C_1$-$C_4$)alkylsulphinyl; and ($C_1$-$C_4$)alkylsulphonyl;
an alkylcarbonyl radical (R—CO—) wherein R is a $C_1$-$C_4$ alkyl radical;
an alkylsulphonyl radical (RSO$_2$—) wherein R is chosen from a $C_1$-$C_4$ alkyl radical; an arylsulphonyl radical (R'SO$_2$—) wherein R' is an optionally substituted phenyl or benzyl radical;
a (di)(alkyl)aminosulphonyl radical (($R$)$_2$N—SO$_2$—) wherein the R radicals independently are chosen from a hydrogen and a $C_1$-$C_4$ alkyl radical;

a (di)(alkyl)aminocarbonyl radical ((R)$_2$N—CO—) wherein the R radicals independently are chosen from a hydrogen and a C$_1$-C$_4$ alkyl radical;
a chlorine atom;
a hydroxyl group;
a C$_1$-C$_4$ alkoxy group;
a C$_2$-C$_4$ hydroxyalkoxy group;
a hydroxycarbonyl group;
an alkoxycarbonyl group (RO—CO—) wherein R is a C$_1$-C$_4$ alkyl radical;
an alkylcarbonyloxy radical (RCO—O—) wherein R is a C$_1$-C$_4$ alkyl radical;
an optionally substituted aryloxy group;
an NR$_7$R$_8$ group in which R$_7$ and R$_8$ are chosen, independently of one another, from:
  a hydrogen atom;
  a C$_1$-C$_4$ alkyl radical optionally carrying at least one hydroxyl or C$_1$-C$_2$ alkoxy group, it being possible for said alkyl radicals to optionally form, with the nitrogen atom to which they are attached, a saturated or unsaturated, optionally substituted, optionally aromatic heterocycle comprising from 5 to 7 ring members, and optionally comprising another heteroatom which may be identical to or different from nitrogen;
  a phenyl radical; an aminophenyl radical; a 4-N,N-diethylaminophenyl radical; a methoxyphenyl radical;
an alkylcarbonylamino group (RCO—NR'—) wherein the R radical is a C$_1$-C$_4$ alkyl radical and the R' radical is chosen from a hydrogen atom and a C$_1$-C$_4$ alkyl radical;
an alkylsulphonylamino group (RSO$_2$—NR'—) in which the R' radical is chosen from a hydrogen atom and a C$_1$-C$_4$ alkyl radical, and the R radical is a C$_1$-C$_4$ alkyl radical.

In at least one embodiment, the radical R$_1$ is chosen from:
a hydrogen;
a C$_1$-C$_4$ alkyl radical optionally substituted with a hydroxyl or C$_1$-C$_2$ alkoxy group;
a chlorine atom;
a hydroxyl group;
a C$_1$-C$_4$ alkoxy group;
a C$_2$-C$_4$ hydroxyalkoxy group;
a hydroxycarbonyl group;
an alkoxycarbonyl group (RO—CO—) wherein R is a C$_1$-C$_2$ alkyl radical;
an unsubstituted aryloxy group;
an NR$_7$R$_8$ group in which R$_7$ and R$_8$ are chosen, independently of one another, from:
  a hydrogen atom;
  a C$_1$-C$_4$ alkyl radical optionally carrying at least one hydroxyl or C$_1$-C$_2$ alkoxy group, it being possible for said alkyl radicals to optionally form, with the nitrogen atom to which they are attached, a saturated or unsaturated, optionally substituted, optionally aromatic heterocycle comprising from 5 to 7 ring members, and optionally comprising another heteroatom which may be identical to or different from nitrogen;
  a phenyl radical; a 4-N,N-diethylaminophenyl radical; a methoxyphenyl radical;
an alkylcarbonylamino group (RCO—NR'—) wherein the R radical is a C$_1$-C$_4$ alkyl radical and the R' radical is a hydrogen atom or a C$_1$-C$_4$ alkyl radical;
an alkylsulphonylamino group (RSO$_2$—NR'—) wherein the R' radical is chosen from a hydrogen atom and a C$_1$-C$_2$ alkyl radical, and the R radical is a C$_1$-C$_2$ alkyl radical.

According to at least one further embodiment of the present disclosure, R$_1$ is chosen from a hydrogen, a chlorine, a hydroxyl, a methyl, an ethyl, a 2-hydroxyethyl radical, a 2-methoxyethyl radical, a methoxy, a hydroxycarbonyl group, a methoxycarbonyl group, an amino, (di)methylamino, (tri)ethylamino or (di)-2-hydroxyethylamino group, a pyrrolidone group, a phenylamino, 4-methoxyphenylamino, 4-aminophenylamino or 4-N,N-diethylaminophenylamino group, a methylsulphonylamino group (CH$_3$SO$_2$—NH—) and a methylcarbonylamino group (CH$_3$CONH—).

According to at least one embodiment of the present disclosure, when R$_1$ is a radical —NR$_7$R$_8$, then one of the radicals R$_7$ or R$_8$ forms, with the nitrogen atom to which it is attached and with a radical R$_2$ located in the ortho-position with respect to the NR$_7$R$_8$ group, a saturated or unsaturated, substituted or unsubstituted heterocycle comprising 5 or 6 ring members.

Thus, according to at least one embodiment, the —NR$_7$R$_8$ group, with the aromatic ring optionally substituted with a hydroxyl or methoxy, can form one of the following groups:

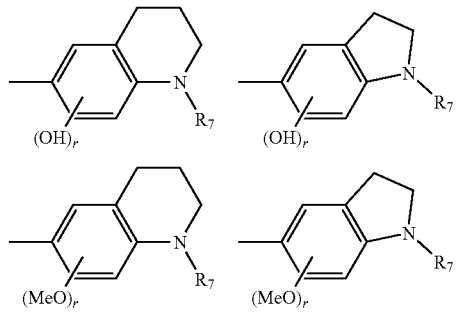

where r is 0 or 1.

According to another embodiment as disclosed herein, when R$_1$ is a radical —NR$_7$R$_8$, then the two radicals R$_7$ and R$_8$ form, with the nitrogen atom to which they are attached and each with a radical R$_2$ located in the ortho-position with respect to the —NR$_7$R$_8$ group, a saturated or unsaturated, substituted or unsubstituted heterocycle comprising 5 or 6 ring members.

For example, the —NR$_7$R$_8$ group, with the aromatic ring optionally substituted with a hydroxyl or a methoxy, can form one of the following groups:

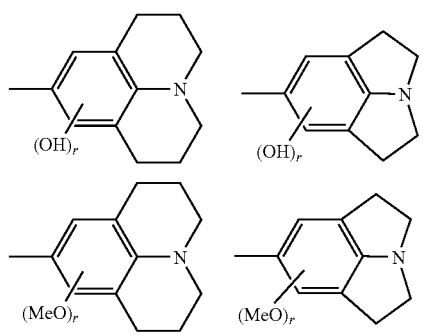

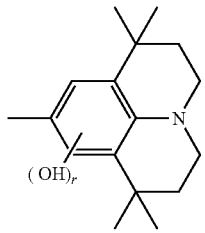

where r is 0 or 1.

With respect to radicals $R_2$ and $R_3$, the latter, independently of one another, are chosen, for example, from:
- a chlorine atom;
- a $C_1$-$C_{16}$ alkyl radical optionally substituted with at least one group, which may or may not be identical, chosen from hydroxyl, $C_1$-$C_2$ alkoxy, amino, thio, $C_1$-$C_2$ ((di)alkyl)amino, $C_1$-$C_2$ alkylsulphonylamino and $C_1$-$C_2$ alkylsulphonyl radicals;
- a hydroxyl radical;
- a $C_1$-$C_4$ alkoxy radical; a $C_2$-$C_4$ hydroxyalkoxy group;
- a hydroxycarbonyl radical;
- a ($C_1$-$C_4$)alkoxycarbonyl radical;
- a ($C_1$-$C_4$)alkylcarbonyloxy radical;
- an optionally substituted aryloxy radical;
- an amino radical optionally substituted with one or two $C_1$-$C_4$ alkyl radicals, which may be identical or different, optionally carrying at least one hydroxyl or $C_1$-$C_2$ alkoxy group, it being possible for said alkyl radicals to optionally form, with the nitrogen atom to which they are attached, a saturated or unsaturated, optionally substituted, optionally aromatic heterocycle comprising 5 or 7 ring members, and optionally comprising another heteroatom which may be identical to or different from nitrogen; or with one or two phenyl, aminophenyl, N,N-diethylaminophenyl or methoxyphenyl radicals;
- a ($C_1$-$C_4$)alkylcarbonylamino radical;
- an aminocarbonyl radical, a ($C_1$-$C_4$)(di)alkylaminocarbonyl group;
- an aminosulphonyl or ($C_1$-$C_4$)(di)alkylaminosulphonyl radical;
- a ($C_1$-$C_4$)alkylthio radical;
- a ($C_1$-$C_4$)alkylsulphonylamino radical;
- a cyano radical;
- a phenyl radical;
- a trifluoromethyl radical;
- a thio radical; and
- a ($C_1$-$C_4$)alkylsulphonyl radical.

In at least one embodiment, the radicals $R_2$ and $R_3$, independently of one another, are chosen from:
- a chlorine atom;
- a $C_1$-$C_8$ alkyl radical optionally substituted with at least one group, which may or may not be identical, chosen from hydroxyl, $C_1$-$C_2$ alkoxy, amino, thio, $C_1$-$C_2$ ((di)alkyl)amino, $C_1$-$C_2$ alkylsulphonylamino and $C_1$-$C_2$ alkylsulphonyl radicals;
- a hydroxyl radical;
- a $C_1$-$C_4$ alkoxy radical;
- a ($C_2$-$C_4$)alkoxycarbonyl radical;
- an optionally substituted aryloxy radical;
- an amino radical optionally substituted:
  with one or two $C_1$-$C_4$ alkyl radicals, which may be identical or different, optionally carrying a hydroxyl or $C_1$-$C_2$ alkoxy group, it being possible for said alkyl radicals to optionally form, with the nitrogen atom to which they are attached, a saturated or unsaturated, optionally substituted heterocycle comprising 5 or 7 ring members;
  with one or two phenyl, aminophenyl or methoxyphenyl radicals;
- a ($C_1$-$C_4$)alkylcarbonylamino radical in which the amino function is unsubstituted or substituted with a $C_1$-$C_4$ alkyl radical;
- a hydroxycarbonyl radical;
- an aminocarbonyl radical;
- an aminosulphonyl or ($C_1$-$C_4$)(di)alkylaminosulphonyl radical;
- a ($C_1$-$C_2$)alkylsulphonylamino radical;
- a ($C_1$-$C_2$)alkylsulphonyl radical;
- a ($C_1$-$C_4$)alkylthio radical;
- a phenyl radical;
- a trifluoromethyl radical; and
- a thio radical.

In at least one further embodiment, the radicals $R_2$ and $R_3$, independently of one another, are chosen from a chlorine atom; a methyl, ethyl, 2-hydroxyethyl or 2-methoxyethyl radical; a hydroxyl radical; a methoxy or ethoxy radical; a methylsulphonyl radical; a methylcarbonylamino radical ($CH_3CONH-$); a hydroxycarbonyl radical; an amino, (di)methylamino, (di)ethylamino or (di)-2-hydroxyethylamino radical; a pyrrolidino radical; a methoxycarbonyl or ethoxycarbonyl radical; a phenyl radical; a methylsulphonylamino radical ($CH_3SO_2NH-$); and a 4-methoxyphenylamino or 4-aminophenylamino radical.

According to another embodiment, two adjacent radicals $R_2$ form, with one another and with the carbon atoms to which they are attached, an optionally aromatic, substituted or unsubstituted cyclic radical comprising 5 or 6 ring members. According to one embodiment, the aromatic group formed in the context of this embodiment is an unsubstituted phenyl ring.

According to another embodiment of the present disclosure, two adjacent radicals $R_3$ form, with one another and with the carbon atoms to which they are attached, a substituted or unsubstituted aromatic ring with 6 ring members. For instance, the aromatic group formed in the context of this embodiment is an unsubstituted phenyl ring.

With respect to radical $R_4$, it can be chosen from, for instance:
- a $C_1$-$C_8$, for instance a $C_1$-$C_8$, alkyl radical optionally substituted with a radical chosen from hydroxyl, $C_1$-$C_4$ alkoxy, amino optionally substituted with one or two $C_1$-$C_2$ alkyl radicals;
- a $C_1$-$C_4$ trimethylsilylalkyl radical;
- a phenyl radical optionally substituted with one or two groups chosen from chlorine, a hydroxyl radical, and an amino radical; and
- a benzyl radical optionally substituted with one or two groups chosen from chlorine, a hydroxyl radical, and an amino radical.

In at least one embodiment, the radical $R_4$ may be chosen from methyl, ethyl, propyl, butyl, pentyl, hexyl, heptyl, octyl, 2-hydroxyethyl, 3-methoxypropyl, 4-chlorophenyl, phenyl, benzyl and 3,4-dihydroxybenzyl radicals.

With respect to radical $R_5$, it can be chosen from, for example:
- a hydrogen;
- a $C_1$-$C_6$ alkyl radical optionally substituted with at least one hydroxyl group, with at least one $C_1$-$C_2$ alkoxy group or with at least one hydroxycarbonyl group;

a phenyl radical optionally substituted with at least one halogen atom, such as chlorine, bromine, iodine or fluorine; or with at least one hydroxyl and/or amino group;

a benzyl radical optionally substituted with at least one hydroxyl and/or amino groups;

a ($C_1$-$C_4$)alkylcarbonyl radical; and a ($C_1$-$C_4$)alkylsulphonyl radical.

According to another embodiment, the radical $R_5$ is chosen from a hydrogen atom, a methyl radical, an ethyl radical, a 2-hydroxyethyl radical, a 2-methoxyethyl radical, an acetyl radical ($CH_3CO—$), a methylsulphonyl radical ($CH_3SO_2—$), a phenyl radical, a benzyl radical optionally substituted with at least one hydroxyl or amino and a combination thereof.

According to at least one embodiment of the present disclosure, $R_5$ is chosen from a hydrogen atom; a methyl radical; a 2-hydroxyethyl radical; a $CH_3CO—$ radical; a $CH_3SO_2$- radical; and an unsubstituted benzyl radical.

$R_5$ can also form, with a radical $R_2$ located in the ortho-position with respect to the $R_5$ group and with the nitrogen atom substituted with $R_5$, a saturated or unsaturated heterocycle comprising 5 or 6 ring members, which is unsubstituted or substituted, for example, unsubstituted or substituted with a methyl radical.

In formula (I), the radical $R_6$ is chosen from, for example:

a hydrogen atom;

a $C_1$-$C_4$ alkyl radical optionally substituted with at least one radical chosen from hydroxyl, $C_1$-$C_2$ alkoxy, $C_2$-$C_4$ (poly)hydroxyalkoxy, amino $C_1$-$C_2$ (di)alkylamino, thio (—SH), ($C_1$-$C_4$)alkylsulphinyl, ($C_1$-$C_4$)alkylsulphonyl and ($C_1$-$C_4$)thioalkyl radicals; such as, a $C_1$-$C_4$ alkyl radical optionally substituted with a hydroxyl radical;

an amino group optionally substituted with at least one $C_1$-$C_4$ alkyl radical, which may be identical or different, optionally carrying at least one hydroxyl group;

an alkylcarbonylamino group (RCO—NR—) wherein the R radicals are chosen from, independently of one another, $C_1$-$C_4$ alkyl radicals;

an alkylsulphonylamino group ($RSO_2$—NR'—) wherein the R and R' radicals are chosen from, independently of one another, a hydrogen atom and a $C_1$-$C_4$ alkyl radical;

a hydroxycarbonyl radical (—COOH);

a $C_1$-$C_2$ alkoxycarbonyl radical;

a phenyl radical optionally substituted with at least one radical chosen from hydroxyl, $C_1$-$C_2$ alkoxy, $C_2$-$C_4$ (poly)hydroxyalkoxy, amino and $C_1$-$C_2$ (di)alkylamino radicals; for instance, a phenyl radical optionally substituted with a radical chosen from hydroxyl and amino radicals, or a combination thereof; and a benzyl radical optionally substituted with at least one radical chosen from hydroxyl, $C_1$-$C_2$ alkoxy, $C_2$-$C_4$ (poly)hydroxyalkoxy, amino and $C_1$-$C_2$ (di)alkylamino radicals; for example, a benzyl radical optionally substituted with a radical chosen from hydroxyl and amino radicals, or a combination thereof.

In a still further embodiment, the radical $R_6$ is chosen from:

a hydrogen;

a methyl, ethyl or 2-hydroxyethyl radical;

an amino radical;

a hydroxycarbonyl radical;

a methoxycarbonyl radical;

a methylcarbonylamino group ($CH_3CO$—NH—);

a methylsulphonylamino group ($CH_3SO_2$—NH—);

a phenyl radical optionally substituted with a hydroxyl and/or amino group or a combination thereof; and a benzyl radical optionally substituted with a hydroxyl and/or amino group or a combination thereof.

According to at least one embodiment, $R_6$ is a hydrogen atom.

The polycationic compounds according to the present disclosure can be, in at least one embodiment, chosen from the compounds in which Z is a $C_2$-$C_{20}$ alkylene radical:

1—Interrupted with at least one group, which may or may not be identical, corresponding to the following formulae:

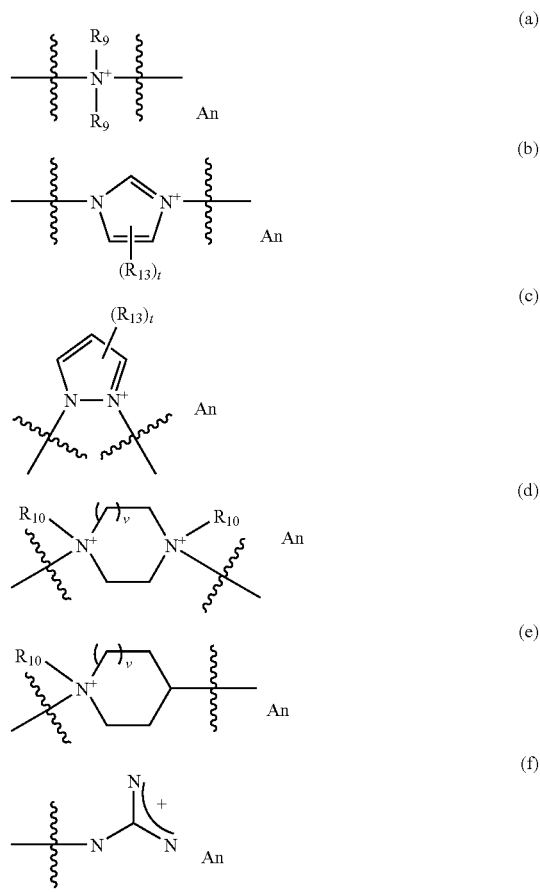

wherein:

$R_9$ and $R_{10}$, independently of one another, are chosen from a $C_1$-$C_8$ alkyl radical; a $C_1$-$C_6$ monohydroxyalkyl radical; a $C_2$-$C_6$ polyhydroxyalkyl radical; a ($C_1$-$C_6$)alkoxy ($C_1$-$C_6$)alkyl radical; an aryl radical such as phenyl which is optionally substituted; an arylalkyl radical such as benzyl which is optionally substituted; a $C_1$-$C_6$ aminoalkyl radical in which the amine is substituted with one or two $C_1$-$C_4$ alkyl radicals which may be identical or different; a ($C_1$-$C_6$)alkylsulphonyl radical;

two radicals $R_9$ can form, together with the nitrogen atom to which they are attached, a saturated or unsaturated, optionally substituted ring comprising 5, 6 or 7 ring members;

$R_{13}$, which may be identical or different, is chosen from a hydrogen atom, a halogen atom chosen from bromine, chlorine or fluorine, a $C_1$-$C_6$ alkyl radical, a $C_1$-$C_6$ monohydroxyalkyl radical, a $C_2$-$C_6$ polyhydroxyalkyl radical, a $C_1$-$C_6$ alkoxy radical, a $C_1$-$C_4$ (di)alkylamino radical, a hydroxycarbonyl radical, a $C_1$-$C_6$ alkylcarbonyl radical, a $C_1$-$C_6$ thioalkyl radical, a ($C_1$-$C_6$)alkylthio radical, a ($C_1$-$C_6$)alkylsulphonyl radical, a benzyl radical which is optionally substituted, and a phenyl radical which is optionally substituted with at least one radical chosen from methyl, hydroxyl, amino and methoxy radicals;

An is an organic or inorganic anion or a mixture of organic or inorganic anions;

t is an integer ranging from 0 to 3; if t<3, then the unsubstituted carbon atoms carry a hydrogen atom;

v is an integer equal to 1 or 2, and according to at least one embodiment is equal to 1;

2—and optionally interrupted with at least one heteroatom or group comprising at least one heteroatom or combinations thereof, such as, for example, oxygen, nitrogen, sulphur, a —CO— group, an —SO$_2$— group; on the condition that there is no azo, nitro, nitroso or peroxo group or bond in the group Z;

3—and optionally substituted with at least one radical chosen from the radicals: hydroxyl, $C_1$-$C_2$ alkoxy, $C_2$-$C_4$ (poly)hydroxyalkoxy, amino substituted with one or two $C_1$-$C_2$ linear alkyl groups optionally carrying at least one hydroxyl, ($C_1$-$C_4$)trialkylsilyl or imidazole group.

According to at least one embodiment, Z is a $C_2$-$C_{20}$ alkylene radical:

1—interrupted with one or two groups, which may or may not be identical, corresponding to the following formulae:

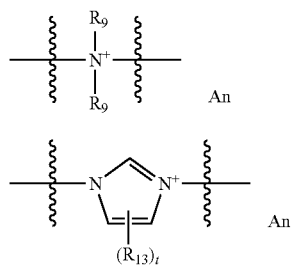

wherein:
$R_9$, independently of one another, is chosen from a $C_1$-$C_8$ alkyl radical; a $C_1$-$C_6$ monohydroxyalkyl radical; a ($C_1$-$C_6$)alkoxy($C_1$-$C_6$)alkyl radical; a phenyl radical, and a benzyl radical;

two radicals $R_9$ can form, together with the nitrogen atom to which they are attached, a saturated or unsaturated, optionally substituted ring comprising 5 or 6 ring members;

$R_{13}$, which may be identical or different, is chosen from a hydrogen atom, a $C_1$-$C_6$ alkyl radical, a $C_1$-$C_6$ monohydroxyalkyl radical, a $C_1$-$C_6$ alkoxy radical and a $C_1$-$C_4$ (di)alkylamino radical;

An is a cosmetically acceptable organic or inorganic anion or a mixture of cosmetically acceptable organic or inorganic anions;

t is an integer ranging from 0 to 3; if t<3, then the unsubstituted carbon atoms carry a hydrogen atom; and v is an integer equal to 1 or 2, and according to at least one embodiment is 1;

2—and optionally substituted with a radical chosen from the radicals: hydroxyl, $C_1$-$C_2$ alkoxy, $C_2$-$C_4$ hydroxyalkoxy, amino substituted with one or two $C_1$-$C_2$ linear alkyl groups optionally carrying a hydroxyl, ($C_1$-$C_3$)trialkylsilyl or imidazole group.

According to at least one embodiment, the polycationic compounds according to the present disclosure are such that X is $CR_2$, the radicals $R_2$, which may or may not be identical, being defined as above.

For instance, in at least one further embodiment, the polycationic compounds according to the present disclosure correspond to the following formulae: the tautomeric forms thereof and also the acid-addition salts thereof and the solvates thereof:

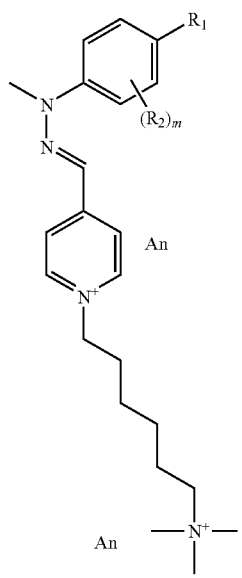

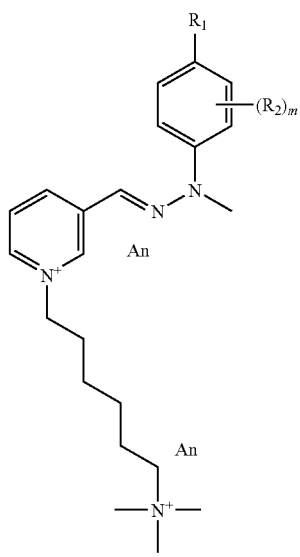

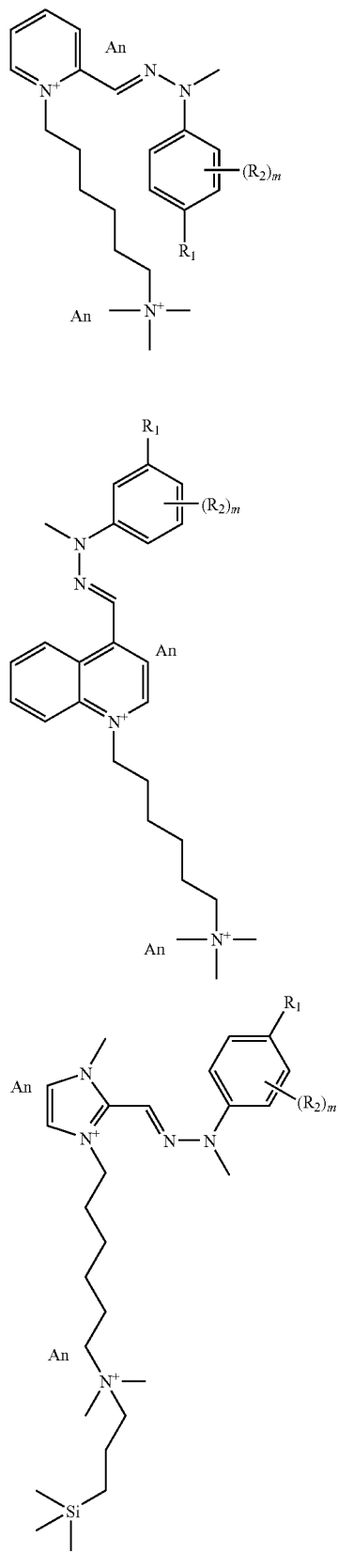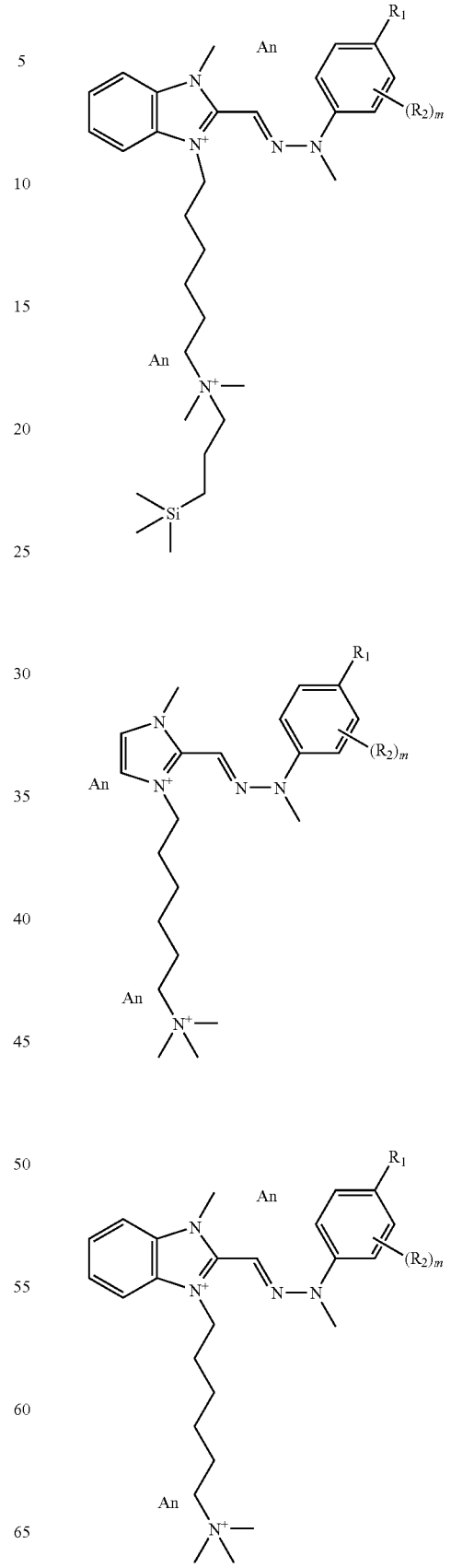

-continued
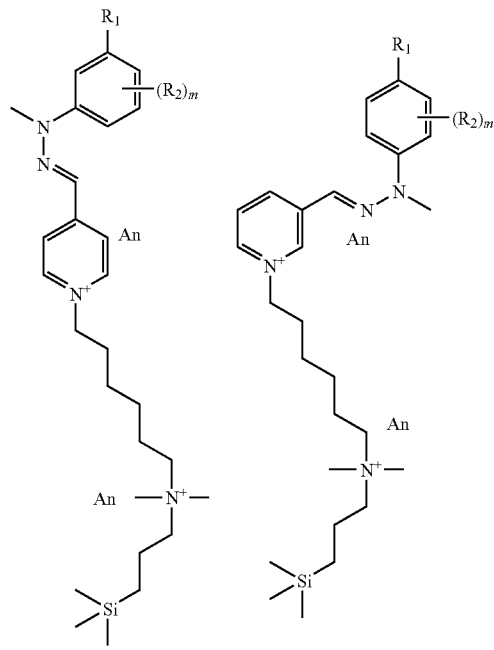
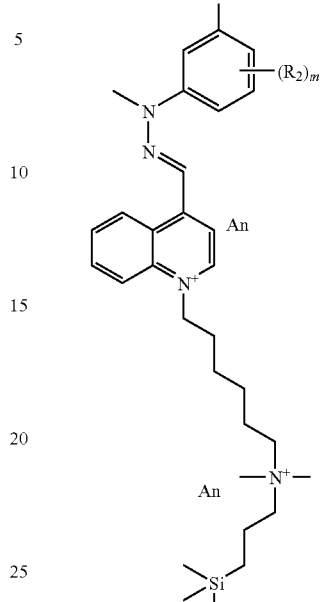
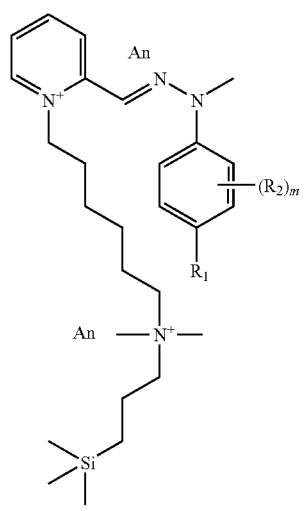
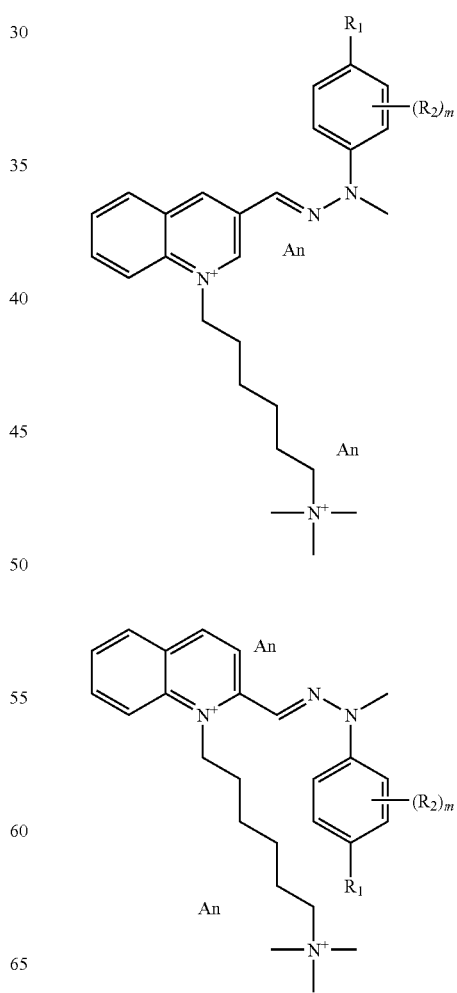

-continued
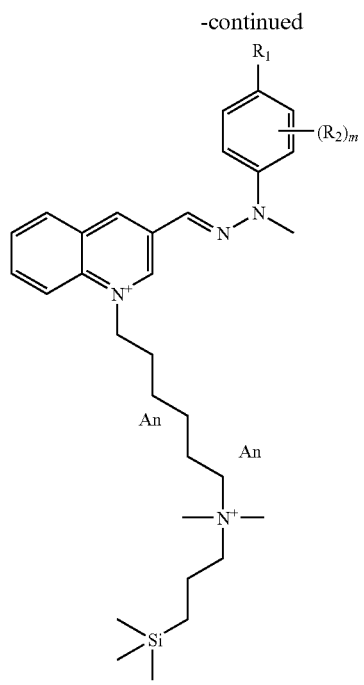
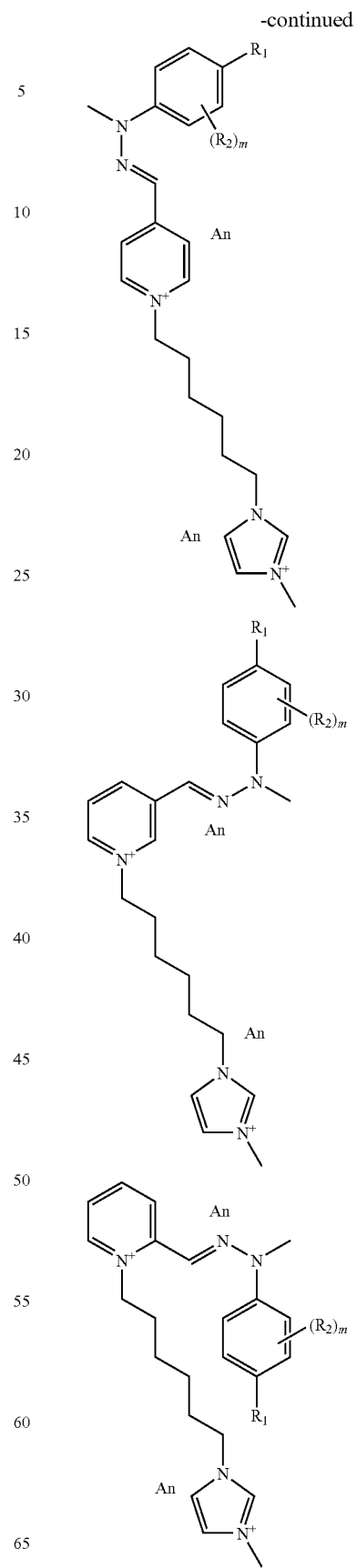

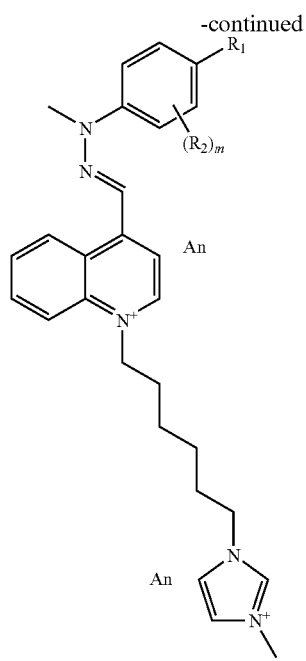
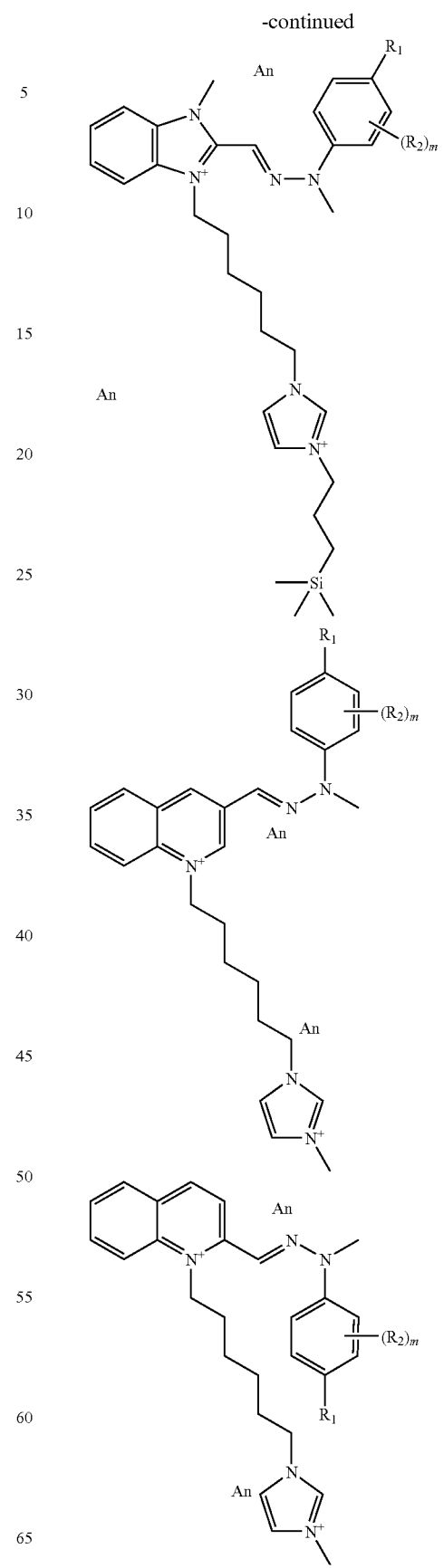

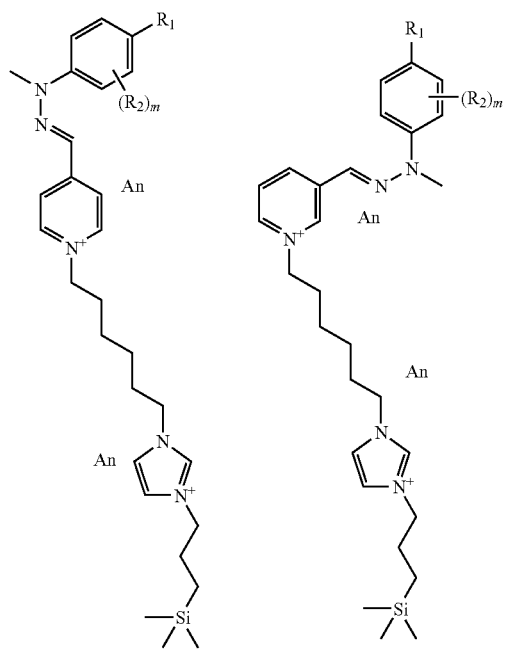
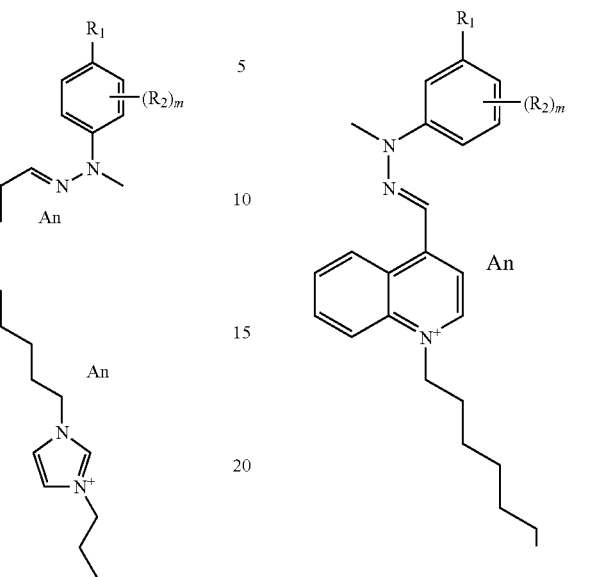
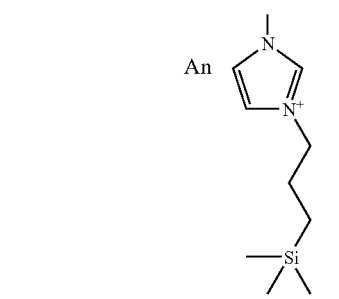
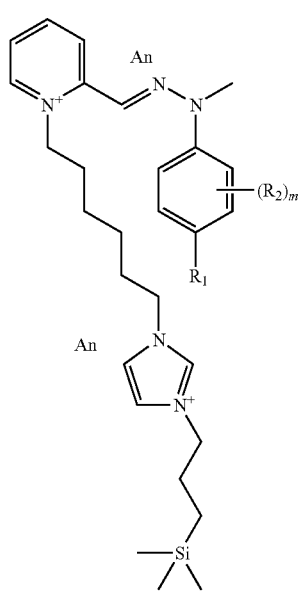
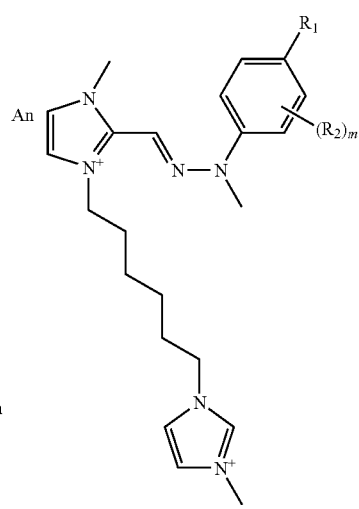

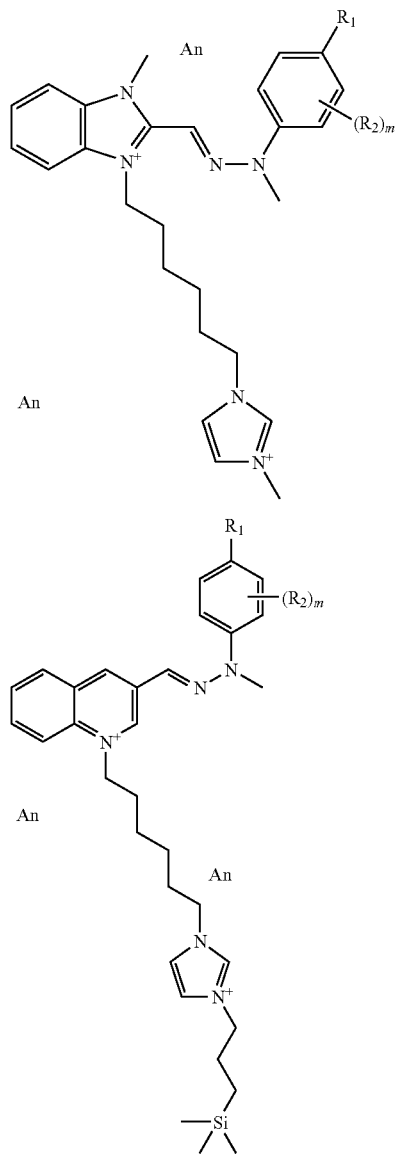
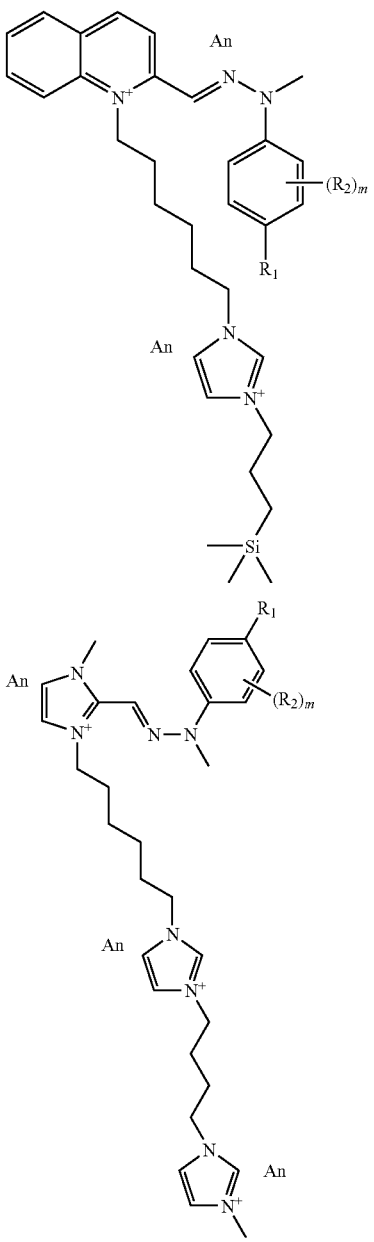

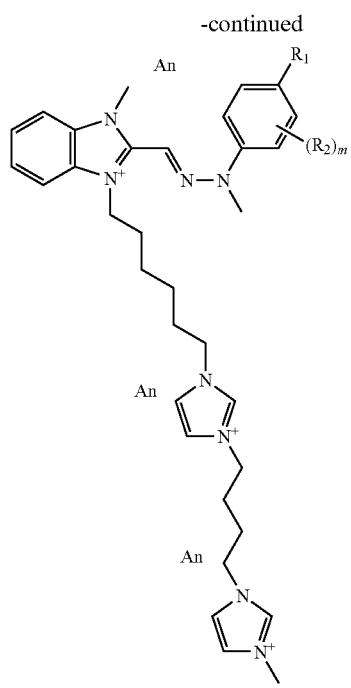
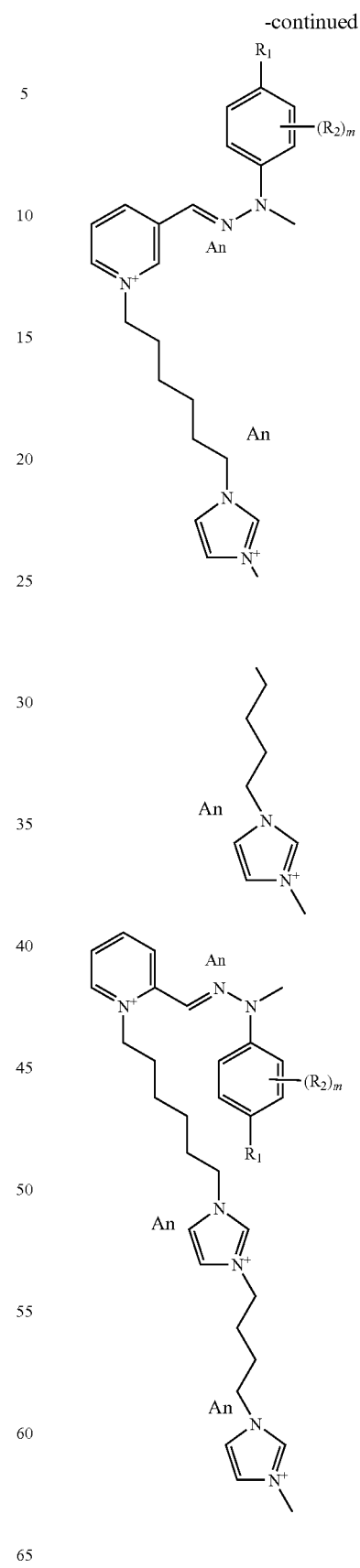

-continued
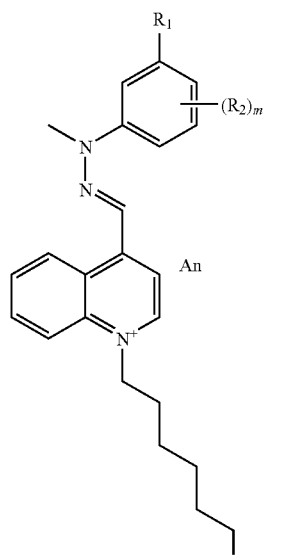
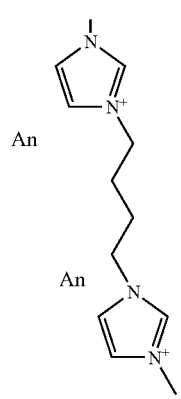
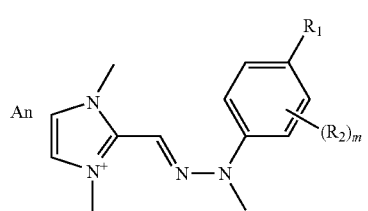
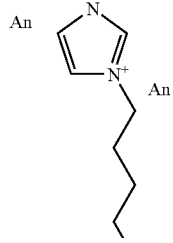
-continued
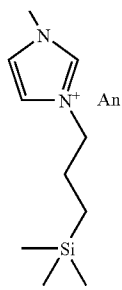
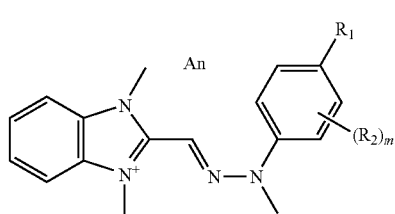
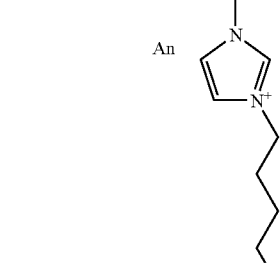
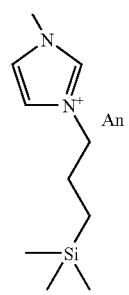

-continued
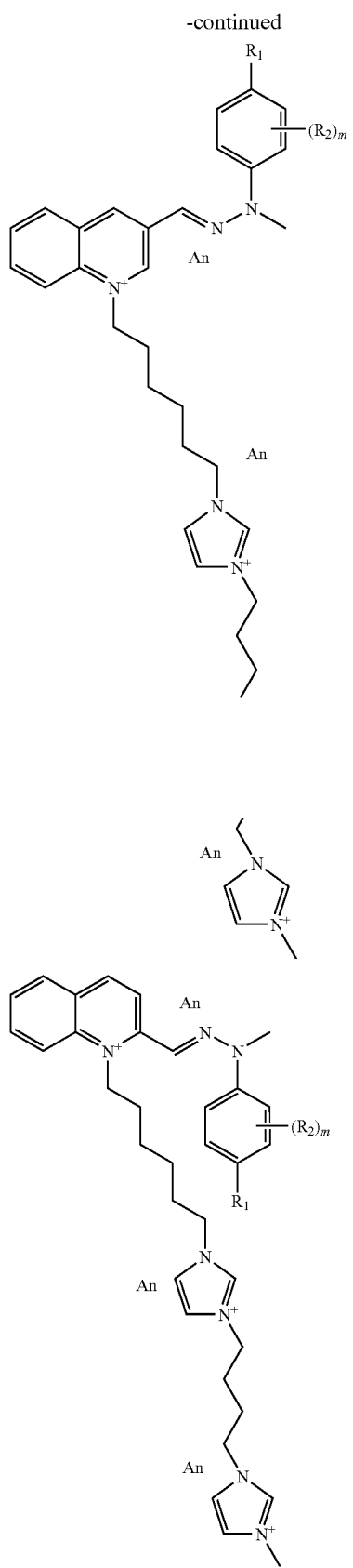
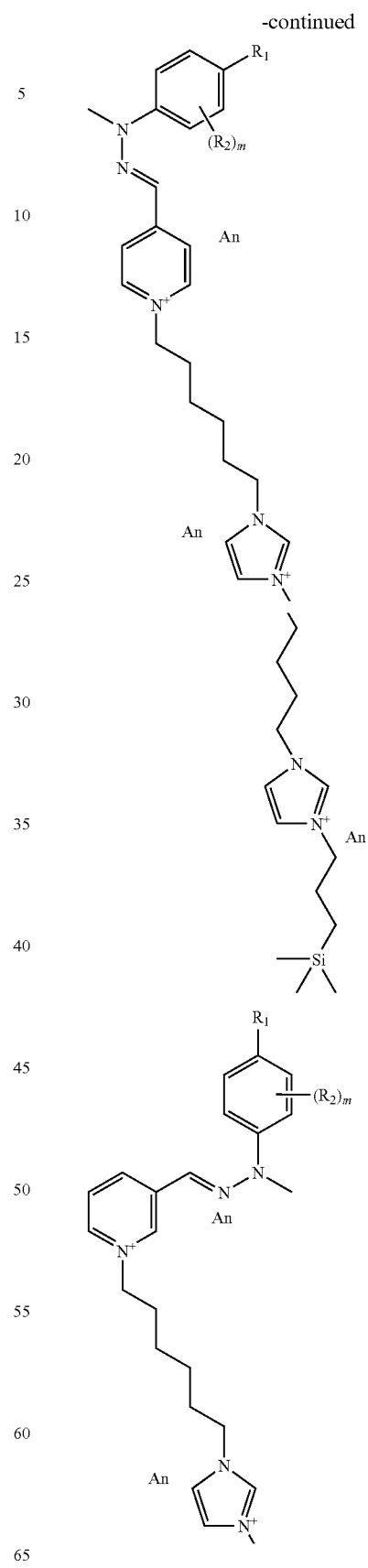

-continued
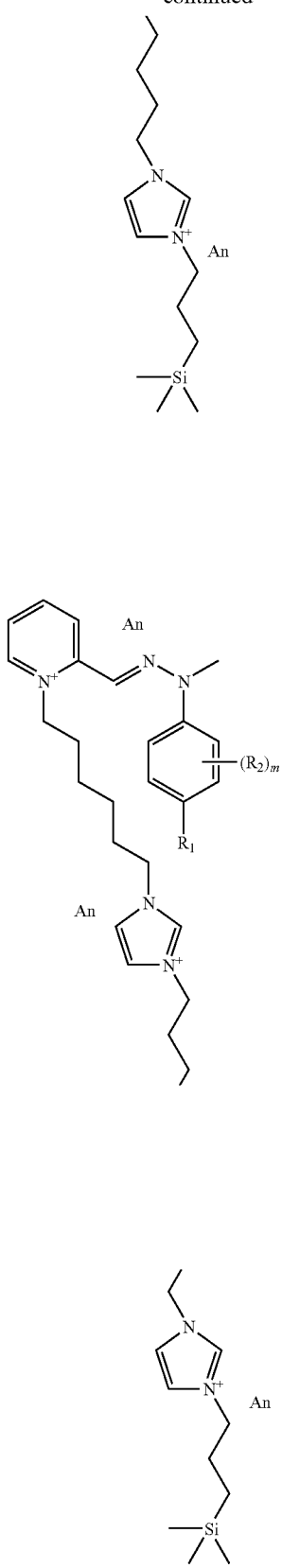
-continued
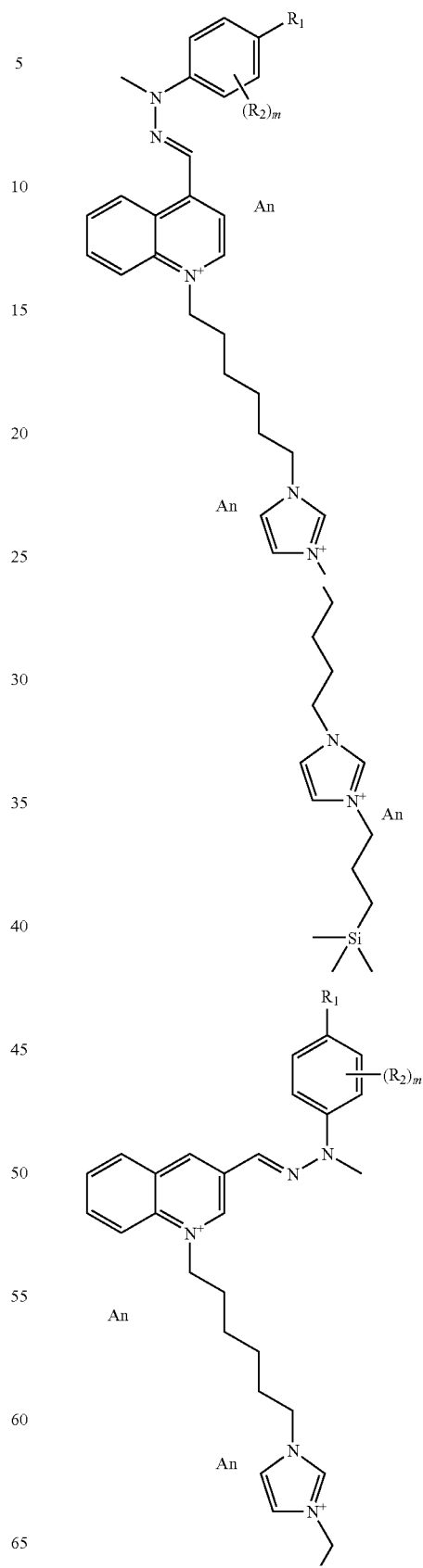

-continued
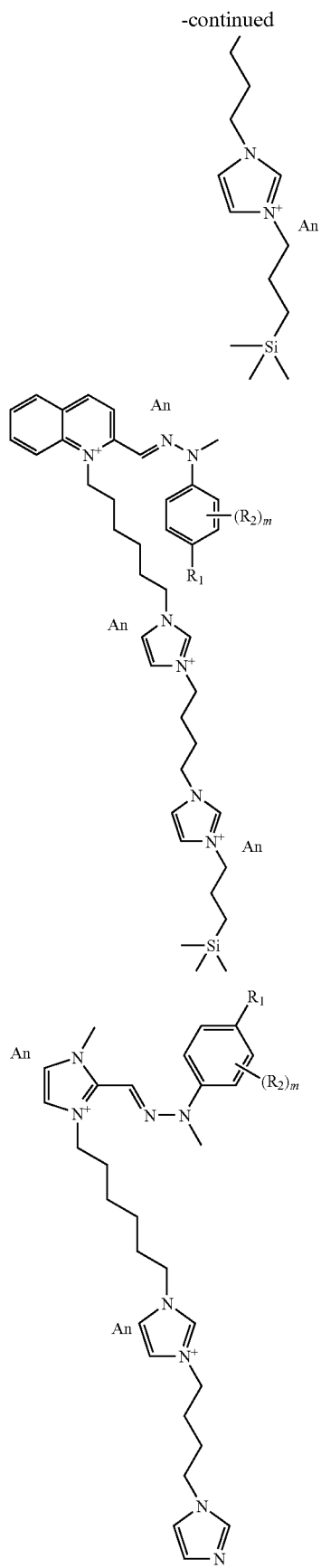
-continued
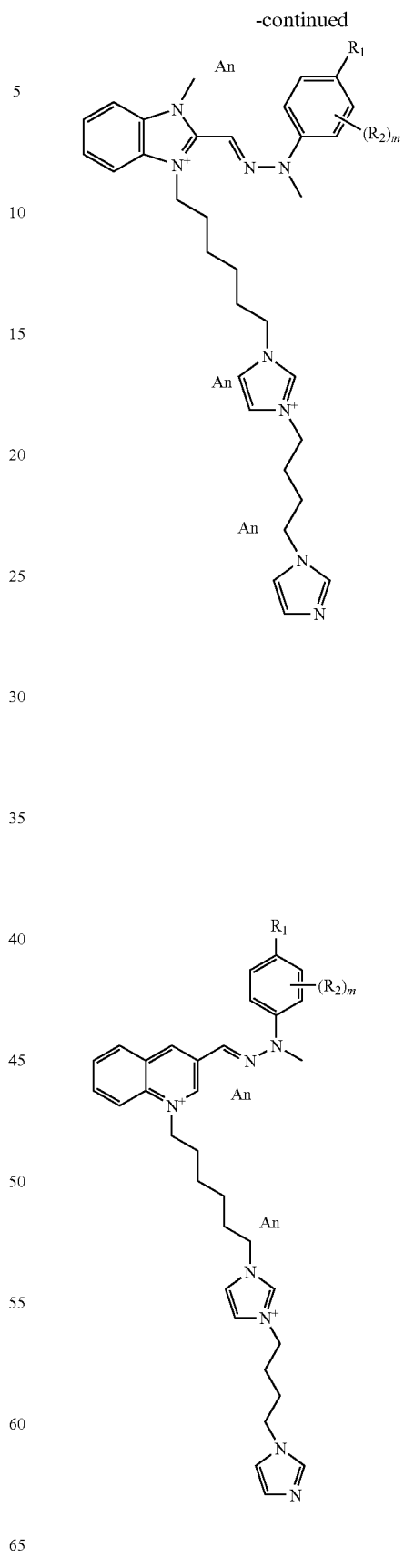

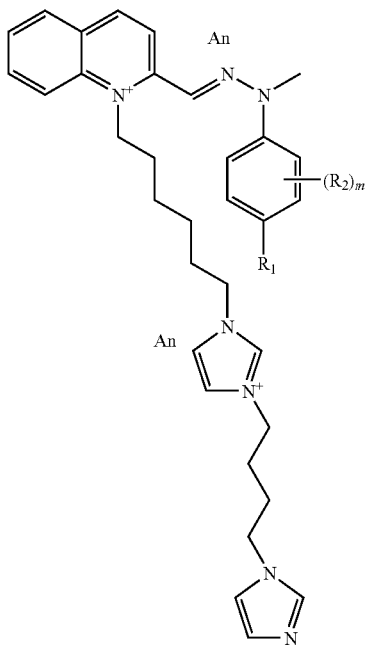

in which formulae, $R_1$, $R_2$, m and An have the same meanings as those indicated above, and R is chosen from a hydrogen atom and a methyl radical.

These compounds can be synthesized according to one of the reaction schemes below:

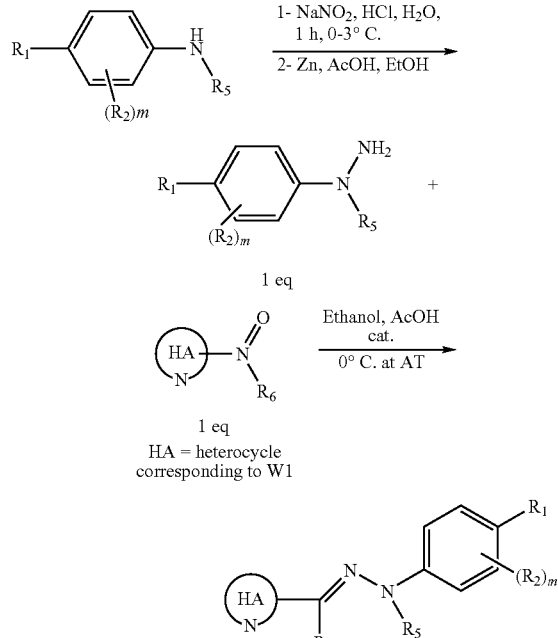

Synthesis of dicationic hydrazone:

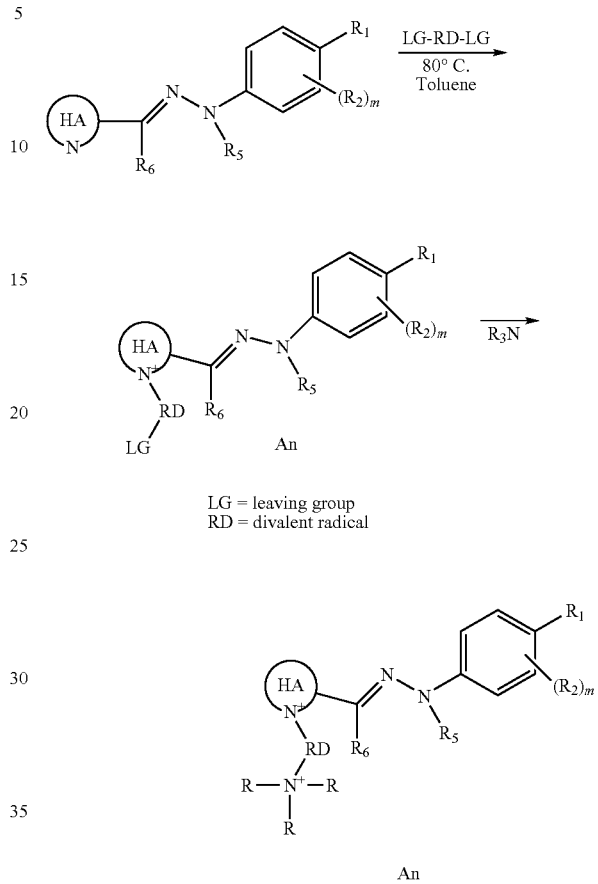

LG = leaving group
RD = divalent radical

R, which may or may not be identical, can also form a saturated, unsaturated or aromatic heterocycle comprising 5 or 6 ring members Synthesis of dicationic hydrazone:

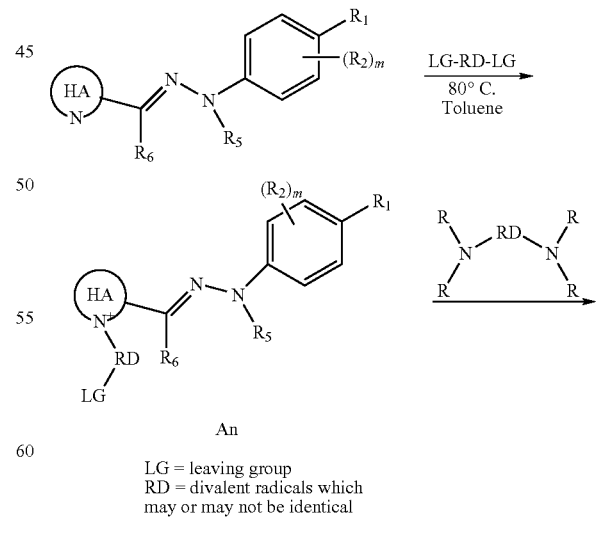

LG = leaving group
RD = divalent radicals which may or may not be identical

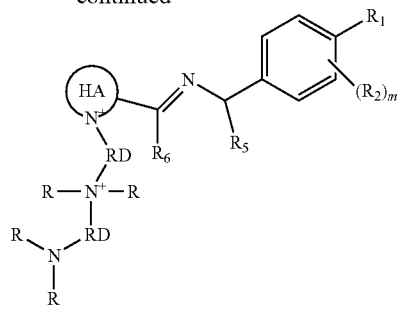

An

R, which may or may not be identical, can also form a saturated, unsaturated or aromatic heterocycle comprising 5 or 6 ring members It should be noted that the divalent radical RD is chosen according to the nature of the group Z; LG is in general a halogen atom such as bromine or chlorine, or mesyl or tosyl groups; and An originates from this leaving group LG.

To obtain a tricationic compound, a compound comprising a leaving group, for instance halogenated compounds, can be reacted in a manner known to those skilled in the art, and reacted with the final compound of the second dicationic compounds synthesis. As a result, a quaternization of the terminal amine function would be carried out.

The first step of hydrazine synthesis, if this compound is not commercially available, can be carried out in a known manner by reacting, in a first step, the corresponding amine with sodium nitrite, in an acidic aqueous medium. In a second step, a zinc-based catalyst is added, in the presence of acetic acid and ethanol.

Conventionally, this reaction is carried out at a temperature ranging from 0° C. to 13° C., for example, from 0 to 9° C.

It is not necessary to isolate the product obtained from the reaction medium.

A first step of condensation of a hydrazine derivative with a heteroaromatic ketone or aldehyde is subsequently carried out in a manner known to those skilled in the art.

According to at least one embodiment, the reaction is carried out in the presence of a catalytic amount of acid, for instance acetic acid, paratoluenesulphonic acid, citric acid, etc.

This reaction is normally carried out at a temperature ranging from 0° C. to 100° C., for example from 0° C. to 80° C.

Conventionally, the reaction is carried out in the presence of an appropriate solvent, among which non-limiting mention may be made of water, alcohols such as methanol or ethanol or isopropanol, dichloromethane, dimethylformamide, tetrahydrofuran, 1,3-dimethyl-2-oxohexahydropyrimidine, N-methylpyrrolidone and sulpholane. A compound that is a precursor of the units of formulae (1) to (8) is thus obtained.

A quaternization reaction of the heterocyclic nucleus is subsequently carried out.

According to at least one embodiment, this step comprises reacting the product resulting from the preceding step with a large amount (in general 5 to 10 equivalents) of a derivative having two leaving groups (noted LG-RD-LG on the reaction scheme).

By way of example, this derivative may be an optionally substituted α,ω-dihaloalkyl, such as 1,6-dibromohexane, 1,5-dichloropentane or 1,5-diiodohexane, or a dialkyl sulphonate or diaryl sulphonate such as 4-[(methylsulphonyl)oxy] butyl methanesulphonate or 7-{[(4-methylphenyl)sulphonyl]oxy}heptyl 4-methylbenzene-sulphonate.

This reaction is normally carried out at a temperature ranging from 50° C. to 130° C., for instance from 60° C. to 110° C.

Conventionally, the reaction is carried out in the absence or in the presence of an appropriate solvent such as, for example, 1,2-dichloroethane, toluene, 3,4,5,6-tetrahydro-2(1H)-pyrimidinone (DMPU), dimethylformamide (DMF) or N-methylpyrrolidone (NMP).

In the final step, the resulting product is reacted in the presence of a nucleophile (tertiary amine).

The tertiary amine, noted NR$_3$ in the reaction scheme, is a group that is a precursor of the cationic group of formula (a), (b), (c), (d), (e) or (f), and can, inter alia, correspond to imidazole, to methylimidazole, to 1-[4-(1H-imidazol-1-yl) butyl]-1H-imidazole, or to a tertiary amine such as trimethylamine, triethylamine or N-methylpyrrolidone.

This reaction is normally carried out at a temperature ranging from 50° C. to 130° C., for example from 60° C. to 110° C.

Conventionally, the reaction is carried out in the presence of an appropriate solvent such as, for example, dimethylformamide, butanol, 3,4,5,6-tetrahydro-2(1H)-pyrimidinone (DMPU), N-methylpyrrolidone (NMP) or sulpholane.

By way of non-limiting example, the following steps can also be carried out, depending on whether it is desired to obtain di-, tri- or tetracationic compounds comprising cations which may or may not be identical:

Synthesis of dicationic hydrazone:

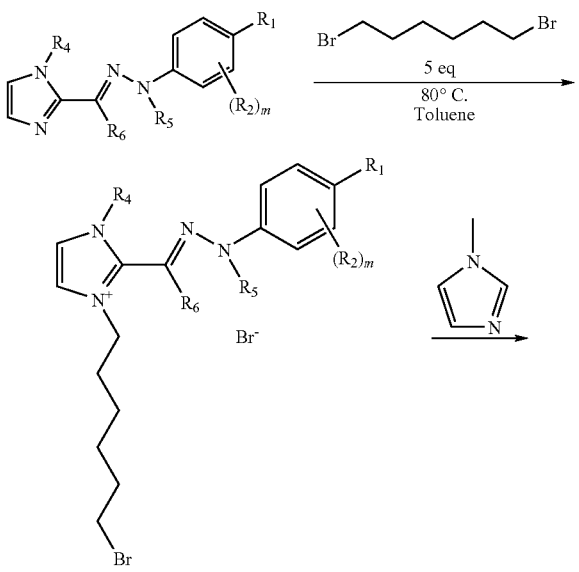

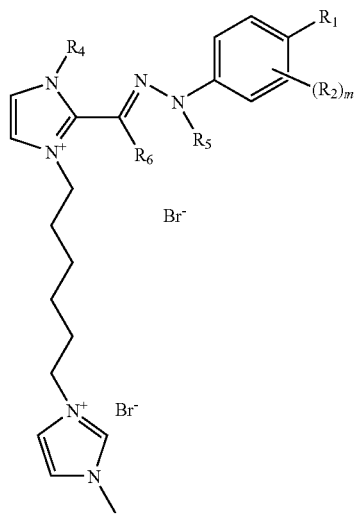
The same reaction can be carried out with the following amines:
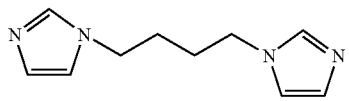
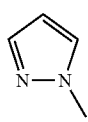     N(Et)$_3$   N(Me)$_3$,
Synthesis of identical-cation tricationic hydrazone:
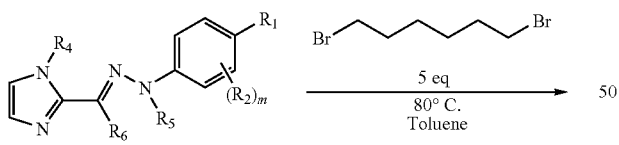
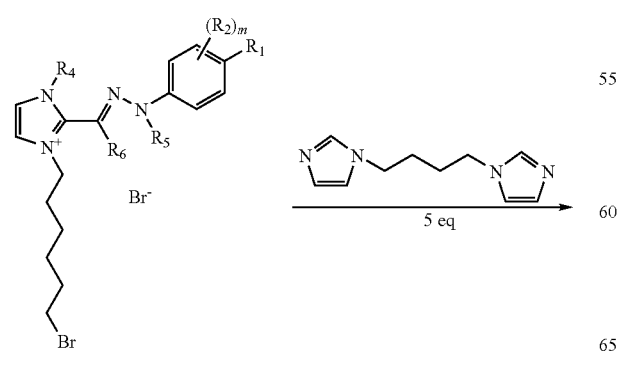
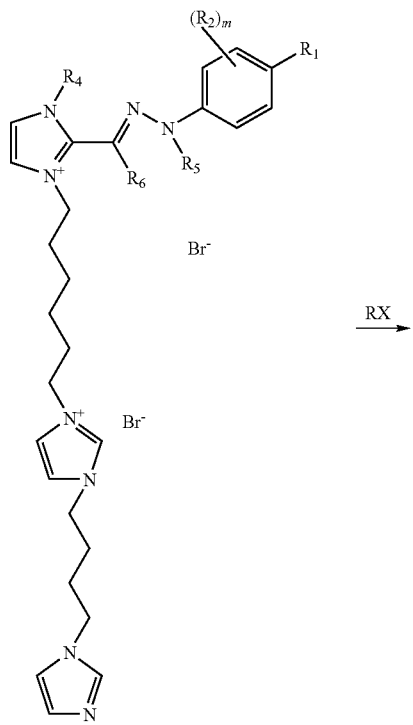
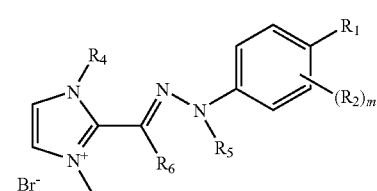
The same reaction can be carried out with the following amines (list not exhaustive):
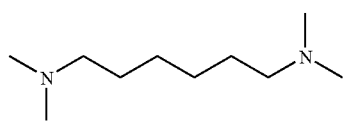

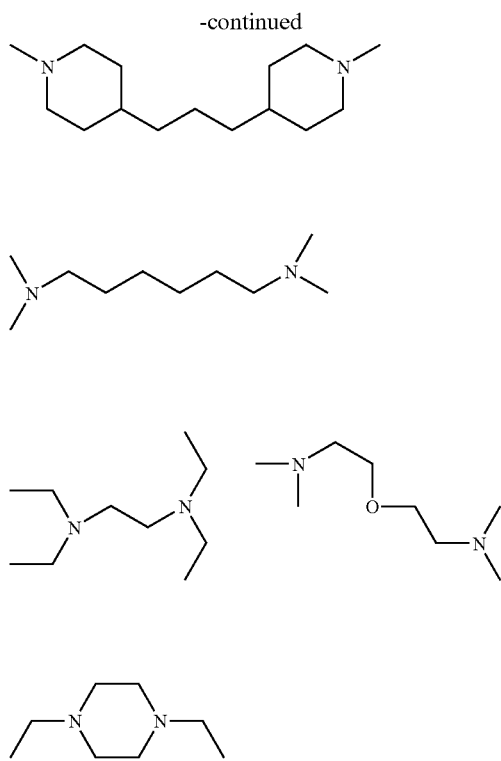

Synthesis of different-cation tri- and tetracationic hydrazone:

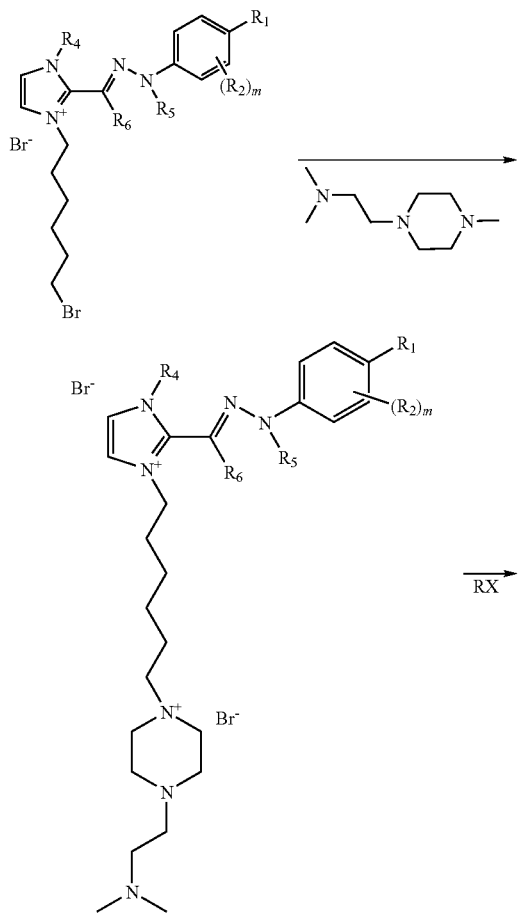

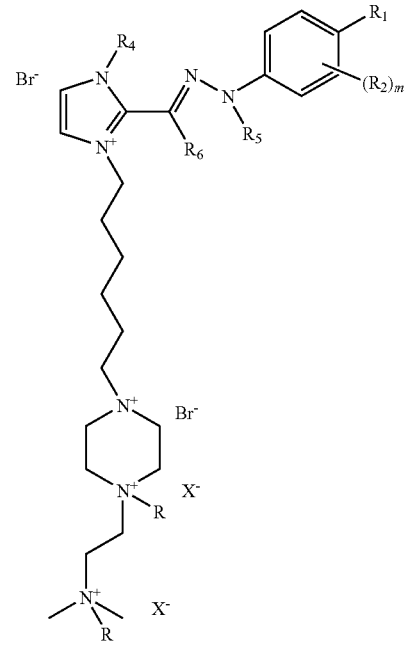

The same reaction can be carried out with the following amines:

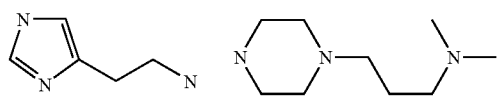

Another aspect of the present disclosure is a composition for dyeing human keratin fibers, such as the hair, comprising, in a cosmetically acceptable medium, at least one polycationic compound of formula (I) as described above, as direct dye(s).

According to at least one embodiment, the composition as disclosed herein comprises from 0.001% to 10%, for example, 0.01% to 10%, by weight of compound(s) of formula (I) relative to the total weight of the composition.

The dye composition in accordance with the present disclosure can also comprise at least one additional direct dye other than the polycationic compounds of formula (I), it being possible for these additional dyes, for instance, to be chosen from neutral, acidic or cationic nitrobenzene dyes, neutral, acidic or cationic azo direct dyes, neutral, acidic or cationic quinone, for example, anthraquinone, direct dyes, azine direct dyes, triarylmethane direct dyes, indoamine direct dyes, tetraazapentamethine-type dyes, and natural direct dyes.

Among the benzene-based direct dyes that can be used according to the present disclosure, mention may be made, in a nonlimiting manner, of the following compounds:
1,4-diamino-2-nitrobenzene,
1-amino-2-nitro-4-(β-hydroxyethylamino)benzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene 1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo direct dyes that can be used according to the present disclosure, non-limiting mention may be made of the cationic azo dyes described in patent applications WO 95/15144, WO-95/01772 and EP-714954, the content of which is incorporated herein as an integral part of the present disclosure.

Among these compounds, further non-limiting mention may be made of the following dyes:
1,3-dimethyl-2-[[4-(dimethylamino)phenyl]azo]-1H-imidazolium salt, such as chloride,
1,3-dimethyl-2-[(4-aminophenyl)azo]-1H-imidazolium salt, such as chloride,
1-methyl-4-[(methylphenylhydrazono)methyl]pyridinium salt, such as methyl sulphate.

Among the azo direct dyes, non-limiting mention may also be made of the following dyes, described in the Colour Index International, 3rd Edition:
Disperse Red 17
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24
Disperse Black 9.

Non-limiting mention may also be made of 1-(4'-aminodiphenylazo)-2-methyl-4-bis(β-hydroxyethyl)aminobenzene and 4-hydroxy-3-(2-methoxyphenylazo)-1-naphthalenesulphonic acid.

Among the quinone direct dyes, non-limiting mention may be made of the following dyes:
Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15
Basic Blue 99 and also the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine dyes, non-limiting mention may be made of the following compounds:
Basic Blue 17
Basic Red 2.

Among the triarylmethane dyes that can be used according to the present disclosure, non-limiting mention may be made of the following compounds:
Basic Green 1
Acid blue 9
Basic Violet 3
Basic Violet 14
Basic Blue 7
Acid Violet 49
Basic Blue 26
Acid Blue 7.

Among the indoamine dyes that can be used according to the present disclosure, non-limiting mention may be made of the following compounds:
2-β-hydroxyethylamino-5-[bis-(β-4'-hydroxyethyl)amino]anilino-1,4-benzoquinone
2-β-hydroxyethylamino-5-(2'-methoxy-4'-amino)anilino-1,4-benzoquinone
3-N-(2'-chloro-4'-hydroxy)phenylacetylamino-6-methoxy-1,4-benzoquinoneimine
3-N-(3'-chloro-4'-methylamino)phenylureido-6-methyl-1,4-benzoquinoneimine
3-[4'-N-(ethyl, carbamylmethyl)amino]phenylureido-6-methyl-1,4-benzoquinoneimine.

Among the tetraazapentamethine-type dyes that can be used according to the present disclosure, non-limiting mention may be made of the following compounds: 2-((E)-{(E)-[(1,3-dimethyl-1,3-dihydro-2H-imidazol-2-ylidene)hydrazono]methyl}diazenyl)-1,3-dimethyl-1H-imidazol-3-ium chloride, 2-{(E)-[(1Z)-N-(1,3-dimethyl-1,3-dihydro-2H-imidazol-2-ylidene)ethanehydrazonoyl]diazenyl}-1,3-dimethyl-1H-imidazol-3-ium chloride, 4-methoxy-2-((E)-{(1E)-1-[(2E)-(4-methoxy-1-methylpyridin-2(1H)-ylidene)hydrazono]ethyl}diazenyl)-1-methylpyridinium chloride, 1-methyl-2-((E)-{(1E)-1-[(2E)-(1-methylpyridin-2(1H)-ylidene)hydrazono]ethyl}diazenyl)pyridinium chloride, 1-(2-hydroxyethyl)-2-[(E)-((1E)-1-{(2E)-[1-(2-hydroxyethyl)pyridin-2(1H)-ylidene]hydrazono}ethyl)diazenyl]pyridinium chloride, 1-methyl-2-((E)-{(E)-[(2Z)-(1-methylpyridin-2(1H)-ylidene)hydrazono]methyl}diazenyl) pyridinium chloride, 1-(2-hydroxyethyl)-2-[(E)-((E)-{(2E)-[1-(2-hydroxyethyl)pyridin-2(1H)-ylidene]hydrazono}methyl)diazenyl]pyridinium acetate.

Among the natural additional direct dyes that can be used according to the present disclosure, non-limiting mention may be made of lawsone, juglone, alizarin, purpurin, carminic acid, kermesic acid, purpurogallin, protocatechaldehyde, indigo, isatin, curcumin, spinulosin and apigenidin. Use may also be made of extracts or decoctions comprising these natural dyes and according to at least one embodiment, henna-based poultices and extracts.

The at least one additional direct dye may be present in an amount ranging from 0.001% to 20% by weight, relative to the total weight of the ready-to-use composition, and even further, for example, from 0.005% to 10% by weight, relative to the total weight of the composition.

The composition of the present disclosure can also comprise at least one oxidation base as a mixture with at least one coupler, which are oxidation dye precursors.

By way of example, when present, each oxidation base can be chosen from para-phenylenediamines, bisphenylalkylenediamines, para-aminophenols, ortho-aminophenols, heterocyclic bases, and its (their) addition salt(s) with an acid.

Among para-phenylenediamines, non-limiting mention may be made, by way of example, of para-phenylenediamine, para-toluoylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl,β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-paraphenylenediamine, N-(β-methoxyethyl)-para-phenylenediamine, 4-aminophenylpyrrolidine, 2-thienyl-paraphenylenediamine, 2-β-hydroxyethylamino-5-aminotoluene and 3-hydroxy-1-(4'-aminophenyl) pyrrolidine, and acid-addition salts thereof.

In at least one further embodiment, the para-phenylenediamines are chosen from para-phenylenediamine, para-toluoylenediamine, 2-isopropyl-para-phenylenediamine, 2-β-hydroxyethylpara-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-paraphenylenediamine, 2-chloro-para-phenylenediamine and 2-β-acetylaminoethyloxy-para-phenylenediamine, and acid-addition salts thereof.

Among bisphenylalkylenediamines, non-limiting mention may be made, by way of example, of N,N'-bis(β-hydroxyethyl)-N,N'-bis(4'-aminophenyl)-1,3-diaminopropanol, N,N'-bis(βhydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and acid-addition salts thereof, for example.

Among para-aminophenols, non-limiting mention may be made, by way of example, of para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and acid-addition salts thereof.

Among ortho-aminophenols, non-limiting mention may be made, by way of example, of 2-aminophenol, 2-amino-5-methylphenol, 2-amino-6-methylphenol and 5-acetamido-2-aminophenol, and acid-addition salts thereof.

Among heterocyclic bases, non-limiting mention may be made, by way of example, of pyridine derivatives, pyrimidine derivatives and pyrazole derivatives.

Among the pyridine derivatives, non-limiting mention may be made of the compounds described, for example, in patents GB 1 026 978 and GB 1 153 196, as well as 2,5-diaminopyridine, 2-(4-methoxyphenyl)amino-3-aminopyridine and 3,4-diaminopyridine, and acid-addition salts thereof.

Other pyridine oxidation bases that can be used in the present disclosure are the 3-aminopyrazolo[1,5-a]pyridine oxidation bases or addition salts thereof described, for example in Patent Application FR 2 801 308. By way of example, non-limiting mention may be made of pyrazolo[1,5-a]pyridin-3-ylamine; 2-acetylaminopyrazolo[1,5-a]pyridin-3-ylamine; 2-morpholin-4-ylpyrazolo[1,5-a]pyridin-3-ylamine; 3-aminopyrazolo[1,5-a]pyridine-2-carboxylic acid; 2-methoxypyrazolo[1,5-a]pyridin-3-ylamine; (3-aminopyrazolo[1,5-a]pyridin-7-yl)methanol; 2-(3-aminopyrazolo[1,5-a]pyridin-5-yl)ethanol; 2-(3-aminopyrazolo[1,5-a]pyridin-7-yl)ethanol; (3-aminopyrazolo[1,5-a]pyridin-2-yl) methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyridin-3-ylamine; pyrazolo[1,5-a]pyridine-3,5-diamine; 5-morpholin-4-ylpyrazolo[1,5-a]pyridin-3-ylamine; 2-[(3-aminopyrazolo[1,5-a]pyridin-5-yl)-(2-hydroxyethyl)amino] ethanol; 2-[(3-aminopyrazolo[1,5-a]pyridin-7-yl)-(2-hydroxyethyl)amino]ethanol; 3-aminopyrazolo[1,5-a]pyridin-5-ol; 3-aminopyrazolo[1,5-a]pyridin-4-ol; 3-aminopyrazolo[1,5-a]pyridin-6-ol; 3-aminopyrazolo[1,5-a]pyridin-7-ol; and acid-addition salts thereof.

Among the pyrimidine derivatives, non-limiting mention may be made of the compounds described, for example, in patents DE 23 59 399; JP 88-169571; JP 05-63124; EP 0 770 375 or Patent Application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine or 2,5,6-triaminopyrimidine, and acid-addition salts thereof and tautomeric forms thereof, when a tautomeric equilibrium exists.

Among the pyrazole derivatives, non-limiting mention may be made of the compounds described in patents DE 38 43 892 and DE 41 33 957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3- hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole or 3,5-diamino-4-(β-hydroxyethyl)amino-1-methylpyrazole, and acid-addition salts thereof.

The at least one additional oxidation base optionally present in the composition of the present disclosure may be present in an amount ranging from 0.001% to 20% by weight of the total weight of the dye composition, for example, ranging from 0.005% to 6%.

If the composition according to the present disclosure comprises at least one additional oxidation base, it also comprises at least one coupler conventionally used for dyeing keratin fibers. Among these couplers, non-limiting mention may be made of meta-phenylenediamines, meta-diphenols, naphthalene couplers, heterocyclic couplers, and addition salts thereof.

By way of example, non-limiting mention may be made of 1,3-dihydroxybenzene, 1,3-dihydroxy-2-methylbenzene, 4chloro-1,3-dihydroxybenzene, 2,4-diamino-1-(β-hydroxyethyloxy)benzene, 2-amino-4-(β-hydroxyethylamino)-1 methoxy-benzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzo-morpholine, 3,5-diamino-2,6-dimethoxypyridine, 1N-(β-hydroxyethyl)amino-3,4-methylenedioxybenzene and 2,6-bis(β-hydroxyethylamino)toluene, and addition salts thereof.

In the composition of the present disclosure, if present, the at least one coupler is present in an amount ranging from 0.001% to 20% by weight of the total weight of the dye composition, for example, from 0.005% to 6%.

In general, the addition salts of the oxidation bases and of the couplers that can be used in the context of the present disclosure are, for instance, chosen from acid-addition salts, such as hydrochlorides, hydrobromides, sulphates, alkylsulphonic acids in which the linear or branched alkyl part is $C_1$-$C_6$, such as methylsulphonic acid for example, citrates, succinates, tartrates, lactates, tosylates, optionally substituted arylsulphonic acids such as, for example, benzenesulphonic acid or para-toluenesulphonic acid, phosphates and acetates.

The cosmetically acceptable medium as used herein is a cosmetic medium comprising water or a mixture of water and at least one organic solvent for solubilizing the compounds which would not be sufficiently water-soluble. By way of organic solvent, non-limiting mention may, for example, be made of $C_1$-$C_4$ lower alkanols, such as ethanol and isopropanol; polyols and polyol ethers, such as 2-butoxyethanol, propylene glycol, propylene glycol monomethyl ether, diethylene glycol monoethyl ether and diethylene glycol monomethyl ether, and also aromatic alcohols such as benzyl alcohol or phenoxyethanol, and mixtures thereof.

According to at least one embodiment, the at least one organic solvent may be present in an amount ranging from 1% to 40% by weight, relative to the total weight of the dye composition, and even further, for instance, ranging from 5% to 30% by weight.

The dye composition in accordance with the present disclosure may also comprise various adjuvants conventionally used in hair dyeing compositions, such as anionic, cationic, non-ionic, amphoteric or zwitterionic surfactants or mixtures thereof, anionic, cationic, non-ionic, amphoteric or zwitterionic polymers or mixtures thereof, inorganic or organic thickeners, and for example anionic, cationic, non-ionic and amophoteric polymeric associative thickeners, antioxidants, penetrating agents, sequestering agents, fragrances, buffers, dispersants, conditioning agents, for example volatile or non-volatile, modified or unmodified silicones, film-forming agents, ceramides, preserving agents and opacifiers.

The above adjuvants may be present in an amount for each ranging from 0.01% to 20% by weight, relative to the total weight of the composition.

Of course, those skilled in the art will take care to select this or these optionally additional compound(s) in such a way that the beneficial properties intrinsically associated with the dye composition in accordance with the present disclosure are not, or are not substantially, impaired by the envisaged addition(s).

The pH of the dye composition in accordance with the present disclosure may range from 3 to 12, and further, for example, from 5 to 11. It can be adjusted to the desired value by means of acidifying or basifying agents usually used for dyeing keratin fibers, or alternatively using standard buffer systems.

Among the acidifying agents, mention may be made, by way of non-limiting example, of inorganic or organic acids, such as hydrochloric acid, orthophosphoric acid, sulphuric acid, carboxylic acids, such as acetic acid, tartaric acid, citric acid or lactic acid, and sulphonic acids.

Among the basifying agents, mention may be made, by way of non-limiting example, of aqueous ammonia, alkaline carbonates, alkanolamines such as monoethanolamine, diethanolamine and triethanolamine and derivatives thereof, sodium hydroxide, potassium hydroxide and the compounds of formula (II) below:

(II)

wherein W is a propylene residue optionally substituted with a hydroxyl group or a $C_1$-$C_4$ alkyl radical; $R_a$, $R_b$, $R_c$ and $R_d$, which may be identical or different, are chosen from hydrogen, $C_1$-$C_4$ alkyl, and $C_1$-$C_4$ hydroxyalkyl radicals.

The dye composition according to the present disclosure may be in various forms, such as in the form of liquids, creams, gels, pastes or any other form suitable for dyeing keratin fibers, for instance human hair.

The process of the present disclosure is a process in which the composition according to the present disclosure as defined above is applied to the fibers.

According to at least one embodiment, the composition of the present disclosure is applied to the keratin fibers in the presence of an oxidizing agent for a period of time sufficient to obtain desired lightening.

The oxidizing agent can be added to the composition of the present disclosure at the time of use, or it may be used starting from an oxidizing composition containing it, which is applied simultaneously with or sequentially to the composition of present disclosure.

According to at least one embodiment, the composition according to the present disclosure comprises at least one oxidation dye precursor.

The mixture obtained is subsequently applied to the keratin fibers.

After a leave-in time of 3 minutes to 1 hour, and further from 5 to 50 minutes, the keratin fibers may be rinsed with water, optionally washed with shampoo, rinsed with water again, and then dried.

The oxidizing agents conventionally used for dyeing keratin fibers are, for example, hydrogen peroxide, urea peroxide, alkaline metal bromates, persalts such as perborates and persulphates, peracids, and oxidase enzymes, among which non-limiting mention may be made of peroxidases, 2-electron oxidoreductases such as uricases, and 4-electron oxigenases such as laccases. According to at least one embodiment, the composition comprising an oxidizing agent of peroxide type and/or an oxidizing agent of persalt type, for example a mixture of hydrogen peroxide and persulphates, hydrogen peroxide alone or the persulphate alone. According to at least one embodiment, the oxidizing agent is hydrogen peroxide alone.

The oxidizing composition may further comprise various adjuvants conventionally used in compositions for dyeing the hair and as disclosed herein.

Another aspect of the present disclosure is a multicompartment device comprising a first compartment comprising a dye composition as disclosed herein and a second compartment comprising a composition comprising at least one oxidizing agent.

According to another embodiment, the device comprises a first compartment comprising a composition that comprises at least one polycationic dye of formula (I) but no oxidation dye precursor (base, coupler), a second compartment comprising a composition comprising at least one oxidation dye precursor chosen from at least one oxidation base, optionally associated with at least one coupler, and a third compartment comprising a composition that comprises at least one oxidizing agent.

The information that has been given with respect to the nature of the dyes and of the ingredients that can be used in this field remains valid and reference may be made to the corresponding parts of the description. Thus, the compositions of the first, second and third compartments can each comprise the conventional additives of the dye compositions that can be used for dyeing human keratin fibers.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in its respective testing measurement.

The examples that follow are intended to illustrate the present disclosure without, however, being limiting in nature.

EXAMPLES

Example 1

Synthesis of Compound [5]: Synthesis of 1-(6-{3-[4-(1H-imidazol-1-yl)butyl]-1H-imidazol-3-ium-1-yl}hexyl)-4-{(E)-[methyl(phenyl)hydrazono]methyl}quinolinium dibromide

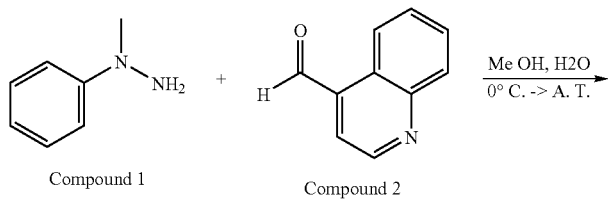

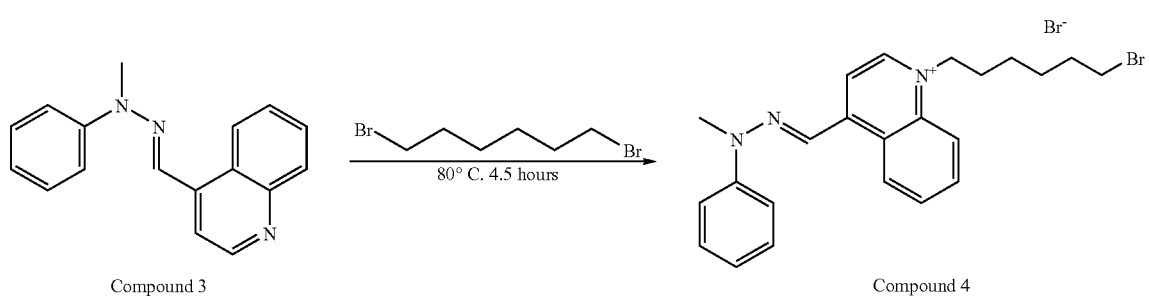

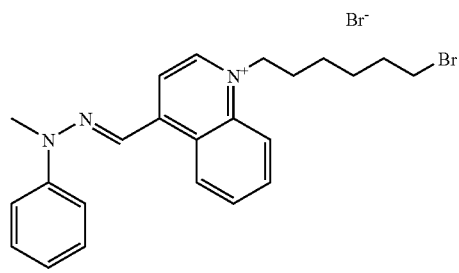

Compound 4

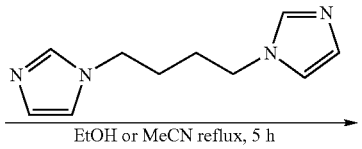

EtOH or MeCN reflux, 5 h

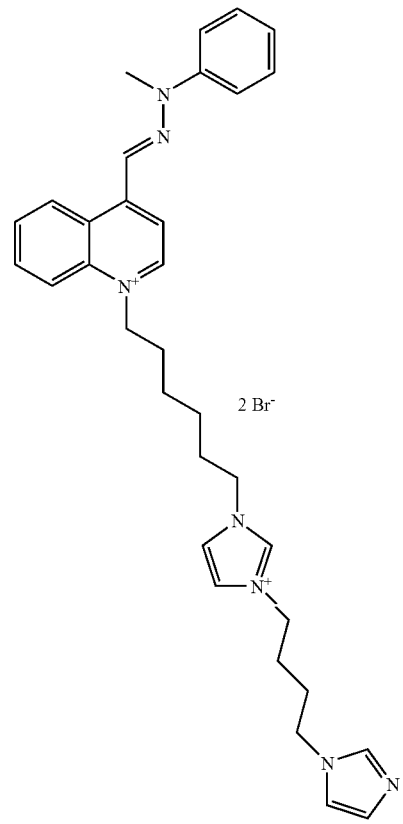

Compound 5

NB: Compounds 1 and 2 are commercially available.

Stage 1

4.7 ml (40 mmol) of 1-methyl-1-phenylhydrazine [1] in 8 ml of water were stirred at 0° C. (temperature of the reaction medium) in a 250 ml three-necked flask equipped with a thermometer and surmounted by a condenser. 6.8 g (40 mmol) of 4-quinolinecarboxaldehyde [2] in 40 ml of methanol were subsequently added slowly while maintaining the reaction medium at 0° C. The latter was subsequently brought slowly to ambient temperature. The reaction was then left at ambient temperature for 3 hours, during which time a yellow precipitate appeared.

The precipitate formed was subsequently filtered under vacuum, washed 3 times with water, and then dried under a strong vacuum. 10.3 g of a yellow powder corresponding to compound [3] were obtained.

The NMR spectra and the mass spectra were in accordance with the expected product [3].

Stage 2

10 ml of 1,6-dibromohexane were stirred at 80° C., in the presence of 0.5 g of compound [3], in a 250 ml three-necked flask equipped with a thermometer and surmounted by a condenser. After reaction for 4.5 hours, the dark orange-colored reaction medium was subsequently brought to ambient temperature. A precipitate gradually formed during the cooling.

Said precipitate was subsequently filtered under vacuum, washed with toluene, and then dried under a strong vacuum. 0.775 g of an orange powder corresponding to compound [4] was obtained.

The NMR spectra and the mass spectra were in accordance with the expected product [4].

Stage 3

The intermediate [4] (4.5 g, 9 mmol) and 17 g of 1,4-bis(1-imidazolyl)butane (90 mmol) solubilized in 90 ml of acetonitrile were stirred at reflux, in a 250 ml three-necked flask equipped with a thermometer and surmounted by a condenser. After reflux for 7 hours, the reaction mixture was cooled and then concentrated; the residue obtained was subsequently purified by alumina column chromatography, to give 2.5 g of compound [5].

The NMR spectra and the mass spectra were in accordance with the expected product [5].

Example 2

Synthesis of Compound [9]: Synthesis of 1-(6-{3-[4-(1H-imidazol-1-yl)butyl]-1H-imidazol-3-ium-1-yl}hexyl)-2-{(E)-[methyl(phenyl)hydrazono]methyl}quinolinium dibromide

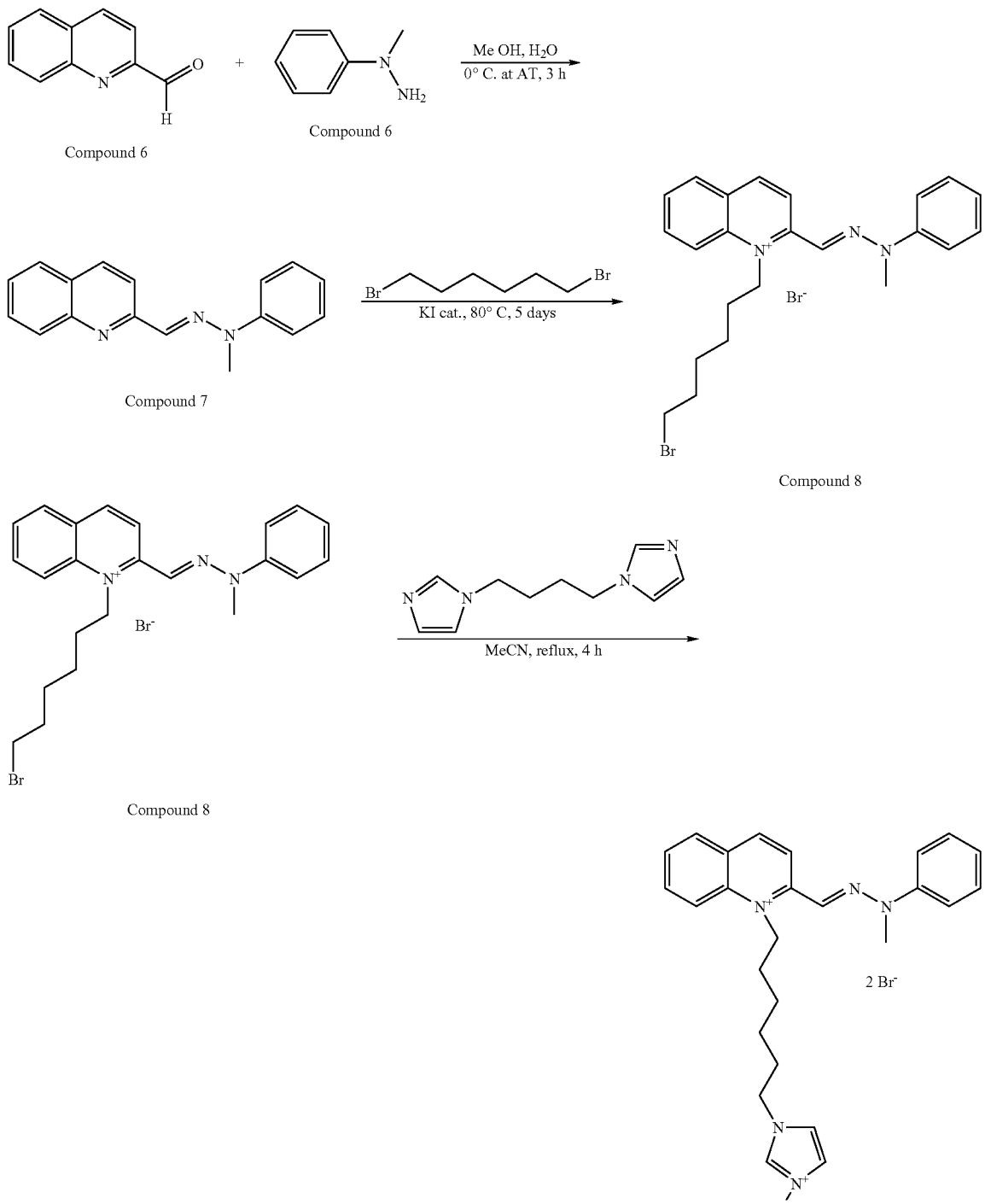

Compound 9

NB: compound 6 is a commercially available compound.

Stage 1

4.7 ml (40 mmol) of 1-methyl-1-phenylhydrazine [1] in 8 ml of water were stirred at 0° C., in a 250 ml three-necked flask equipped with a thermometer and surmounted by a condenser. Subsequently, 6.8 g (40 mmol) of 2-quinolinecarboxyaldehyde [6] solubilized in 40 ml of methanol were then added slowly. Subsequently, the reaction medium was stirred for 3 hours at ambient temperature. A precipitate gradually formed during the reaction. This precipitate was subsequently filtered off under vacuum, washed three times with water, and then dried under a strong vacuum. 10.3 g of compound [7] were obtained.

The NMR spectra and the mass spectra were in accordance with the expected product [7].

Stage 2

5.22 g (20 mmol) of the intermediate [7] solubilized in 20 ml of 1,6-dibromohexane were stirred at 80° C. for 5 days, in the presence of a catalytic amount of KI (60 mg), in a 250 ml three-necked flask equipped with a thermometer and surmounted by a condenser. After reaction, the reaction medium was cooled to ambient temperature. A precipitate gradually formed during the cooling. This precipitate was subsequently filtered off under vacuum, washed with ethyl acetate, and then dried. After flash silica column purification, 0.8 g of compound [8] was obtained.

The NMR spectra and the mass spectra were in accordance with the expected product [1].

Stage 3

The intermediate [8] (1.6 g, 3.2 mmol), and 6 g of 1,4-bis (1-imidazolyl)butane (32 mmol) solubilized in 20 ml of acetonitrile were stirred at reflux in a 250 ml three-necked flask equipped with a thermometer and surmounted by a condenser. After reflux for 4 hours, the reaction medium was cooled and then concentrated, the residue obtained was subsequently purified by alumina column chromatography (MeOH/CH$_2$Cl$_2$=1/100 to 1/10), to give 1.2 g of compound [9].

The NMR spectra and the mass spectra were in accordance with the expected product [9].

Example 3

Synthesis of Compound [13]: Synthesis of 1-(6-{3-[4-(1H-imidazol-1-yl)butyl]-1H-imidazol-3-ium-1-yl}hexyl)-2-{(E)-[methyl(phenyl)hydrazono]methyl}pyridinium dibromide

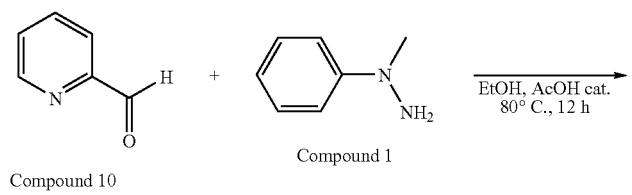

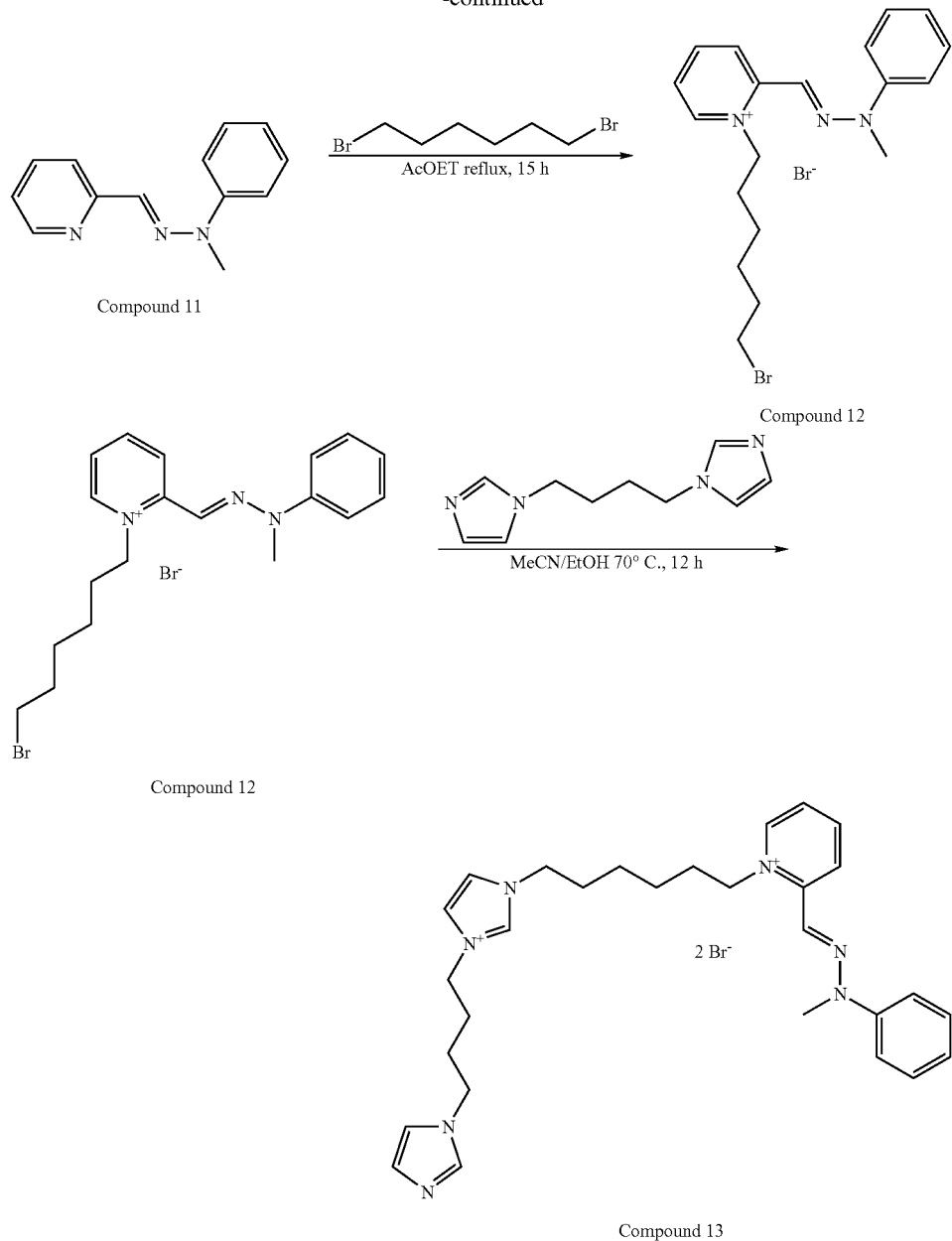

NB: Compound 10 is a commercially available compound.

Stage 1

1.07 g (10 mmol) of 2-pyridinecarboxaldehyde [10] and 1.22 g (10 mmol) of 1-methyl-1-phenylhydrazine [1] in 20 ml of ethanol were stirred at 80° C. for 12 h, in the presence of 3 drops of acetic acid, in a 250 ml three-necked flask equipped with a thermometer and surmounted by a condenser.

After concentration of the reaction medium, a residue was obtained; said residue was neutralized to pH 8 with a saturated solution of NaHCO$_3$ and then extracted three times with ethanol acetate. The organic phases were combined and then dried over magnesium sulphate, filtered and evaporated, to give 2 g of product [11].

The NMR spectra and the mass spectra were in accordance with the expected product [11].

Stage 2

2.1 g (10 mmol) of intermediate [11] and 24.4 g (100 mmol) of 1,6-dibromohexane in 15 ml of ethyl acetate were stirred at 80° C. for 15 h, in a 250 ml three-necked flask equipped with a thermometer and surmounted by a condenser. The dark yellow-colored reaction medium was subsequently brought to ambient temperature. A precipitate gradually formed during the cooling. This precipitate was subsequently filtered off under vacuum, washed with ethyl acetate, and then dried. After flash silica column purification (methanol/dichloromethane: 1/30 to 1/10), 2.5 g of a dark yellow powder corresponding to compound [12] were obtained.

The NMR spectra and the mass spectra were in accordance with the expected product [12].

Stage 3

The intermediate [12] (1.5 g, 2.7 mmol) and 5.1 g of 1,4-bis(1-imidazolyl)butane (27 mmol) solubilized in a mixture composed of 20 ml of acetonitrile and ml of ethanol were stirred at 70° C., in a 250 ml three-necked flask equipped with a thermometer and surmounted by a condenser. After reflux for 12 hours, the reaction mixture was cooled and then concentrated; the residue obtained is subsequently purified by alumina column chromatography (MeOH/CH$_2$Cl$_2$=1/100 to 1/10), to give 1.1 g of compound [13].

The NMR spectra and the mass spectra were in accordance with the expected product [13].

Example 4

Synthesis of Compound [17]: Synthesis of 1-(6-{3-[4-(1H-imidazol-1-yl)butyl]-1H-imidazol-3-ium-1-yl}hexyl)-4-{(E)-[methyl(phenyl)hydrazono]methyl}pyridinium dibromide

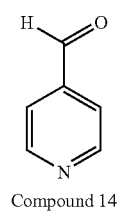
Compound 14

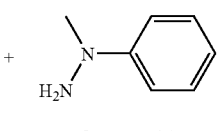
Compound 1

EtOH. AcOH
0° C. then 65° C.

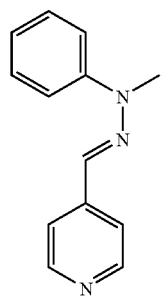
Compound 15

Br–(CH$_2$)$_6$–Br (5 eq.)
Toluene, 80° C. 4.5 hours

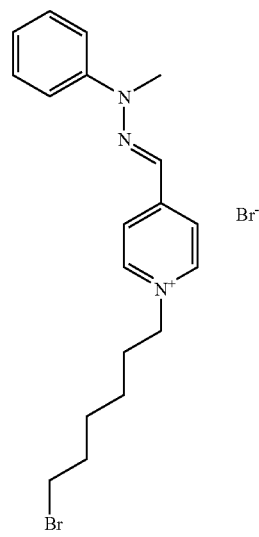
compound 16

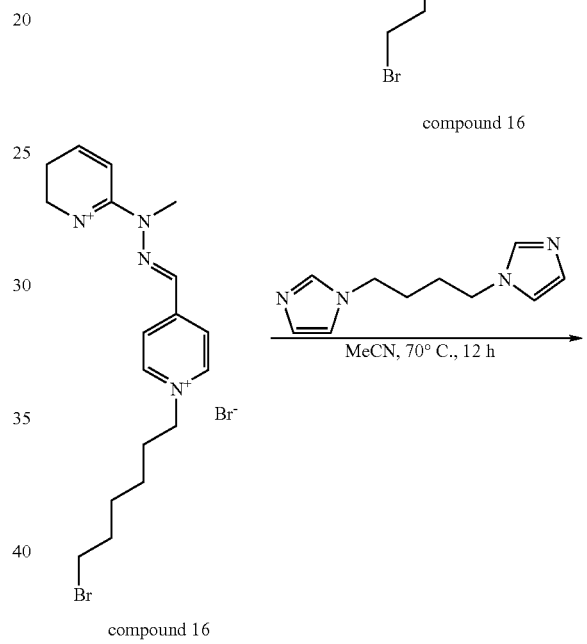
compound 16

MeCN, 70° C., 12 h

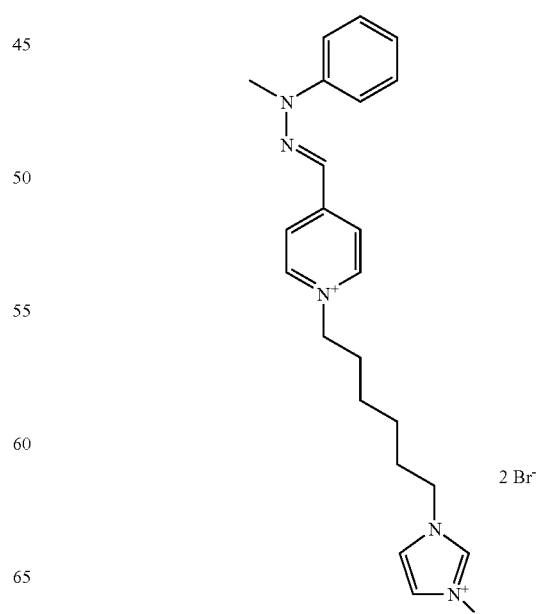
2 Br⁻

-continued

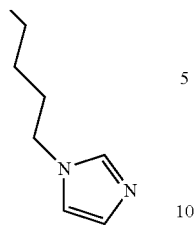

Compound 17

NB: Compound 14 is a commercially available compound.

Stage 1

One equivalent of N-methylphenylhydrazine (58.76 g; 0.4809 mol, compound [1]) was diluted in 50 ml of ethanol, in a three-necked flask surmounted by a condenser, and 1.5 ml of acetic acid were added. The reaction medium was then stirred at 0° C. Using a dropping funnel, 1 equivalent of 4-pyridinecarboxaldehyde (51.5 g; 0.4808 mol, compound [14]) was added. After addition of the aldehyde, the reaction medium was heated at 65° C. (oil bath temperature) for 13 hours.

The reaction medium was subsequently poured into a water-ice (1/3) mixture. The mixture was then stirred. After stirring, the oily residue resulted in a yellow powder being obtained. This powder was then filtered off and then washed several times with water. After drying, 83.9 g of compound [15] were obtained.

The NMR spectra and the mass spectra were in accordance with the expected product [15].

Stage 2

Compound [15] (80.1 g, 0.379 mol) was diluted in 250 ml of toluene, in a 3-liter three-necked flask surmounted by a condenser. The mixture was brought to 80° C. and a solution of 1,6-dibromohexane (1.94 mol) in 750 ml of toluene was added in 10 minutes. A precipitate formed during the reaction. After reacting for 4.5 hours, the reaction medium was cooled and then filtered.

Purification: The precipitate obtained was washed with 200 ml of toluene and then 100 ml of petroleum ether. This precipitate was subsequently solubilized in 1 liter of dichloromethane and then extracted with water. The organic phase was washed 4 times with water, dried over magnesium sulphate, filtered, and then concentrated. A brown oil was obtained, which was taken up with 50 ml of toluene. A yellow precipitate was obtained, which was separated by filtration and then dried, to give 95.1 g of compound [16] in the form of a yellow powder.

The NMR spectra and the mass spectra were in accordance with the expected product [16].

Stage 3

The intermediate [16] (1.6 g, 3 mmol) and 5.7 g of 1,4-bis(1-imidazolyl)butane (30 mmol) solubilized in 50 ml of acetonitrile were stirred at reflux in a 250 ml three-necked flask equipped with a thermometer and surmounted by a condenser. After reflux for 12 hours, the reaction mixture was cooled and then concentrated; the residue obtained was subsequently purified by alumina column chromatography (MeOH/CH$_2$Cl$_2$=1/100 to 1/10), to give 1.05 g of compound [17].

The NMR spectra and the mass spectra were in accordance with the expected product [17].

Example 5

Synthesis of Compound [21]: Synthesis of 3-(6-{3-[4-(1H-imidazol-1-yl)butyl]-1H-imidazol-3-ium-1-yl}hexyl)-1-methyl-2-{(E)-[methyl(phenyl)hydrazono]methyl}-1H-imidazol-3-ium dibromide

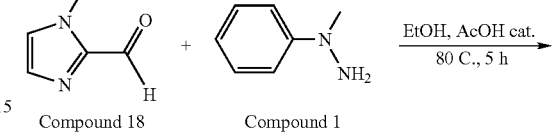

Compound 18              Compound 1

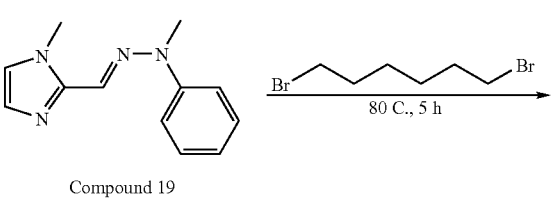

Compound 19

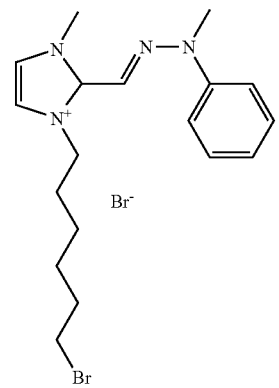

Compound 20

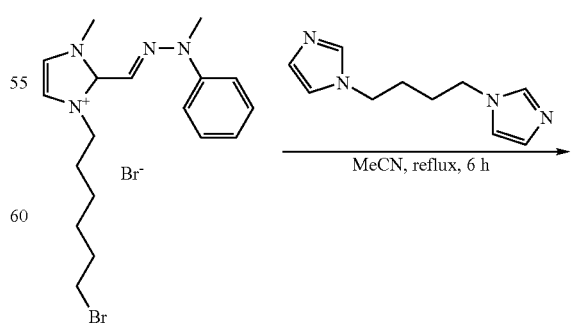

Compound 20

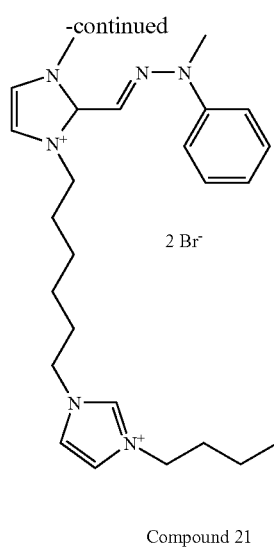

Compound 21

NB: Compound 18 is a commercially available compound.

Stage 1

2.2 g (20 mmol) of 1-methyl-2-imidazolecarboxaldehyde [18] and 2.44 g (20 mmol) of 1-methyl-1-phenylhydrazine [1] in 50 ml of ethanol were stirred at 80° C., in a 250 ml three-necked flask equipped with a thermometer and surmounted by a condenser, in the presence of 3 drops of acetic acid. After reacting for 5 hours, the medium was brought back to ambient temperature and the solvent was concentrated; the powder obtained was washed with diethyl ether. After drying, 4 g of compound [19] were obtained.

The NMR spectra and the mass spectra were in accordance with the expected product [19].

Stage 2

1.1 g (5 mmol) of intermediate [19] and 12 ml (80 mmol) of 1,6-dibromohexane were stirred at 80° C. in a 250 ml three-necked flask equipped with a thermometer and surmounted by a condenser. After heating for 5 hours, the reaction mixture was cooled to ambient temperature. A yellow precipitate gradually formed during the cooling. This precipitate was subsequently filtered off, and then washed with ethyl acetate and, finally, dried under a strong vacuum, to give 2.1 g of compound [20].

The NMR spectra and the mass spectra were in accordance with the expected product [20].

Stage 3

The intermediate [20] (1.2 g, 2.6 mmol) and 5 g of 1,4-bis (1-imidazolyl)butane (26 mmol) solubilized in 70 ml of acetonitrile were stirred at reflux in a 250 ml three-necked flask equipped with a thermometer and surmounted by a condenser. After reflux for 6 hours, the reaction mixture was cooled and then concentrated; the residue obtained was subsequently solubilized in water and then extracted with dichloromethane. The aqueous phase was concentrated. The powder obtained was purified by alumina column chromatography (MeOH/CH$_2$Cl$_2$=1/100 to 1/20), to give 1.02 g of compound [21].

The NMR spectra and the mass spectra were in accordance with the expected product [21].

Example 6

Synthesis of Compound [25]: Synthesis of 3-(6-{3-[4-(1H-imidazol-1-yl)butyl]-1H-imidazol-3-ium-1-yl}hexyl)-1-methyl-2-{(E)-[methyl(phenyl)hydrazono]methyl}-1H-3,1-benzimidazol-3-ium dibromide

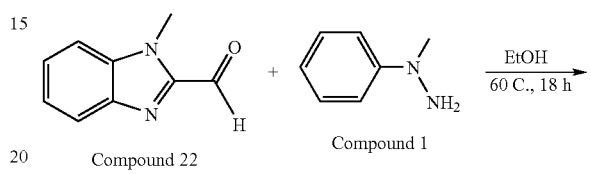

Compound 22        Compound 1

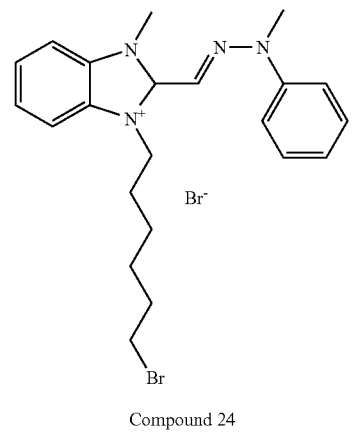

Compound 23

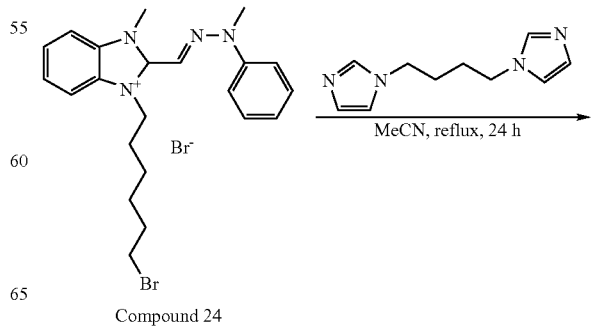

Compound 24

Compound 24

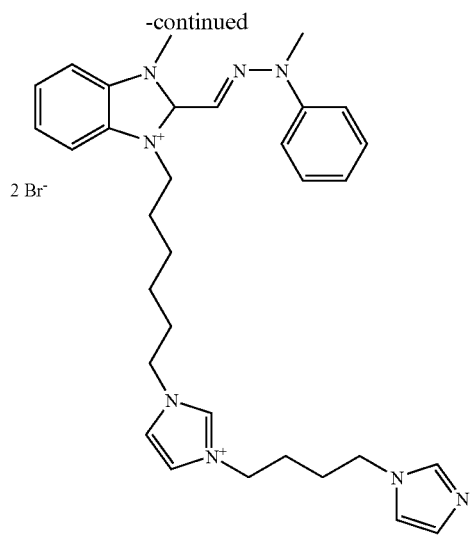

Compound 25

NB: Compound 22 is a commercially available compound.

Stage 1

2.4 g (15 mmol) of 1-methyl-2-formylbenzimidazole [22] and 1.8 g (15 mmol) of 1-methyl-1-phenylhydrazine [1] in 50 ml of ethanol were stirred at 60° C. in a 250 ml three-necked flask equipped with a thermometer and surmounted by a condenser. After reacting for 18 hours, the reaction medium was brought back to ambient temperature and then poured over an ice bath; a precipitate appears. This precipitate was subsequently filtered off, and then washed with water and, finally, dried. 3.9 g of compound [23] were obtained.

The NMR spectra and the mass spectra were in accordance with the expected product [23].

Stage 2

3.9 g (14.7 mmol) of intermediate [23] and 23 ml (147 mmol) of 1,6-dibromohexane were stirred at 100° C. in a 250 ml three-necked flask equipped with a thermometer and surmounted by a condenser. After reacting for 5 hours, the reaction medium was cooled to ambient temperature. A yellow precipitate gradually formed during the cooling. This precipitate was subsequently filtered off, washed several times with ethyl acetate, and then dried. 7 g of compound [24] were obtained.

The NMR spectra and the mass spectra were in accordance with the expected product [24].

Stage 3

The intermediate [24] (1.5 g, 3 mmol) and 5.7 g of 1,4-bis (1-imidazolyl)butane (30 mmol) solubilized in 90 ml of acetonitrile were stirred at reflux, in a 250 ml three-necked flask equipped with a thermometer and surmounted by a condenser. After reflux for 24 hours, the reaction mixture was cooled and then concentrated; the residue obtained was subsequently purified by alumina column chromatography, to give 1.1 g of compound [25].

The NMR spectra and the mass spectra were in accordance with the expected product [25].

NB: 1,4-bis(1-imidazolyl)butane syntesis

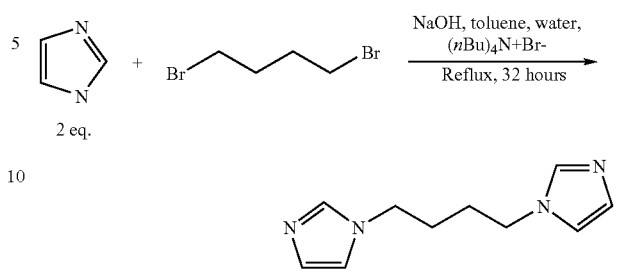

35.2 g of imidazole (0.52 mol), 54 g of 1,4-dibromobutane (0.26 mol), 100 g of sodium hydroxide (2.5 mol), 5.15 g of tetrabutylammonium bromide (0.016 mol) in 240 ml of toluene and 100 ml of water were stirred at reflux for 32 hours, in a round-bottomed flask surmounted by a condenser. After cooling, a product crystallizes. This product was filtered off and recrystallized from 200 ml of water. After drying under an active vacuum, 48 g of a beige powder corresponding to the compound were obtained.

The NMR spectra and the mass spectra were in accordance with the structure of the expected compound.

Example 7

Synthesis of Compound [27]

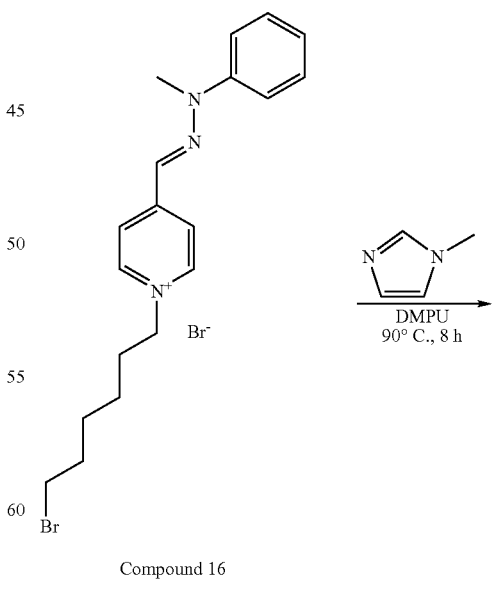

Compound 16

71
-continued

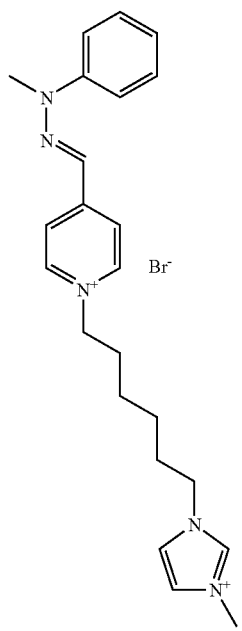

Compound 27

The intermediate [16] (2 g, 3.7 mmol) and 1-methylimidazole (0.7 g, 3.7 mmol) solubilized in 10 ml of DMPU were stirred at 90° C. in a 250 ml three-necked flask equipped with a thermometer and surmounted by a condenser. After 8 hours at 90° C., the reaction mixture was cooled and then poured over a solution of ethyl acetate; a precipitate appeared. This precipitate was then filtered off, solubilized with a small amount of methanol and again precipitated by adding ethyl acetate. The precipitate was then filtered off, and then dried under vacuum to give 2.5 g of compound [27].

The NMR spectra and the mass spectra were in accordance with the expected product [27].

72

Example 8

Synthesis of Compound [28]: 1-(6-{3-[4-(3-methyl-1H-imidazol-3-ium-1-yl)butyl]-1H-imidazol-3-ium-1-yl}hexyl)-4-{(E) [methyl(phenyl)hydrazono]methyl}quinolinium dibromide and 4-methylbenzenesulfonate

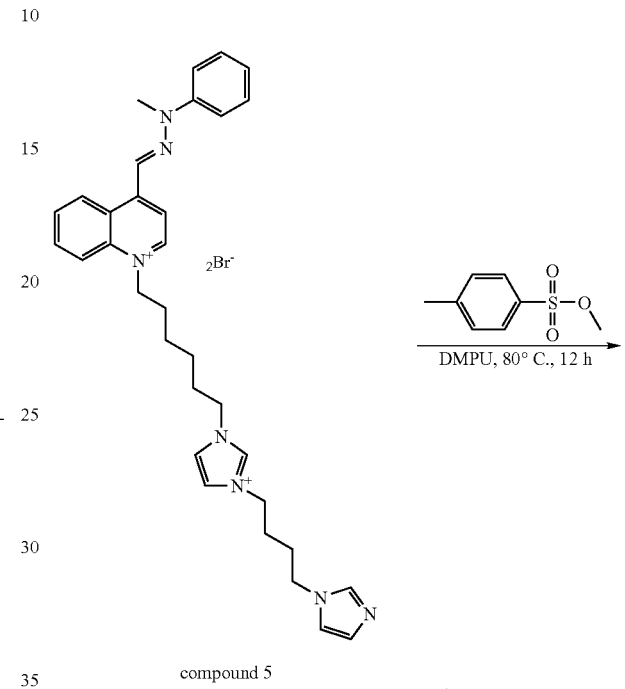

compound 5

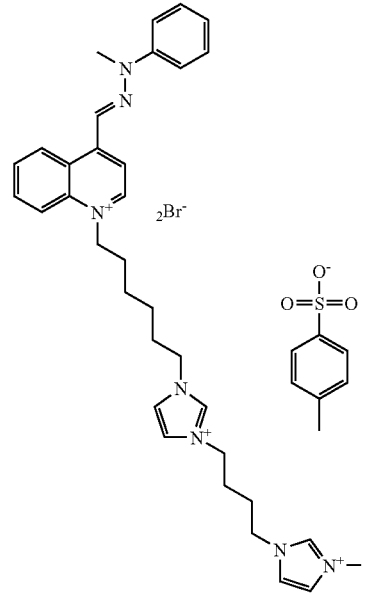

compound 28

In a 50 ml three-necked flask equipped with a thermometer and surmounted by a condenser, the intermediate [5] (0.123 g, 0.2 mmole), methyl p-toluene sulfonate (0.149 g, 0.8 mmole) were solubilized in 1.5 ml of DMPU and stirred at 80° C.

After 12 hours at 80° C., the mixture was cooled and poured over ethyl acetate; a viscous orange oil appeared. The oil was washed 2 times with ethyl acetate and dried under vacuum to give 0.097 g of compound [28].

The NMR spectra and the mass spectra were in accordance with the expected product [28].

Example 9

Synthesis of Compound [29]: 4-{(E)-[methyl(phenyl)hydrazono]methyl}-1-{6-[3-(4-{3-[3-(trimethylsilyl)propyl]-1H-imidazol-3-ium-1-yl}butyl)-1H-imidazol-3-ium-1-yl]hexyl}quinolinium dibromide and chloride

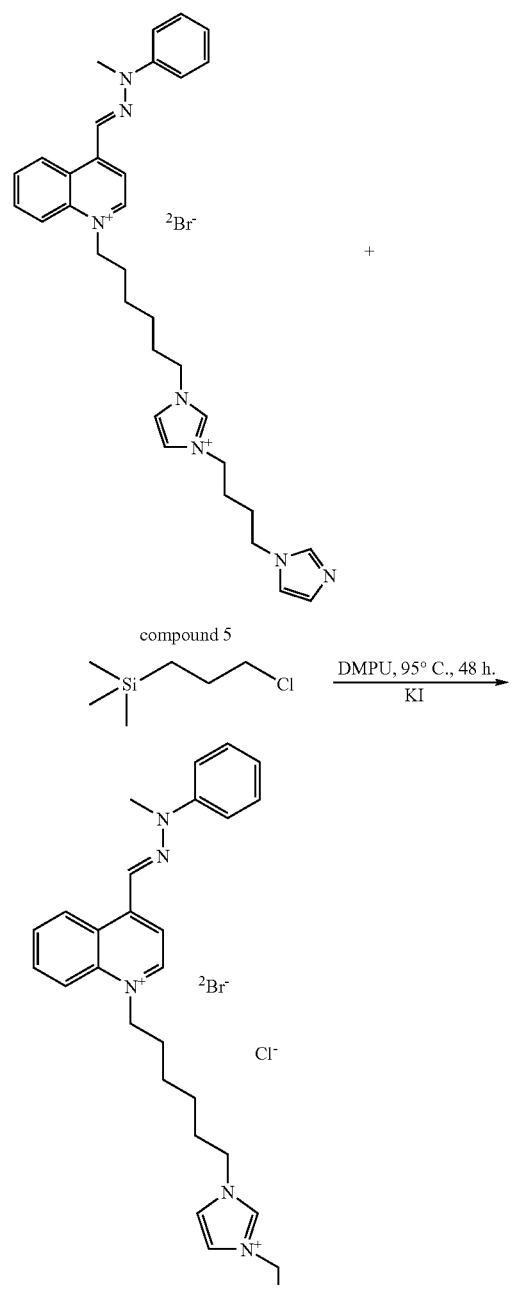

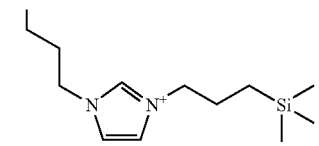

compound 29

In a 50 ml three-necked flask equipped with a thermometer and surmounted by a condenser, intermediate [5] (0.123 g, 0.2 mmole), (3-chloropropyl)(trimethyl)silane g, 0.8 mmole) and a catalytic quantity of potassium iodide were solubilized in 1.5 ml of DMPU and stirred at 95° C.

After 48 hours at 95° C., the mixture was cooled and poured over ethyl acetate. A viscous orange oil appeared which was purified by alumina column chromatography, giving 0.081 g of compound [29].

The NMR spectra and the mass spectra were in accordance with the expected product [29].

Example 10

Synthesis of Compound [31]: 1-[6-(3-methyl-1H-imidazol-3-ium-1-yl)hexyl]-2-{(E)-[methyl(phenyl)hydrazono]methyl}pyridinium bromide and 4-methylbenzenesulfonate

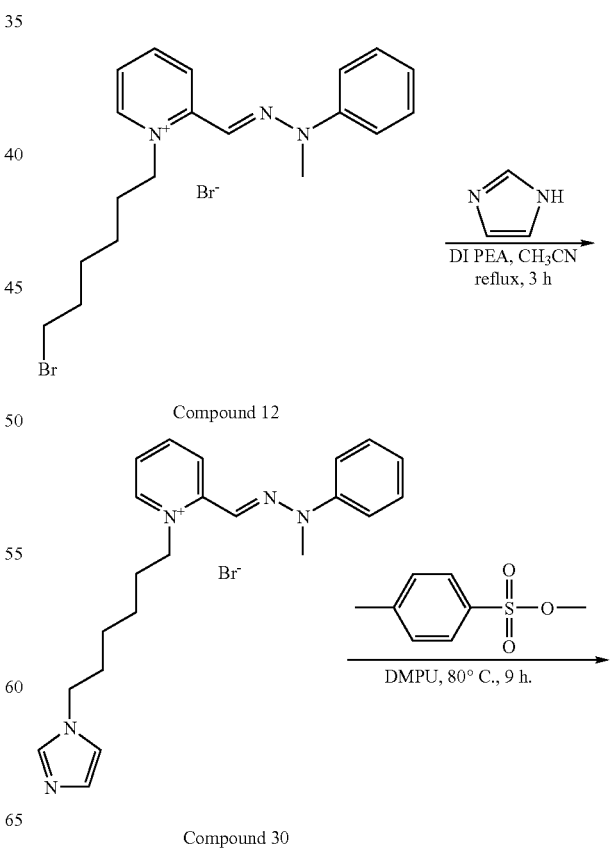

Compound 30

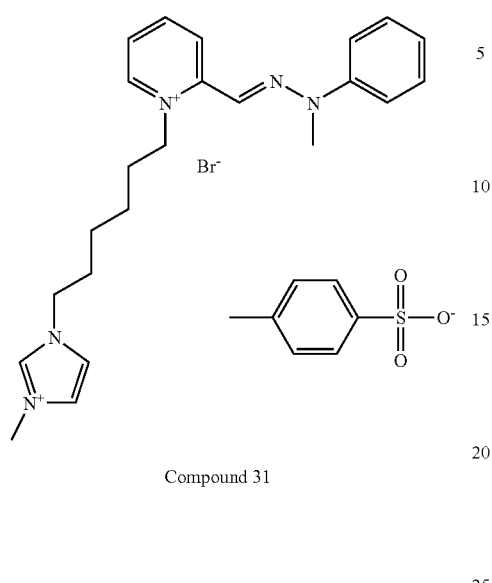

Compound 31

Stage 1

In a 25 ml three-necked flask equipped with a thermometer and surmounted by a condenser, intermediate [12] (2.27 g, 5 mmoles), imidazole (3.40 g, 50 mmoles) were stirred in 30 ml of acetonitrile and 11.4 g of diisopropylethylamine.

After 3 hours reflux, the reaction medium was cooled; the solvent was evaporated and the obtained residue was chromatographed (THF/MeOH: 4:1), resulting in 2.0 g of compound [30] and some impurities.

The product was then suspended in 80 ml of ethyl acetate and 2 ml of methanol. After 12 hours of being stirred at ambient temperature, a yellow powder was filtrated and dried under vacuum to give 1.6 g of a yellow powder corresponding to compound [30].

The NMR spectra and the mass spectra were in accordance with the expected product [30].

Stage 2

In a 50 ml three-necked flask equipped with a thermometer and surmounted by a condenser, intermediate [30] (0.089 g, 0.2 mmole), methyl p-toluene sulfonate (0.149 g, 0.8 mmole) were solubilized in 1.5 ml of DMPU and stirred at 80° C.

After 9 hours at 80° C., the reaction medium was cooled and poured over ethyl acetate; a viscous yellow oil appeared which was washed 2 times with ethyl acetate. The obtained yellow oil was then dried under vacuum to give 0.061 g of compound [31].

The NMR spectra and the mass spectra were in accordance with the expected product [31].

Example 11

Synthesis of Compound [32]: 2-{(E)-[methyl(phenyl)hydrazono]methyl}-1-(6-{3-[3-(trimethylsilyl)propyl]-1H-imidazol-3-ium-1-yl}hexyl)pyridinium bromide and chloride

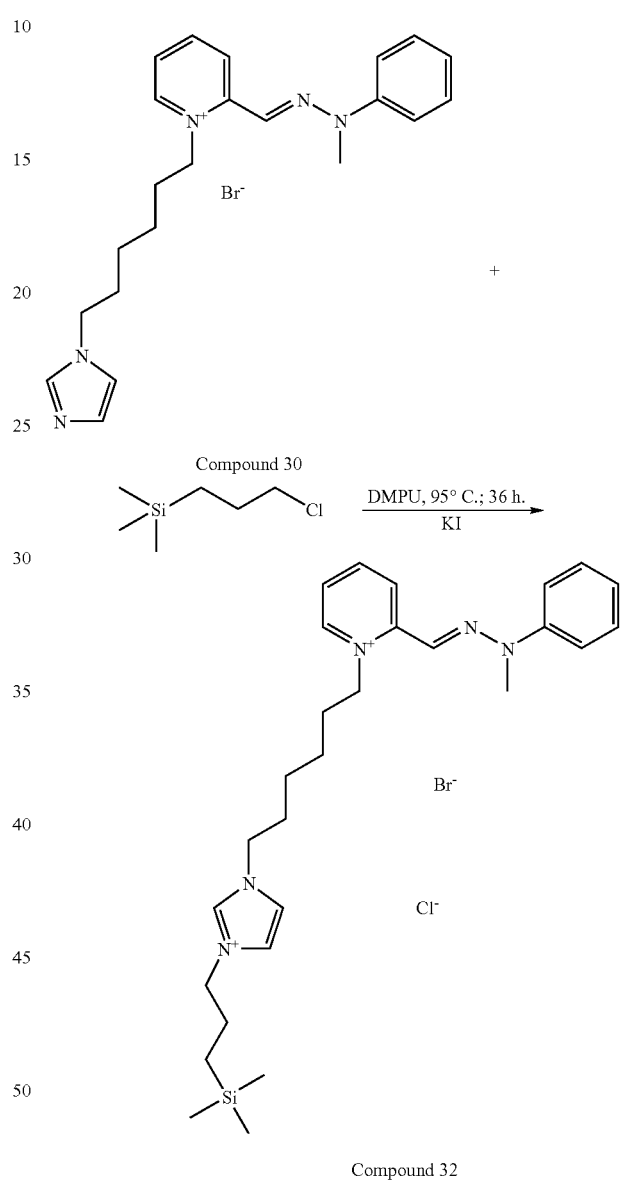

In a 50 ml three-necked flask, equipped with a thermometer and surmounted by a condenser, compound [30] (0.088 g, 0.2 mmole), (3-chloropropyl)(trimethyl)silane (0.121 g, 0.8 mmole) and a catalytic quantity of potassium iodide were solubilized in 1.5 ml of DMPU and stirred at 95° C.

After 36 hours at 95° C., the reaction medium was cooled and poured over ethyl acetate. A solid residue appears, which was filtrated under vacuum, then washed 2 times with ethyl acetate and dried under vacuum to give 0.074 g of a yellow powder corresponding to compound [32].

The NMR spectra and the mass spectra are in accordance with the expected product [32].

Example 12

Synthesis of Compound [34]: 1-methyl-3-[6-(3-methyl-1H-imidazol-3-ium-1-yl)hexyl]-2-{(E)-[methyl(phenyl)hydrazono]methyl}-1H-3,1-benzimidazol-3-ium chloride and 4-methylbenzenesulfonate

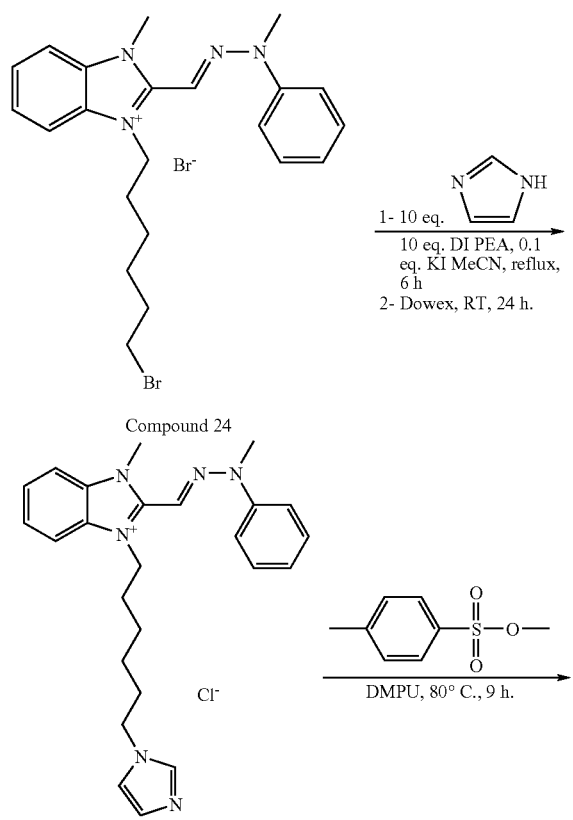

Stage 1

In a 250 ml three-necked flask, equipped with a thermometer and surmounted by a condenser, compound [24] (2.03 g, 4 mmoles), imidazole (2.72 g, 40 mmoles) were mixed with 30 ml of acetonitrile, 7 ml of diisopropylethylamine and a catalytical quantity of potassium iodide (67 mg, 0.4 mmole).

After 6 hours reflux, the reaction medium was cooled and poured over 300 ml of ethyl acetate. The resulting precipitate was filtrated, washed with ethyl acetate and finally dried under vacuum giving 1.8 g of a yellow powder.

The powder was then solubilized in 30 ml of methanol with 34 g of a DOWEX anion exchange resin. The resulting mixture was then stirred at ambient temperature during 24 hours.

The mixture was then filtered and the reaction medium was concentrated under vacuum. The resulting solid was purified by silica gel chromatography resulting in 0.86 g of compound [33] (yellow solid).

The NMR spectra and the mass spectra were in accordance with the expected product [33].

Stage 2

In a 50 ml three-necked flask equipped with a thermometer and surmounted by a condenser, compound [33] (0.099 g, 0.2 mmole), methyl p-toluene sulfonate (0.149 g, 0.8 mmole) were solubilized in 1.5 ml of DMPU and stirred at 80° C.

After 9 hours at 80° C., the reaction medium was cooled and poured over ethyl acetate. A viscous yellow oil appeared which was washed 2 times with ethyl acetate. The yellow oil was then dried under vacuum resulting in 0.065 g of compound [34].

The NMR spectra and the mass spectra are in accordance with the expected product [34].

Example 13

Synthesis of Compound [35]: 1-methyl-2-{(E)-[methyl(phenyl) hydrazono]methyl}-3-(6-{3-[3-(trimethylsilyl) propyl]-1H-imidazol-3-ium-1-yl}hexyl)-1H-3,1-benzimidazol-3-ium dichloride

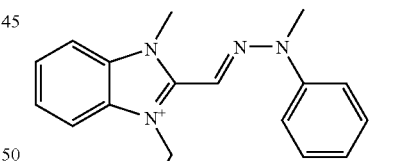

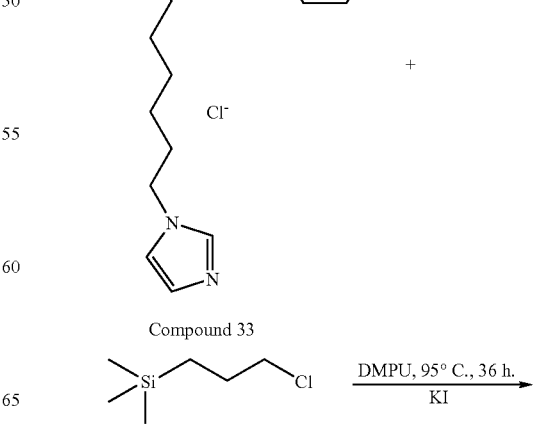

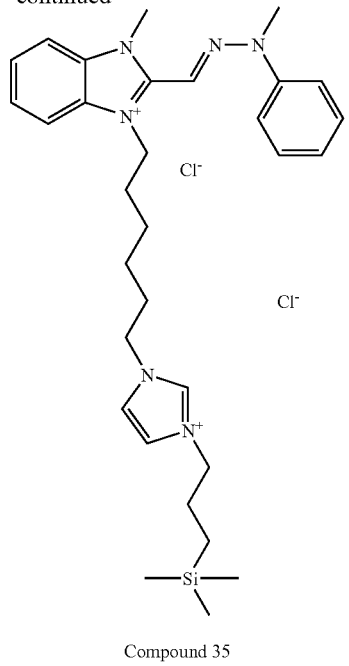

Compound 35

In a 50 ml three-necked flask equipped with a thermometer and surmounted with a condenser, compound [33] (0.099 g, 0.2 mmole), (3-chloropropyl)(trimethyl)silane (0.121 g, 0.8 mmole) and a catalytic quantity of potassium iodide were solubilized in 1.5 ml of DMPU and stirred.

After 36 hours at 95° C., the reaction medium was cooled and poured over ethyl acetate. A yellow precipitate appeared which was filtrated under vacuum, washed 2 times with ethyl acetate and then dried under vacuum to give 0.087 g of a yellow powder corresponding to compound [35].

The NMR spectra and the mass spectra were in accordance with the expected product [35].

Example 14

Examples of Dyeing

The dyeing compositions were prepared according to the following proportions:

| Solution 1 | |
| --- | --- |
| Alkyl (C8/C10 50/50) polyglucoside (2) in a 60% aqueous solution | 120 g |
| Ethanol | 200 g |
| Polyethylene glycol(8 EO) 400 | 60 g |
| Benzyl alcohol | 40 g |
| Demineralized water | qsp 1000 g |

| Solution 2: Buffer pH 9.5 | |
| --- | --- |
| Ammonium chloride ($NH_4Cl$) | 54 g |
| Ammonia (20% aqueous solution) | qsp pH = 9.5 (approx. 40 ml) |
| Demineralized water | qsp 1000 ml |

| Solution 3: Buffer pH 7 | |
| --- | --- |
| $KH_2PO_4$ | 0.026 mol/l |
| $Na_2PO_4$ | 0.041 mol/l |
| Demineralized water | qsp 500 ml |

The dyeing compositions were obtained by solubilizing the direct dye mentioned below ($5 \times 10^{-3}$ mol/l) in solution 1 and by adding an equivalent volume of solution 2 or 3 (pH7 or pH 9.5).

Each composition was applied onto locks of natural hair with 90% of white hair (1 g of hair for 6 g of solution).

After 30 minutes at ambient temperature, the locks of hair were rinsed, washed with a standard shampoo, rinsed again and dried.

The results are shown in the table below:

| | pH 7 | pH 9.5 |
| --- | --- | --- |
| (Compound I structure) | Yellow chromatic | Yellow chromatic |
| Compound I: Basic Yellow 87 (not according to the invention) | | |
| Compound 5 | Orange chromatic intense | Orange chromatic intense |
| Compound 9 | Reddish yellow chromatic intense | Reddish yellow chromatique intense |
| Compound 13 | Yellow | Yellow |
| Compound 17 | Yellow chromatic intense | Yellow chromatic Intense |
| Compound 21 | Light yellow | Light yellow |
| Compound 25 | Yellow | Yellow |
| Compound 27 | Yellow chromatic intense | Yellow chromatic intense |
| Compound 28 | Orange chromatic intense | Orange chromatic intense |
| Compound 29 | Orange chromatic intense | Orange chromatic intense |
| Compound 31 | Yellow | Yellow |
| Compound 32 | Light yellow | Light yellow |
| Compound 34 | Light yellow | Light yellow |
| Compound 35 | Light yellow | Light yellow |

Comparative Experiments

The color of the locks hair obtained by compound I (Basic Yellow 87 not according to the invention) and by compound 27 was measured by using a spectrophotometer CM 2002 MINOLTA®, (Illuminant D65).

Chromaticity was calculated according to the following formula:

$$C^* = [a^{*2} + b^{*2}]^{1/2}$$

The higher the value of C*, the more chromatic the resulting the color.

The dye uptake was also calculated, using the following formula:

$$DE^* = [(L^*_0 - L^*_1)^2 + (a^*_0 - a^*_1)^2 + (b^*_0 - b^*_1)^2]^{1/2}$$

wherein $L^*_0$, $a^*_0$ et $b^*_0$ correspond to the coefficients of the undyed hair and $L^*_1$, $a^*_1$, et $b^*_1$ correspond to the coefficients of the dyed hair. The higher the value of DE*, the higher the uptake of the dye.

The following results were obtained:

|  | pH | C* | DE * |
|---|---|---|---|
| Compound I | 7 | 40.25 | 30.5 |
| Compound 27 | 7 | 59 | 45.5 |
| Compound I | 9.5 | 35.6 | 26.05 |
| compound 27 | 9.5 | 48.4 | 35.35 |

The color obtained with compound 27 was significantly more chromatic and the uptake of the dye higher than in the case of the color obtained from compound I, for both values of pH.

Then, the locks of hair were submitted to a test of shampoo fastness comprising carrying out 10 shampoos (washing and rinsing).

The resulting color was then measured in the L*a*b* system, as previously described.

The results are given below:

|  | After 10 shampoos (% of loss of color) |
|---|---|
| Compound I | 20-30 |
| Compound 27 | 0-10 |

What is claimed is:

1. At least one polycationic hydrazone entity chosen from compounds of formula (I), tautomeric forms thereof, acid-addition salts thereof and solvates thereof:

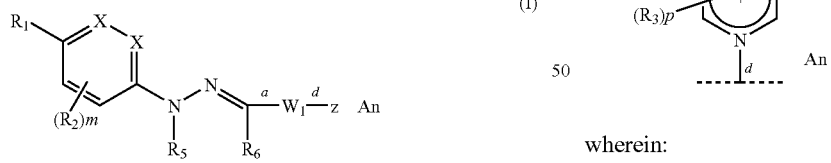

(I)

wherein:

$W_1$ is a heteroaromatic radical of following formulae (1) to (8):

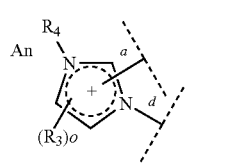

(1)

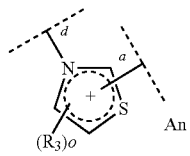

(2)

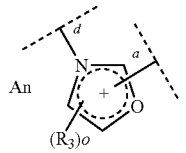

(3)

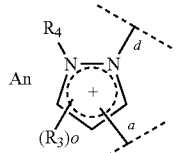

(4)

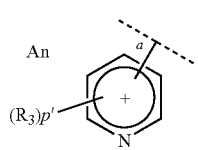

(5)

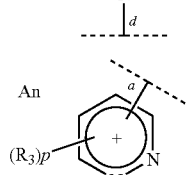

(6)

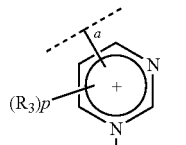

(7)

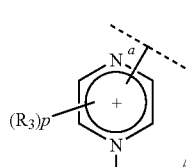

(8)

wherein:
the radical $R_1$ is chosen from:
a hydrogen;
an optionally substituted $C_1$-$C_{20}$ alkyl radical, optionally interrupted with at least one heteroatom and/or with at least one group comprising at least one heteroatom, wherein the alkyl radical does not comprise any nitro, nitroso, peroxo or diazo function;
an alkylcarbonyl radical (R—CO—) wherein R is a $C_1$-$C_4$ alkyl radical;
an alkylsulphonyl radical (RSO$_2$—) wherein R is a $C_1$-$C_4$ alkyl radical;
an arylsulphonyl radical (R'SO$_2$—) wherein R' is an optionally substituted phenyl or benzyl radical;

a (di)(alkyl)aminosulphonyl radical ((R)$_2$N—SO$_2$—) wherein the R radicals independently are chosen from a hydrogen and a C$_1$-C$_4$ alkyl radical;

a (di)(alkyl)aminocarbonyl radical ((R)$_2$N—CO—) wherein the R radicals independently are chosen from a hydrogen and a C$_1$-C$_4$ alkyl radical;

a halogen atom;

a hydroxyl group;

a C$_1$-C$_4$ alkoxy group;

a C$_2$-C$_4$ (poly)hydroxyalkoxy group;

a hydroxycarbonyl group;

an alkoxycarbonyl group (RO—CO—) wherein R is a C$_1$-C$_4$ alkyl radical;

an alkylcarbonyloxy radical (RCO—O—) wherein R is a C$_1$-C$_4$ alkyl radical;

an optionally substituted aryloxy group;

an NR$_7$R$_8$ group wherein R$_7$ and R$_8$ are chosen from, independently of one another:
  a hydrogen atom;
  a C$_1$-C$_4$ alkyl radical, optionally carrying at least one hydroxyl or C$_1$-C$_2$ alkoxy group, it being possible for said alkyl radicals to optionally form, with the nitrogen atom to which they are attached, a saturated or unsaturated, optionally substituted, optionally aromatic heterocycle containing from 5 to 7 ring members, optionally comprising another heteroatom which may be identical to or different from nitrogen;
  a phenyl radical; an aminophenyl radical; a 4-N,N-diethylaminophenyl radical; a methoxyphenyl radical;

an alkylcarbonylamino group (RCO—NR'—) wherein the R radical is a C$_1$-C$_4$ alkyl radical and the R' radical is chosen from a hydrogen atom and a C$_1$-C$_4$ alkyl radical;

a ureido group (N(R)$_2$—CO—NR'—) wherein the R and R' radicals, independently of one another, are chosen from a hydrogen atom and C$_1$-C$_4$ alkyl radicals;

an alkylthio group (R—S—) wherein the R group is a C$_1$-C$_4$ alkyl radical;

an alkylsulphonylamino group (RSO$_2$—NR'—) wherein the R' radical is chosen from a hydrogen atom and a C$_1$-C$_4$ alkyl radical, and the R radical is a C$_1$-C$_4$ alkyl radical;

a cyano group; and a trifluoromethyl group (CF$_3$);

The radicals R$_2$ and R$_3$, which may be identical or different, are chosen from, independently of one another:
  a halogen atom;
  an optionally substituted C$_1$-C$_{16}$ alkyl radical, optionally interrupted with at least one heteroatom and/or with at least one group comprising at least one heteroatom; wherein the alkyl radical does not comprise any nitro, nitroso, peroxo or diazo functions;
  a hydroxyl radical;
  a C$_1$-C$_4$ alkoxy radical;
  a C$_2$-C$_4$ (poly)hydroxyalkoxy group;
  a hydroxycarbonyl radical;
  an alkoxycarbonyl radical (RO—CO—) wherein R is a C$_1$-C$_4$ alkyl radical;
  an alkylcarbonyloxy radical (RCO—O) wherein R is a C$_1$-C$_4$ alkyl radical;
  an optionally substituted aryloxy radical;
  an optionally substituted arylamino radical;
  an amino radical optionally substituted with one or two C$_1$-C$_4$ alkyl radicals, which may be identical or different, optionally carrying at least one hydroxyl or C$_1$-C$_2$ alkoxy group, it being possible for said alkyl radicals to optionally form, with the nitrogen atom to which they are attached, a saturated or unsaturated, optionally substituted, optionally aromatic heterocycle containing from 5 to 7 ring members, optionally comprising another heteroatom which may be identical to or different from nitrogen;
  an alkylcarbonylamino radical (RCO—NR'—) wherein the R radical is a C$_1$-C$_4$ alkyl radical and the R' radical is chosen from a hydrogen and a C$_1$-C$_4$ alkyl radical;
  a (di)(alkyl)aminocarbonyl group ((R)$_2$N—CO—) wherein the R radicals, independently of one another, are chosen from a hydrogen and a C$_1$-C$_4$ alkyl radical;
  a ureido radical (N(R)$_2$—CO—NR'—) wherein the R radicals, independently of one another, are chosen from C$_1$-C$_4$ alkyl radicals, and R' is chosen from a hydrogen and a C$_1$-C$_4$ alkyl radical;
  a (di)(alkyl)aminosulphonyl radical ((R)$_2$N—SO$_2$—) wherein the R radical is chosen from a hydrogen atom and a C$_1$-C$_4$ alkyl radical;
  an alkylthio radical (R—S—) wherein the R radical is a C$_1$-C$_4$ alkyl radical;
  an alkylsulphonylamino radical (RSO$_2$—NR'—) wherein the R radical is a C$_1$-C$_4$ alkyl radical, and the R' radical is chosen from a hydrogen atom and a C$_1$-C$_4$ alkyl radical;
  an alkylsulphonyl radical (RSO$_2$—) wherein the R radical is a C$_1$-C$_4$ alkyl radical;
  a cyano radical (—CN); and
  a trifluoromethyl radical (CF$_3$);

Two adjacent radicals R$_2$ can form, with one another and with the carbon atoms to which they are attached, a substituted or unsubstituted, aromatic or nonaromatic (hetero)cyclic radical comprising 5 or 6 ring members;

One of the radicals R$_7$ or R$_8$ can form, with the nitrogen atom to which it is attached and with a radical R$_2$ located in the ortho-position with respect to the NR$_7$R$_8$ group, a substituted or unsubstituted, saturated or unsaturated heterocycle comprising 5 or 6 ring members;

The radicals R$_7$ and R$_8$ can form, with the nitrogen atom to which they are attached and each with a radical R$_2$ located in the ortho-position with respect to the NR$_7$R$_8$ group, a substituted or unsubstituted, saturated or unsaturated heterocycle comprising 5 or 6 ring members;

m is an integer ranging from 0 to 4; when m is less than 4, the unsubstituted carbon atom(s) carries a hydrogen atom;

X, independently of one another, is N or CR$_2$;

o is an integer ranging from 0 to 2; when o is less than 2, the unsubstituted carbon atom(s) carries a hydrogen atom;

Two adjacent radicals R$_3$ can form, with one another and with the carbon atoms to which they are attached, a substituted or unsubstituted aromatic ring comprising 6 ring members;

The radicals R$_4$, which may be identical or different, are chosen from:
  an optionally substituted C$_1$-C$_{20}$ alkyl radical, optionally interrupted with at least one heteroatom and/or with at least one group comprising at least one heteroatom, wherein the alkyl radical does not comprise any nitro, nitroso, peroxo or diazo function;
  a C$_1$-C$_4$ trimethylsilylalkyl radical;
  an optionally substituted phenyl radical; and
  an optionally substituted benzyl radical;

The radical $R_5$ is chosen from:
- a hydrogen;
- an optionally substituted $C_1$-$C_{20}$ alkyl radical, optionally interrupted with at least one heteroatom and/or with at least one group comprising at least one heteroatom, wherein the alkyl radical does not comprise any nitro, nitroso, peroxo or diazo function;
- an optionally substituted phenyl radical;
- an optionally substituted benzyl radical;
- an alkylcarbonyl radical (R—CO—) wherein R is a $C_1$-$C_4$ alkyl radical;
- an alkylsulphonyl radical ($RSO_2$—) wherein R is a $C_1$-$C_4$ alkyl radical;
- an arylsulphonyl radical ($R'SO_2$—) wherein R' is an optionally substituted phenyl or benzyl radical;
- a (di)(alkyl)aminosulphonyl radical (($R)_2N$—$SO_2$—) wherein the R radicals are independently chosen from a hydrogen and a $C_1$-$C_4$ alkyl radical; and
- a (di)(alkyl)aminocarbonyl radical (($R)_2N$—CO—) wherein the R radicals are independently chosen from a hydrogen and a $C_1$-$C_4$ alkyl radical;

$R_5$ can form, with a radical $R_2$ located in the ortho-position with respect to the $NR_5$ group and with the nitrogen atom substituted with $R_5$, a substituted or unsubstituted, saturated or unsaturated heterocycle comprising 5 or 6 ring members;

The radical $R_6$ is chosen from:
- a hydrogen atom;
- an optionally substituted $C_1$-$C_{16}$ alkyl radical, optionally interrupted with at least one heteroatom and/or with at least one group comprising at least one heteroatom, wherein the alkyl radical does not comprise any nitro, nitroso, peroxo or diazo function;
- an amino radical optionally substituted with one or two $C_1$-$C_4$ alkyl radicals, which may be identical or different, optionally carrying at least one hydroxyl or $C_1$-$C_2$ alkoxy group, it being possible for said alkyl radicals to optionally form, with the nitrogen atom to which they are attached, an optionally substituted, saturated or unsaturated or aromatic heterocycle comprising 5 or 6 ring members, optionally comprising at least one other heteroatom which may be identical to or different from nitrogen;
- an alkylcarbonylamino radical (RCO—NR'—) wherein the R radical is a $C_1$-$C_4$ alkyl radical and the R' radical is chosen from a hydrogen and a $C_1$-$C_4$ alkyl radical;
- a ureido radical ($N(R)_2CO$—NR'—) wherein the R radicals, independently of one another, are chosen from a $C_1$-$C_4$ alkyl radical, and R' is chosen from a hydrogen and a $C_1$-$C_4$ alkyl radical;
- an alkylsulphonylamino radical ($RSO_2$—NR'—) wherein the R radical is a $C_1$-$C_4$ alkyl radical and the R' radical is chosen from a hydrogen and a $C_1$-$C_4$ alkyl radical;
- a hydroxycarbonyl radical (HOOC—);
- a $C_1$-$C_4$ alkoxycarbonyl radical (RO—CO—);
- an optionally substituted phenyl radical; and
- an optionally substituted benzyl radical;

p is an integer ranging from 0 to 3; p' is an integer ranging from 0 to 4; when p is less than 3, or p' is less than 4, the unsubstituted carbon atom(s) carries a hydrogen atom;

The bond a links the heteroaromatic radical $W_1$ to the carbon atom of the $CR_6$ group;

Z is a $C_2$-$C_{20}$ alkylene radical comprising at least one quaternized nitrogen atom;

the bond d links the cationic group(s) Z to a nitrogen atom of the heteroaromatic radical $W_1$;

the electroneutrality of the compounds of formula (I) being ensured by at least one cosmetically acceptable anion An or a mixture of cosmetically acceptable anions An, which may or may not be identical;

and the following compounds wherein, $R_1$, $R_2$, m, and An are as defined above, for which R is chosen from a hydrogen atom and a methyl radical:

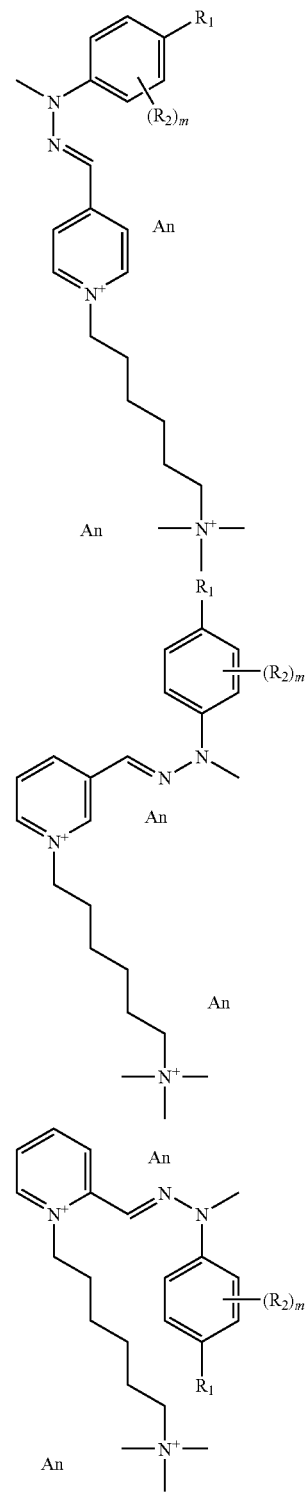

87
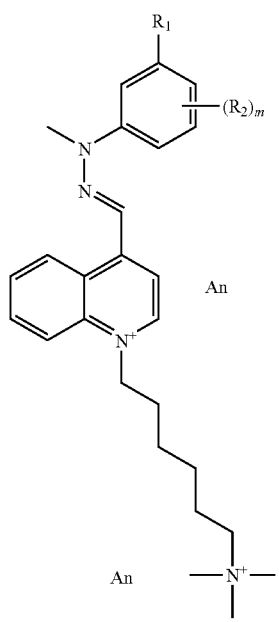
88
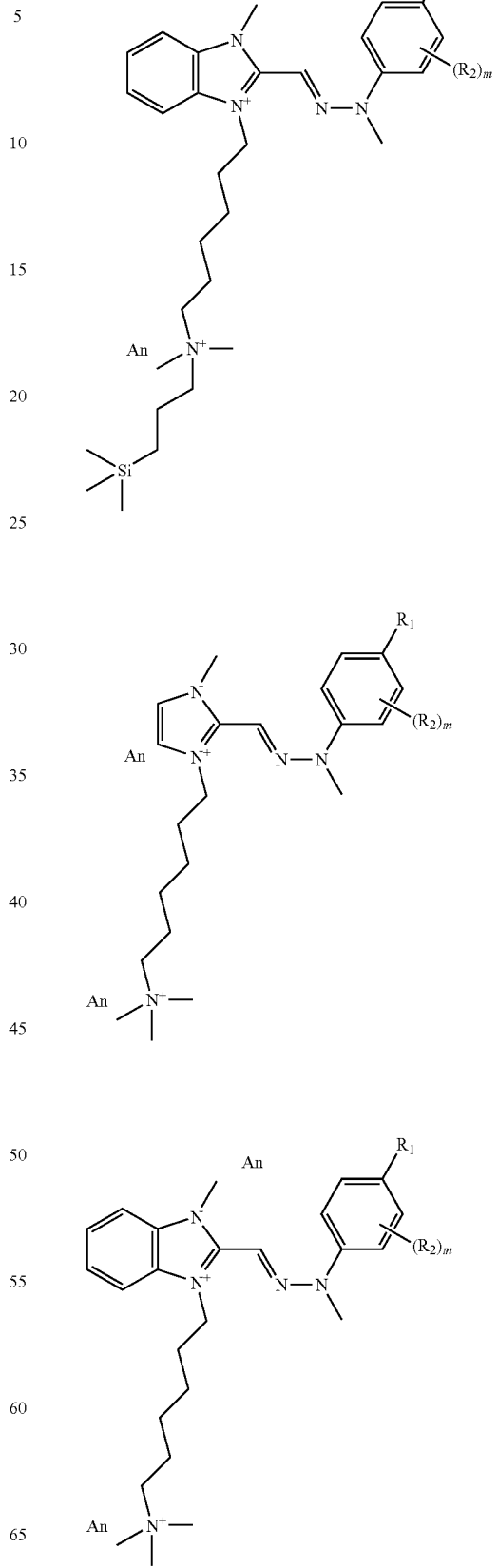

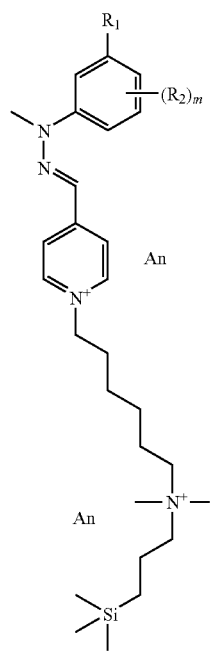
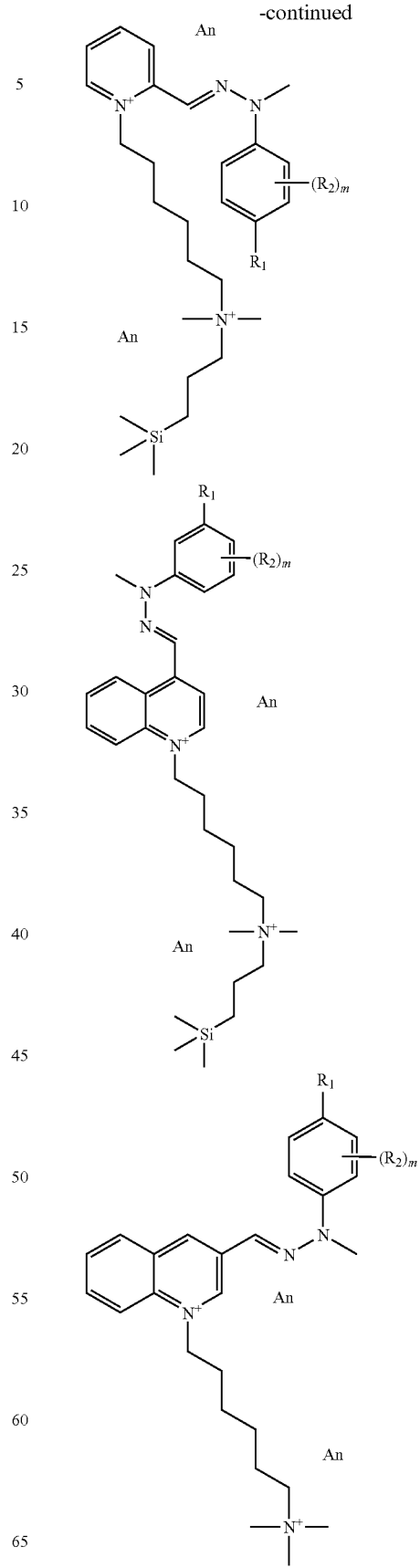

-continued
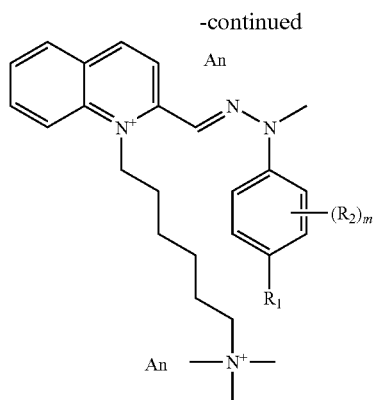
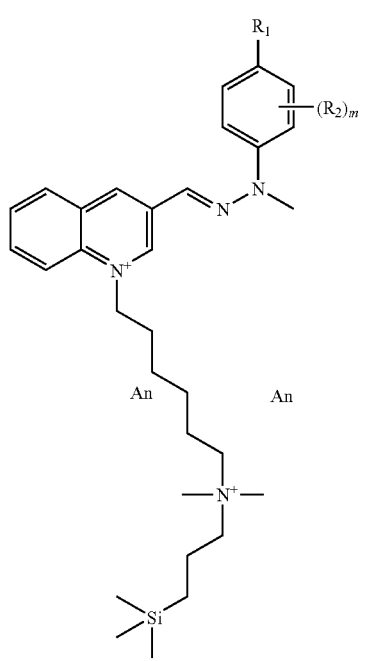
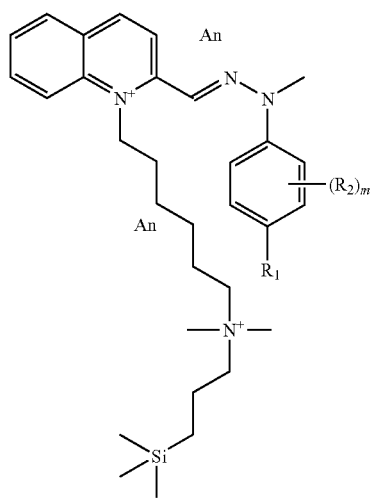
-continued
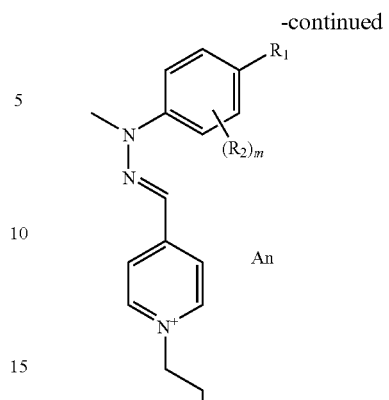
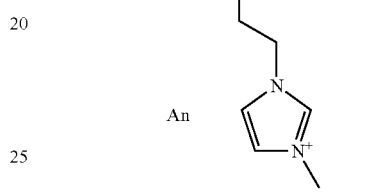
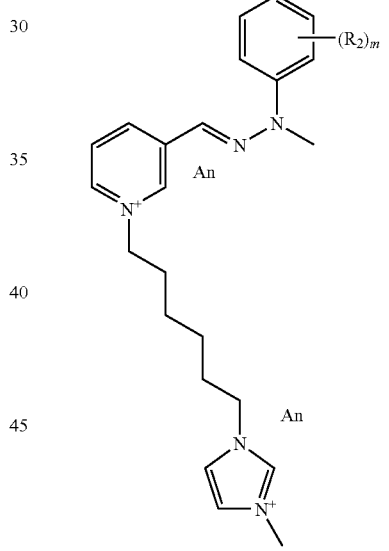
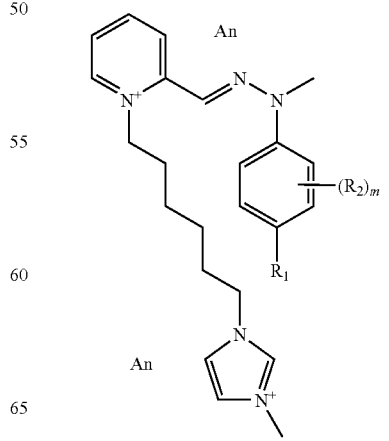

-continued
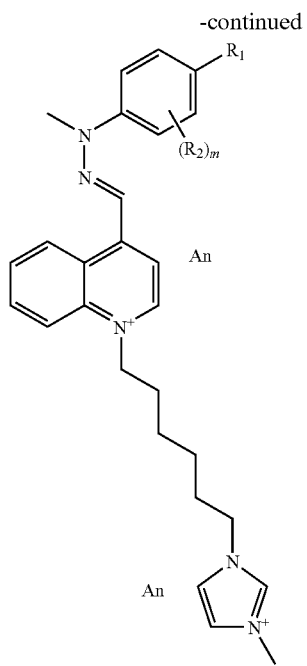
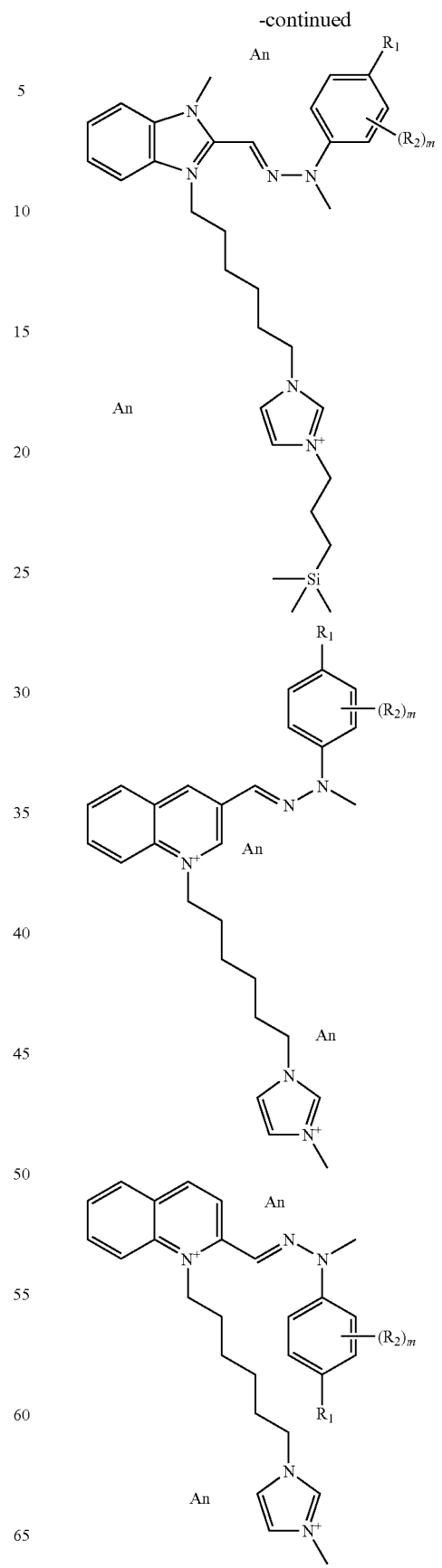

-continued
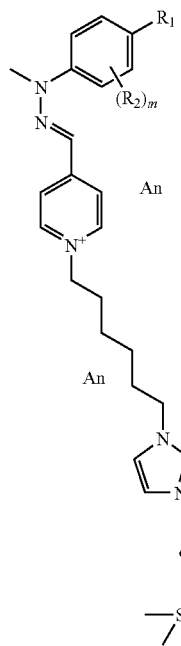
-continued
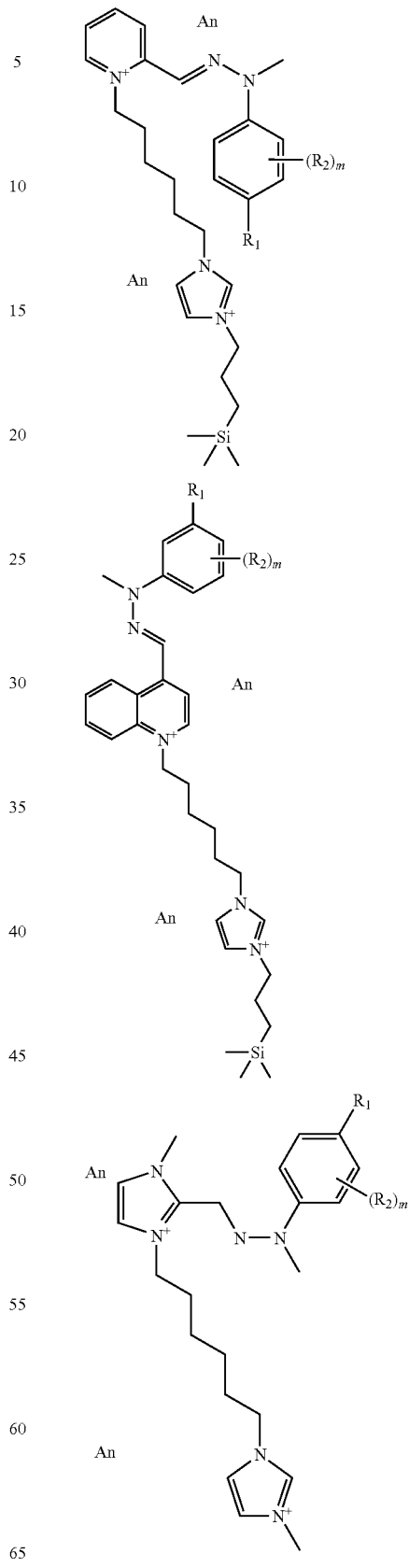

-continued
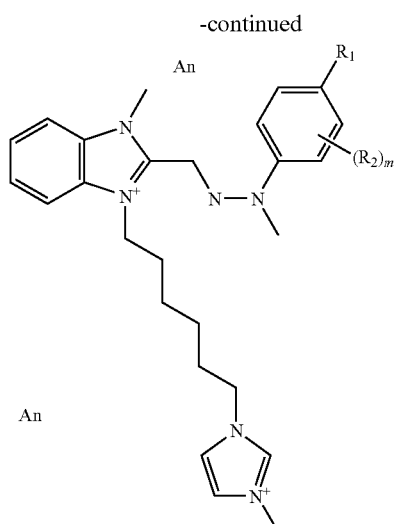
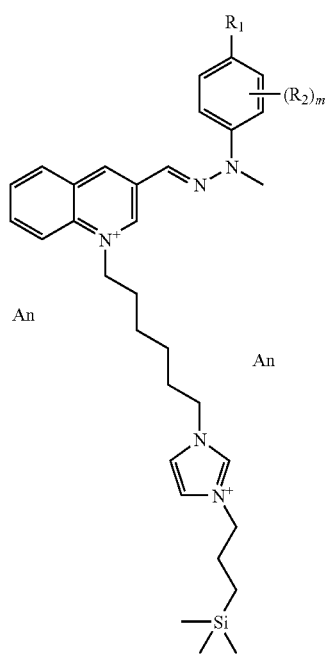
-continued
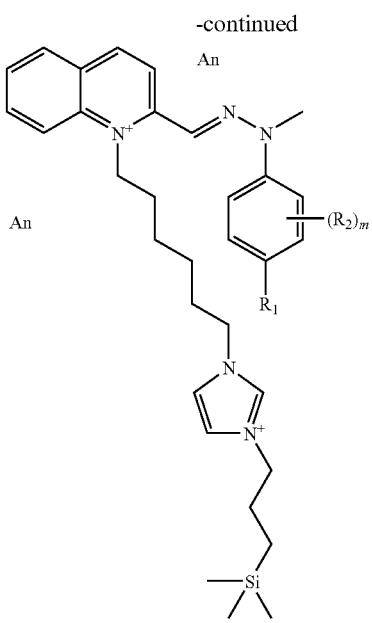

-continued
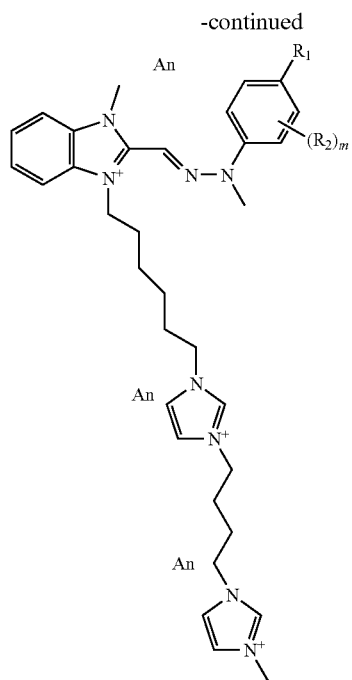
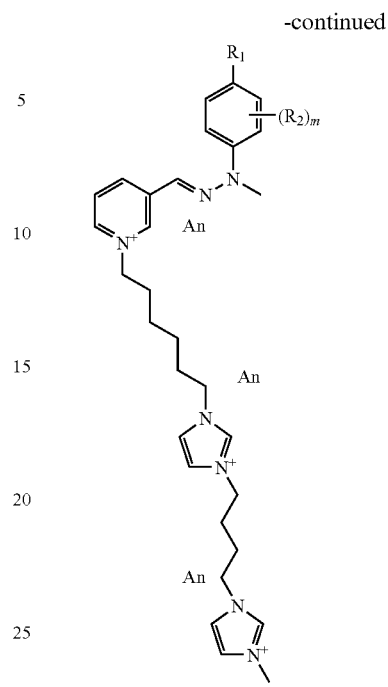
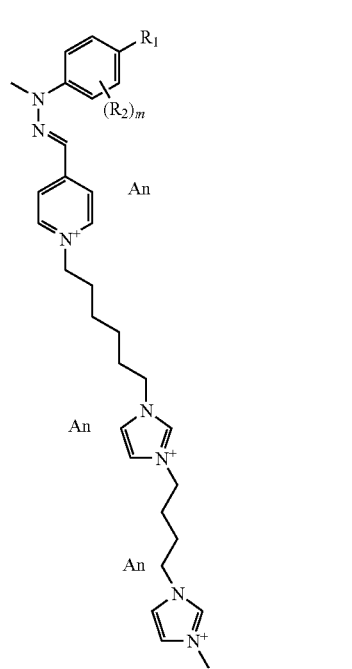
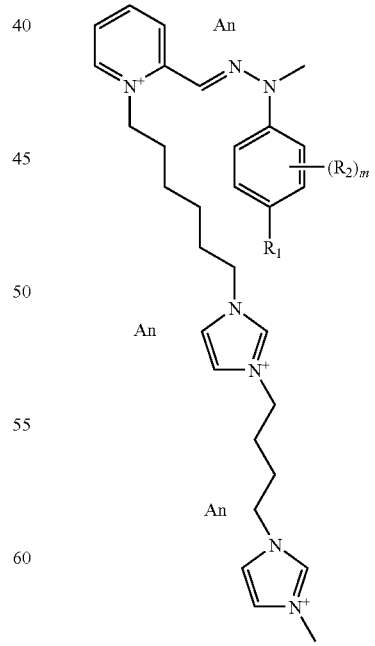

101
-continued
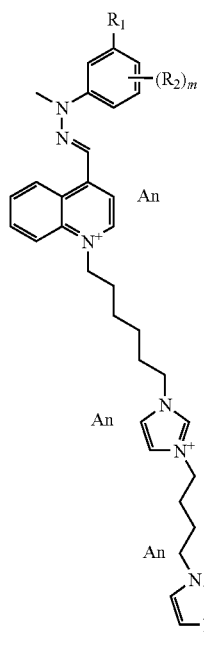
102
-continued
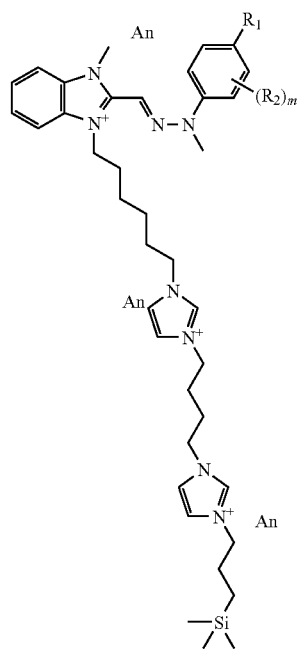
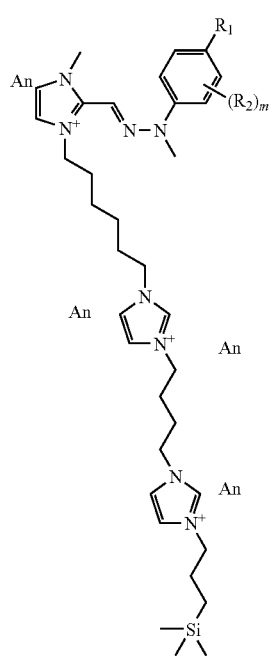
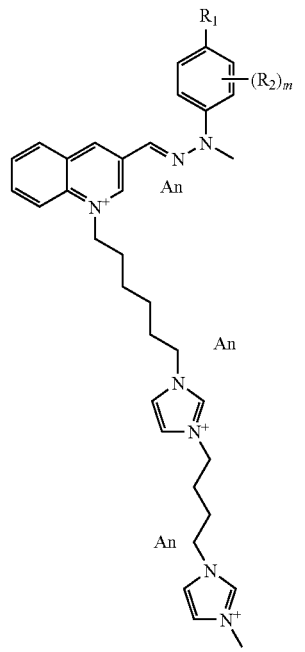

-continued
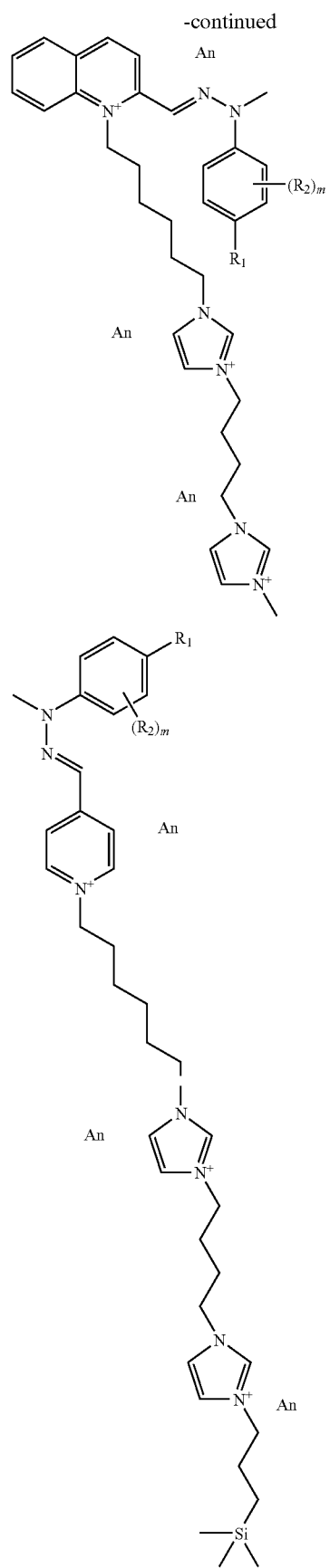
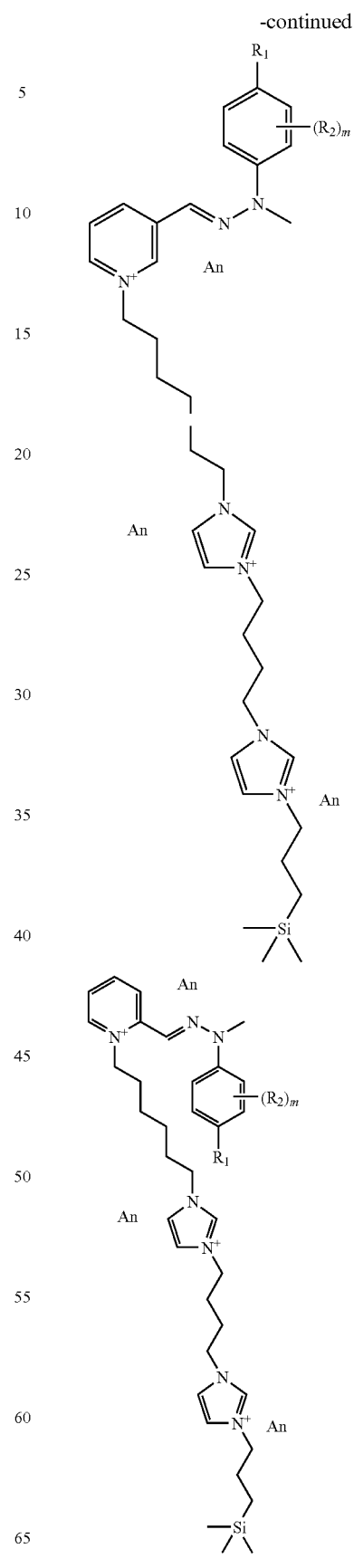

-continued
105
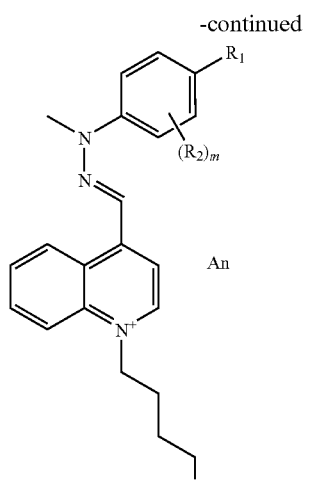
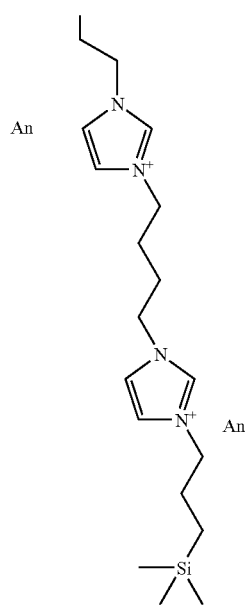
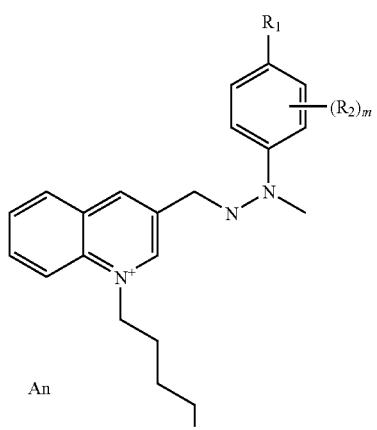
106
-continued
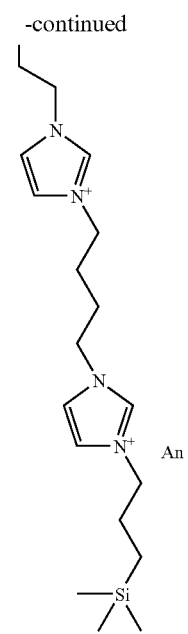
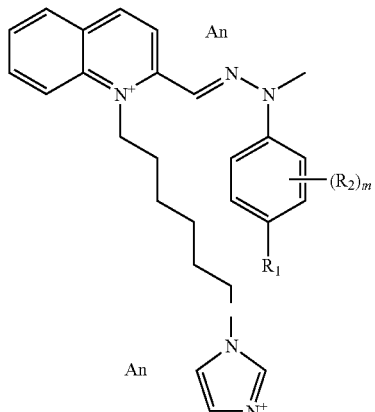
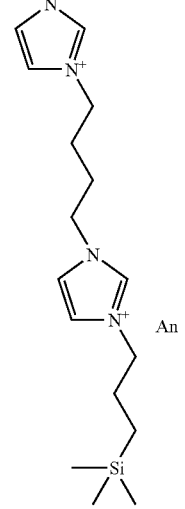

-continued
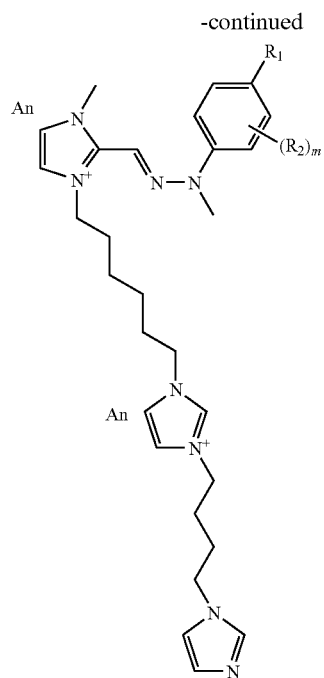
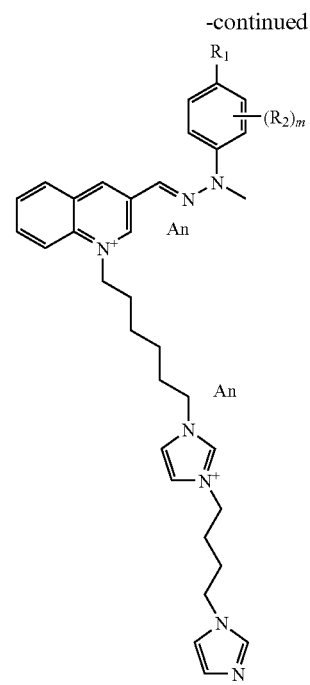
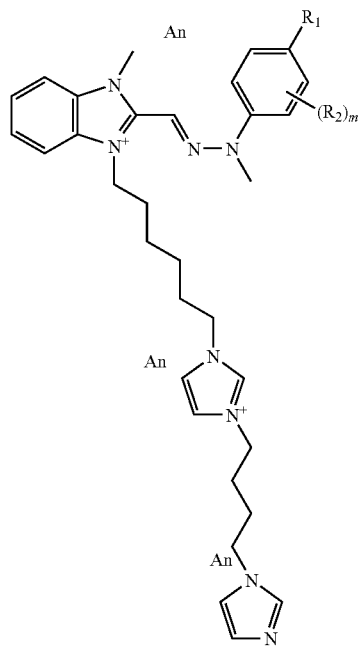
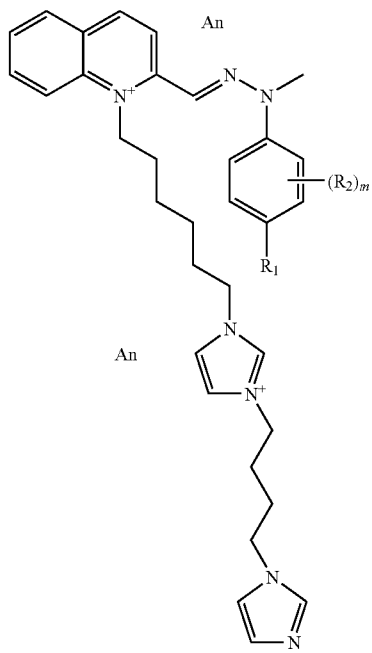

-continued

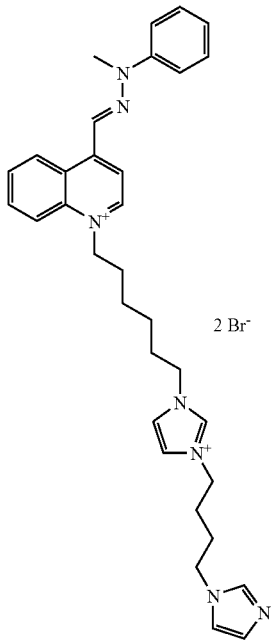

2 Br⁻

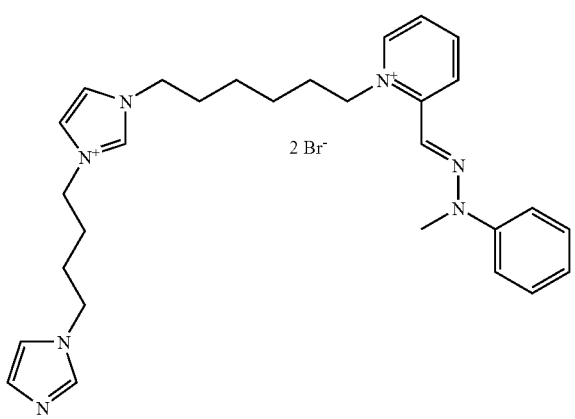

2 Br⁻

-continued

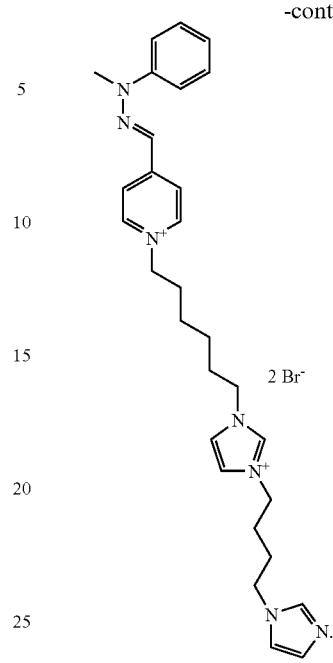

2 Br⁻

2. The at least one polycationic hydrazone entity according to claim 1, wherein $W_1$ is a heteroaromatic radical of formulae below:

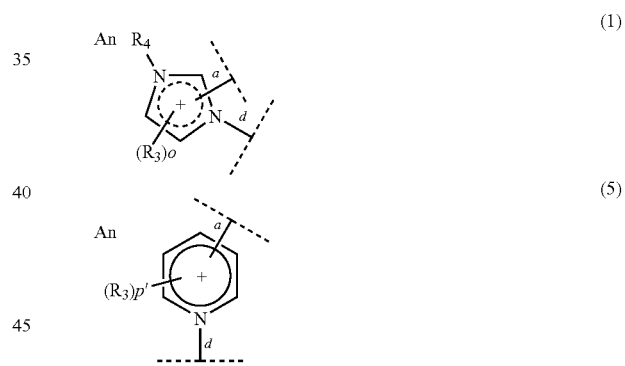

wherein radicals $R_3$ and $R_4$, o, p', a and d are defined according to claim 1.

3. The at least one polycationic hydrazone entity according to claim 1, wherein $R_1$ is chosen from:
 a hydrogen;
 a $C_1$-$C_4$ alkyl radical, optionally substituted with at least one radical, which may or may not be identical, chosen from the radicals hydroxyl; $C_1$-$C_2$ alkoxy; $C_2$-$C_4$ (poly)hydroxyalkoxy; amino substituted with one or two $C_1$-$C_2$ alkyl(s) which may or may not be identical; thio (—SH); $C_1$-$C_4$ thioalkyl (—RS); ($C_1$-$C_4$)alkylsulphinyl; ($C_1$-$C_4$)alkylsulphonyl;
 an alkylcarbonyl radical (R—CO—) wherein R is a $C_1$-$C_4$ alkyl radical; an alkylsulphonyl radical (RSO₂—) wherein R is a $C_1$-$C_4$ alkyl radical; an arylsulphonyl radical (R'SO₂—) wherein R' is an optionally substituted phenyl or benzyl radical;
 a (di)(alkyl)aminosulphonyl radical ((R)₂N—SO₂—) wherein the R radicals independently are chosen from hydrogen and $C_1$-$C_4$ alkyl radicals; a (di)(alkyl)aminocarbonyl radical $((R)_2N-CO-)$ wherein the R radicals independently are chosen from hydrogen and $C_1$-$C_4$ alkyl radicals;

a chlorine atom;
a hydroxyl group;
a $C_1$-$C_4$ alkoxy group;
a $C_2$-$C_4$ hydroxyalkoxy group;
a hydroxycarbonyl group;
an alkoxycarbonyl group (RO—CO—) wherein R is a $C_1$-$C_4$ alkyl radical;
an alkylcarbonyloxy radical (RCO—O—) wherein R is a $C_1$-$C_4$ alkyl radical;
an optionally substituted aryloxy group;
an $NR_7R_8$ group in which $R_7$ and $R_8$ are, independently of one another, chosen from:
  a hydrogen atom;
  a $C_1$-$C_4$ alkyl radical optionally carrying at least one hydroxyl or $C_1$-$C_2$ alkoxy group, it being possible for said alkyl radicals to optionally form, with the nitrogen atom to which they are attached, a saturated or unsaturated, optionally substituted, optionally aromatic heterocycle comprising from 5 to 7 ring members, and optionally comprising another heteroatom which may be identical to or different from nitrogen;
  a phenyl radical; an aminophenyl radical; a 4-N,N-diethylaminophenyl radical; a methoxyphenyl radical;
an alkylcarbonylamino group (RCO—NR'—) wherein the R radical is a $C_1$-$C_4$ alkyl radical and the R' radical is chosen from a hydrogen atom and a $C_1$-$C_4$ alkyl radical; and
an alkylsulphonylamino group ($RSO_2$—NR'—) wherein the R' radical is chosen from a hydrogen atom and a $C_1$-$C_4$ alkyl radical, and the R radical is a $C_1$-$C_4$ alkyl radical.

4. The at least one polycationic hydrazone entity according to claim 1, wherein $R_1$ is chosen from:
a hydrogen;
a $C_1$-$C_4$ alkyl radical optionally substituted with a hydroxyl or $C_1$-$C_2$ alkoxy group;
a chlorine atom;
a hydroxyl group;
a $C_1$-$C_4$ alkoxy group;
a $C_2$-$C_4$ hydroxyalkoxy group;
a hydroxycarbonyl group;
an alkoxycarbonyl group (RO—CO—) wherein R is a $C_1$-$C_2$ alkyl radical;
an unsubstituted aryloxy group;
an $NR_7R_8$ group wherein $R_7$ and $R_8$ are chosen, independently of one another, from:
  a hydrogen atom;
  a $C_1$-$C_4$ alkyl radical optionally carrying at least one hydroxyl or $C_1$-$C_2$ alkoxy group, it being possible for said alkyl radicals to optionally form, with the nitrogen atom to which they are attached, a saturated or unsaturated, optionally substituted, optionally aromatic heterocycle comprising from 5 to 7 ring members, and optionally comprising another heteroatom which may be identical to or different from nitrogen; and
  a phenyl radical; a 4-N,N-diethylaminophenyl radical; a methoxyphenyl radical;
an alkylcarbonylamino group (RCO—NR'—) wherein the R radical is a $C_1$-$C_4$ alkyl radical and the R' radical is chosen from a hydrogen atom and a $C_1$-$C_4$ alkyl radical; and
an alkylsulphonylamino group ($RSO_2$—NR'—) wherein the R' radical is chosen from a hydrogen atom and a $C_1$-$C_2$ alkyl radical, and the R radical is a $C_1$-$C_2$ alkyl radical.

5. The at least one polycationic hydrazone entity according to claim 1, wherein $R_2$ and $R_3$, independently of one another, are chosen from:
a chlorine atom;
a $C_1$-$C_{16}$ alkyl radical optionally substituted with at least one group, which may or may not be identical, chosen from hydroxyl, $C_1$-$C_2$ alkoxy, amino, thio, $C_1$-$C_2$ ((di)alkyl)amino, $C_1$-$C_2$ alkylsulphonylamino and $C_1$-$C_2$ alkylsulphonyl radicals;
a hydroxyl radical;
a $C_1$-$C_4$ alkoxy radical; a $C_2$-$C_4$ hydroxyalkoxy group;
a hydroxycarbonyl radical;
a ($C_1$-$C_4$)alkoxycarbonyl radical;
a ($C_1$-$C_4$)alkylcarbonyloxy radical;
an optionally substituted aryloxy radical;
an amino radical optionally substituted with one or two $C_1$-$C_4$ alkyl radicals, which may be identical or different, optionally carrying at least one hydroxyl or $C_1$-$C_2$ alkoxy group, it being possible for said alkyl radicals to optionally form, with the nitrogen atom to which they are attached, a saturated or unsaturated, optionally substituted, optionally aromatic heterocycle comprising 5 or 7 ring members, and optionally comprising another heteroatom which may be identical to or different from nitrogen; or with one or two radicals chosen from phenyl, aminophenyl, N,N-diethylaminophenyl and methoxyphenyl radicals;
a ($C_1$-$C_4$)alkylcarbonylamino radical;
an aminocarbonyl radical, a ($C_1$-$C_4$)(di)alkylaminocarbonyl group;
an aminosulphonyl or ($C_1$-$C_4$)(di)alkylaminosulphonyl radical;
a ($C_1$-$C_4$)alkylthio radical;
a ($C_1$-$C_4$)alkylsulphonylamino radical;
a cyano radical;
a phenyl radical;
a trifluoromethyl radical;
a thio radical; and
a ($C_1$-$C_4$)alkylsulphonyl radical.

6. The at least one polycationic hydrazone entity according to claim 1, wherein $R_2$ and $R_3$, independently of one another, are chosen from:
a chlorine atom;
a $C_1$-$C_8$ alkyl radical optionally substituted with at least one group, which may or may not be identical, chosen from hydroxyl, $C_1$-$C_2$ alkoxy, amino, thio, $C_1$-$C_2$ ((di)alkyl)amino, $C_1$-$C_2$ alkylsulphonylamino and $C_1$-$C_2$ alkylsulphonyl radicals;
a hydroxyl radical;
a $C_1$-$C_4$ alkoxy radical;
a ($C_2$-$C_4$)alkoxycarbonyl radical;
an optionally substituted aryloxy radical;
an amino radical optionally substituted:
  with one or two $C_1$-$C_4$ alkyl radicals, which may be identical or different, optionally carrying a hydroxyl or $C_1$-$C_2$ alkoxy group, it being possible for said alkyl radicals to optionally form, with the nitrogen atom to which they are attached, a saturated or unsaturated, optionally substituted heterocycle comprising 5 or 7 ring members;
  with one or two phenyl, aminophenyl or methoxyphenyl radicals;

a ($C_1$-$C_4$)alkylcarbonylamino radical in which the amino function is unsubstituted or substituted with a $C_1$-$C_4$ alkyl radical;
a hydroxycarbonyl radical;
an aminocarbonyl radical;
an aminosulphonyl or ($C_1$-$C_4$)(di)alkylaminosulphonyl radical;
a ($C_1$-$C_2$)alkylsulphonylamino radical;
a ($C_1$-$C_2$)alkylsulphonyl radical;
a ($C_1$-$C_4$)alkylthio radical;
a phenyl radical;
a trifluoromethyl radical; and
a thio radical.

7. The at least one polycationic hydrazone entity according to claim 1, wherein the two adjacent radicals $R_2$ form, with one another and with the carbon atoms to which they are attached, an optionally aromatic, substituted or unsubstituted cyclic radical comprising 5 or 6 ring members.

8. The at least one polycationic hydrazone entity according to claim 1, wherein the two adjacent radicals $R_3$ form, with one another and with the carbon atoms to which they are attached, a substituted or unsubstituted aromatic ring comprising 6 ring members.

9. The at least one polycationic hydrazone entity according to claim 1, wherein the radical $R_4$ is chosen from:
a $C_1$-$C_8$ alkyl radical optionally substituted with a radical chosen from hydroxyl, $C_1$-$C_4$ alkoxy, amino optionally substituted with one or two $C_1$-$C_2$ alkyl radicals;
a $C_1$-$C_4$ trimethylsilylalkyl radical;
a phenyl radical optionally substituted with one or two groups chosen from chlorine, a hydroxyl radical, and an amino radical; and
a benzyl radical optionally substituted with one or two groups chosen from chlorine, a hydroxyl radical, and an amino radical.

10. The at least one polycationic hydrazone entity according to claim 1, wherein $R_5$ is chosen from:
a hydrogen;
a $C_1$-$C_6$ alkyl radical optionally substituted with at least one hydroxyl group, with at least one $C_1$-$C_2$ alkoxy group or with at least one hydroxycarbonyl group;
a phenyl radical optionally substituted with at least one halogen atom or with at least one group chosen from hydroxyl and amino groups;
a benzyl radical optionally substituted with at least one group chosen from hydroxyl and amino groups;
a ($C_1$-$C_4$)alkylcarbonyl radical; and
a ($C_1$-$C_4$)alkylsulphonyl radical.

11. The at least one polycationic hydrazone entity according to claim 1, wherein $R_5$ forms, with a radical $R_2$ located in the ortho-position with respect to the $R_5$ group and with the nitrogen atom substituted with $R_5$, a saturated or unsaturated, substituted or unsubstituted heterocycle comprising 5 or 6 ring members.

12. The at least one polycationic hydrazone entity according to claim 1, wherein $R_6$ is chosen from:
a hydrogen atom;
a $C_1$-$C_4$ alkyl radical optionally substituted with at least one radical chosen from hydroxyl, $C_1$-$C_2$ alkoxy, $C_2$-$C_4$ (poly)hydroxyalkoxy, amino, $C_1$-$C_2$ (di)alkylamino, thio (—SH), ($C_1$-$C_4$)alkylsulphinyl, ($C_1$-$C_4$)alkylsulphonyl and ($C_1$-$C_4$)thioalkyl radicals;
an amino group optionally substituted with at least one $C_1$-$C_4$ alkyl radical, which may be identical or different, optionally carrying at least one hydroxyl group;
an alkylcarbonylamino group (RCO—NR—) wherein the R radicals are chosen from, independently of one another, a $C_1$-$C_4$ alkyl radical;
an alkylsulphonylamino group ($RSO_2$—NR'—) wherein the R and R' radicals are chosen from, independently of one another, a hydrogen atom and a $C_1$-$C_4$ alkyl radical;
a hydroxycarbonyl radical;
a $C_1$-$C_2$ alkoxycarbonyl radical;
a phenyl radical optionally substituted with at least one radical chosen from hydroxyl, $C_1$-$C_2$ alkoxy, $C_2$-$C_4$ (poly)hydroxyalkoxy, amino and $C_1$-$C_2$ (di)alkylamino radicals; and
a benzyl radical optionally substituted with at least one radical chosen from hydroxyl, $C_1$-$C_2$ alkoxy, $C_2$-$C_4$ (poly)hydroxyalkoxy, amino and $C_1$-$C_2$ (di)alkylamino radicals.

13. The at least one polycationic hydrazone entity according to claim 1, wherein $R_6$ is chosen from:
a hydrogen;
a methyl, ethyl or 2-hydroxyethyl radical;
an amino radical;
a hydroxycarbonyl radical;
a methoxycarbonyl radical;
a methylcarbonylamino group ($CH_3CO$—NH—);
a methylsulphonylamino group ($CH_3SO_2$—NH—);
a phenyl radical optionally substituted with a group chosen from hydroxyl and amino groups or a combination thereof; and
a benzyl radical optionally substituted with a group chosen from hydroxyl and amino groups or a combination thereof.

14. The at least one polycationic hydrazone entity according to claim 1, wherein Z is a cationic $C_2$-$C_{20}$ alkylene radical:
1—interrupted with at least one group, which may or may not be identical, corresponding to the following formulae:

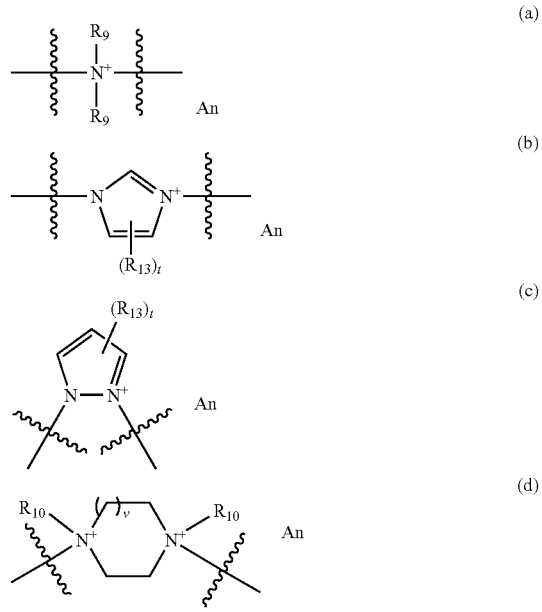

-continued

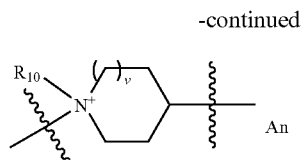
(e)

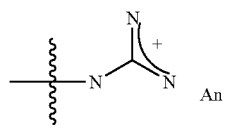
(f)

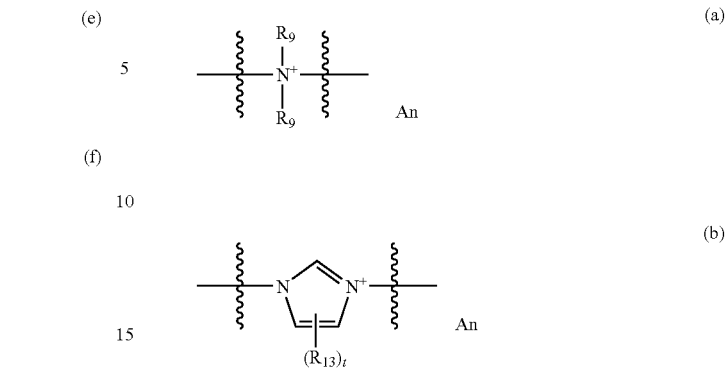
(a)

(b)

wherein:

R$_9$ and R$_{10}$, independently of one another, are chosen from a C$_1$-C$_8$ alkyl radical; a C$_1$-C$_6$ monohydroxyalkyl radical; a C$_2$-C$_6$ polyhydroxyalkyl radical; a (C$_1$-C$_6$)alkoxy (C$_1$-C$_6$)alkyl radical; an aryl radical which is optionally substituted; an arylalkyl radical which is optionally substituted; a C$_1$-C$_6$ aminoalkyl radical in which the amine is substituted with one or two C$_1$-C$_4$ alkyl radicals which may be identical or different; a (C$_1$-C$_6$)alkylsulphonyl radical;

two radicals R$_9$ can form, together with the nitrogen atom to which they are attached, a saturated or unsaturated, optionally substituted ring comprising 5, 6 or 7 ring members;

R$_{13}$, which may be identical or different, is chosen from a hydrogen atom, a halogen atom chosen from bromine, chlorine or fluorine, a C$_1$-C$_6$ alkyl radical, a C$_1$-C$_6$ monohydroxyalkyl radical, a C$_2$-C$_6$ polyhydroxyalkyl radical, a C$_1$-C$_6$ alkoxy radical, a C$_1$-C$_4$ (di)alkylamino radical, a hydroxycarbonyl radical, a C$_1$-C$_6$ alkylcarbonyl radical, a C$_1$-C$_6$ thioalkyl radical, a (C$_1$-C$_6$)alkylthio radical, a (C$_1$-C$_6$)alkylsulphonyl radical, a benzyl radical which is optionally substituted, a phenyl radical which is optionally substituted with at least one radical chosen from methyl, hydroxyl, amino and methoxy radicals;

An is an organic or inorganic anion or a mixture of organic or inorganic anions;

t is an integer ranging from 0 to 3; if t<3, then the unsubstituted carbon atoms carry a hydrogen atom;

v is an integer equal to 1 or 2;

2—optionally interrupted with at least one heteroatom or group comprising at least one heteroatom or combinations thereof; on the condition that there is not any azo, nitro, nitroso or peroxo group or bond in the group Z; and 3—optionally substituted with at least one radical chosen from: hydroxyl, C$_1$-C$_2$ alkoxy, C$_2$-C$_4$ (poly)hydroxyalkoxy, and amino substituted with one or two C$_1$-C$_2$ linear alkyl groups optionally carrying at least one hydroxyl, (C$_1$-C$_4$)trialkylsilyl or imidazole group.

15. The at least one polycationic hydrazone entity according to claim 1, wherein Z is a C$_2$-C$_{20}$ alkylene radical:

1—interrupted with one or two groups, which may or may not be identical, corresponding to the following formulae:

wherein:

R$_9$, independently of one another, are chosen from a C$_1$-C$_8$ alkyl radical; a C$_1$-C$_6$ monohydroxyalkyl radical; a (C$_1$-C$_6$)alkoxy(C$_1$-C$_6$)alkyl radical; a phenyl radical; and a benzyl radical;

wherein the two radicals R$_9$ can form, together with the nitrogen atom to which they are attached, a saturated or unsaturated, optionally substituted ring comprising 5 or 6 ring members;

R$_{13}$, which may be identical or different, is chosen from a hydrogen atom, a C$_1$-C$_6$ alkyl radical, a C$_1$-C$_6$ monohydroxyalkyl radical, a C$_1$-C$_6$ alkoxy radical and a C$_1$-C$_4$ (di)alkylamino radical;

An is a cosmetically acceptable organic or inorganic anion or a mixture of cosmetically acceptable organic or inorganic anions;

t is an integer ranging from 0 to 3; if t<3, then the unsubstituted carbon atoms carry a hydrogen atom;

v is an integer equal to 1 or 2; and

2—and optionally substituted with a radical chosen from the radicals: hydroxyl, C$_1$-C$_2$ alkoxy, C$_2$-C$_4$ hydroxyalkoxy, and amino substituted with one or two C$_1$-C$_2$ linear alkyl groups optionally carrying a hydroxyl, (C$_1$-C$_3$)trialkylsilyl or imidazole group.

16. The at least one polycationic hydrazone entity according to claim 1, wherein X is CR$_2$.

17. A composition for dyeing human keratin fibers, comprising, in a cosmetically acceptable medium, at least one polycationic hydrazone entity chosen from compounds of formula (I), tautomeric forms thereof, acid-addition salts thereof and solvates thereof:

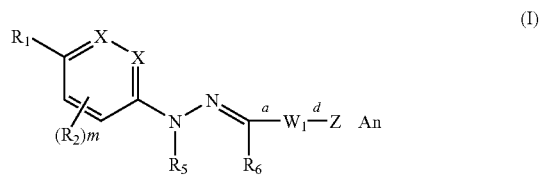
(I)

wherein:

W$_1$ is a heteroaromatic radical of following formulae (1) to (8):

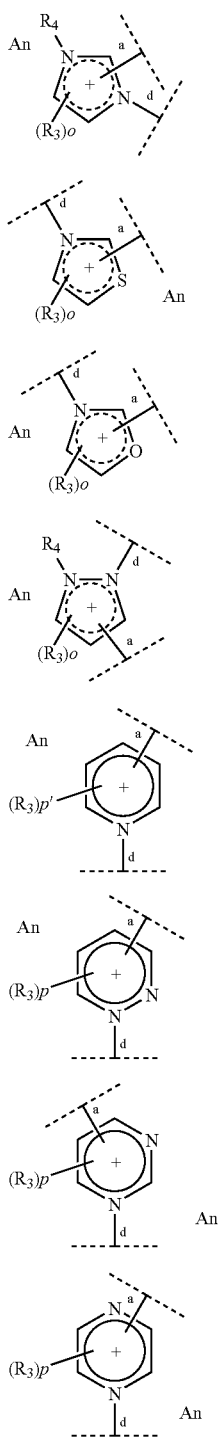

wherein:

the radical $R_1$ is chosen from:
a hydrogen;
an optionally substituted $C_1$-$C_{20}$ alkyl radical, optionally interrupted with at least one heteroatom and/or with at least one group comprising at least one heteroatom, wherein the alkyl radical does not comprise any nitro, nitroso, peroxo or diazo function;

an alkylcarbonyl radical (R—CO—) wherein R is a $C_1$-$C_4$ alkyl radical;
an alkylsulphonyl radical (RSO$_2$—) wherein R is a $C_1$-$C_4$ alkyl radical;
an arylsulphonyl radical (R'SO$_2$—) wherein R' is an optionally substituted phenyl or benzyl radical;
a (di)(alkyl)aminosulphonyl radical ((R)$_2$N—SO$_2$—) wherein the R radicals independently are chosen from a hydrogen and a $C_1$-$C_4$ alkyl radical;
a (di)(alkyl)aminocarbonyl radical ((R)$_2$N—CO—) wherein the R radicals independently are chosen from a hydrogen and a $C_1$-$C_4$ alkyl radical;
a halogen atom;
a hydroxyl group;
a $C_1$-$C_4$ alkoxy group;
a $C_2$-$C_4$ (poly)hydroxyalkoxy group;
a hydroxycarbonyl group;
an alkoxycarbonyl group (RO—CO—) wherein R is a $C_1$-$C_4$ alkyl radical;
an alkylcarbonyloxy radical (RCO—O—) wherein R is a $C_1$-$C_4$ alkyl radical;
an optionally substituted aryloxy group;
an $NR_7R_8$ group wherein $R_7$ and $R_8$ are chosen from, independently of one another:
  a hydrogen atom;
  a $C_1$-$C_4$ alkyl radical, optionally carrying at least one hydroxyl or $C_1$-$C_2$ alkoxy group, it being possible for said alkyl radicals to optionally form, with the nitrogen atom to which they are attached, a saturated or unsaturated, optionally substituted, optionally aromatic heterocycle containing from 5 to 7 ring members, optionally comprising another heteroatom which may be identical to or different from nitrogen;
  a phenyl radical; an aminophenyl radical; a 4-N,N-diethylaminophenyl radical; a methoxyphenyl radical;
an alkylcarbonylamino group (RCO—NR'—) wherein the R radical is a $C_1$-$C_4$ alkyl radical and the R' radical is chosen from a hydrogen atom and a $C_1$-$C_4$ alkyl radical;
a ureido group (N(R)$_2$—CO—NR'—) wherein the R and R' radicals, independently of one another, are chosen from a hydrogen atom and $C_1$-$C_4$ alkyl radicals;
an alkylthio group (R—S—) wherein the R group is a $C_1$-$C_4$ alkyl radical;
an alkylsulphonylamino group (RSO$_2$—NR'—) wherein the R' radical is chosen from a hydrogen atom and a $C_1$-$C_4$ alkyl radical, and the R radical is a $C_1$-$C_4$ alkyl radical;
a cyano group; and
a trifluoromethyl group (CF$_3$);

The radicals $R_2$ and $R_3$, which may be identical or different, are chosen from, independently of one another:
a halogen atom;
an optionally substituted $C_1$-$C_{16}$ alkyl radical, optionally interrupted with at least one heteroatom and/or with at least one group comprising at least one heteroatom; wherein the alkyl radical does not comprise any nitro, nitroso, peroxo or diazo functions;
a hydroxyl radical;
a $C_1$-$C_4$ alkoxy radical;
a $C_2$-$C_4$ (poly)hydroxyalkoxy group;
a hydroxycarbonyl radical;
an alkoxycarbonyl radical (RO—CO—) wherein R is a $C_1$-$C_4$ alkyl radical;

an alkylcarbonyloxy radical (RCO—O) wherein R is a $C_1$-$C_4$ alkyl radical;

an optionally substituted aryloxy radical;

an optionally substituted arylamino radical;

an amino radical optionally substituted with one or two $C_1$-$C_4$ alkyl radicals, which may be identical or different, optionally carrying at least one hydroxyl or $C_1$-$C_2$ alkoxy group, it being possible for said alkyl radicals to optionally form, with the nitrogen atom to which they are attached, a saturated or unsaturated, optionally substituted, optionally aromatic heterocycle containing from 5 to 7 ring members, optionally comprising another heteroatom which may be identical to or different from nitrogen;

an alkylcarbonylamino radical (RCO—NR'—) wherein the R radical is a $C_1$-$C_4$ alkyl radical and the R' radical is chosen from a hydrogen and a $C_1$-$C_4$ alkyl radical;

a (di)(alkyl)aminocarbonyl group ((R)$_2$N—CO—) wherein the R radicals, independently of one another, are chosen from a hydrogen and a $C_1$-$C_4$ alkyl radical;

a ureido radical (N(R)$_2$—CO—NR'—) wherein the R radicals, independently of one another, are chosen from $C_1$-$C_4$ alkyl radicals, and R' is chosen from a hydrogen and a $C_1$-$C_4$ alkyl radical;

a (di)(alkyl)aminosulphonyl radical ((R)$_2$N—SO$_2$—) wherein the R radical is chosen from a hydrogen atom and a $C_1$-$C_4$ alkyl radical;

an alkylthio radical (R—S—) wherein the R radical is a $C_1$-$C_4$ alkyl radical;

an alkylsulphonylamino radical (RSO$_2$—NR'—) wherein the R radical is a $C_1$-$C_4$ alkyl radical, and the R' radical is chosen from a hydrogen atom and a $C_1$-$C_4$ alkyl radical;

an alkylsulphonyl radical (RSO$_2$—) wherein the R radical is a $C_1$-$C_4$ alkyl radical;

a cyano radical (—CN); and a trifluoromethyl radical (CF$_3$);

Two adjacent radicals $R_2$ can form, with one another and with the carbon atoms to which they are attached, a substituted or unsubstituted, aromatic or nonaromatic (hetero)cyclic radical comprising 5 or 6 ring members;

One of the radicals $R_7$ or $R_8$ can form, with the nitrogen atom to which it is attached and with a radical $R_2$ located in the ortho-position with respect to the NR$_7$R$_8$ group, a substituted or unsubstituted, saturated or unsaturated heterocycle comprising 5 or 6 ring members;

The radicals $R_7$ and $R_8$ can form, with the nitrogen atom to which they are attached and each with a radical $R_2$ located in the ortho-position with respect to the NR$_7$R$_8$ group, a substituted or unsubstituted, saturated or unsaturated heterocycle comprising 5 or 6 ring members;

m is an integer ranging from 0 to 4; when m is less than 4, the unsubstituted carbon atom(s) carries a hydrogen atom;

X, independently of one another, is N or CR$_2$;

o is an integer ranging from 0 to 2; when o is less than 2, the unsubstituted carbon atom(s) carries a hydrogen atom;

Two adjacent radicals $R_3$ can form, with one another and with the carbon atoms to which they are attached, a substituted or unsubstituted aromatic ring comprising 6 ring members;

The radicals $R_4$, which may be identical or different, are chosen from:

an optionally substituted $C_1$-$C_{20}$ alkyl radical, optionally interrupted with at least one heteroatom and/or with at least one group comprising at least one heteroatom, wherein the alkyl radical does not comprise any nitro, nitroso, peroxo or diazo function;

a $C_1$-$C_4$ trimethylsilylalkyl radical;

an optionally substituted phenyl radical; and an optionally substituted benzyl radical;

The radical $R_5$ is chosen from:

a hydrogen;

an optionally substituted $C_1$-$C_{20}$ alkyl radical, optionally interrupted with at least one heteroatom and/or with at least one group comprising at least one heteroatom, wherein the alkyl radical does not comprise any nitro, nitroso, peroxo or diazo function;

an optionally substituted phenyl radical;

an optionally substituted benzyl radical;

an alkylcarbonyl radical (R—CO—) wherein R is a $C_1$-$C_4$ alkyl radical;

an alkylsulphonyl radical (RSO$_2$—) wherein R is a $C_1$-$C_4$ alkyl radical;

an arylsulphonyl radical (R'SO$_2$—) wherein R' is an optionally substituted phenyl or benzyl radical;

a (di)(alkyl)aminosulphonyl radical ((R)$_2$N—SO$_2$—) wherein the R radicals are independently chosen from a hydrogen and a $C_1$-$C_4$ alkyl radical; and a (di)(alkyl)aminocarbonyl radical ((R)$_2$N—CO—) wherein the R radicals are independently chosen from a hydrogen and a $C_1$-$C_4$ alkyl radical;

$R_5$ can form, with a radical $R_2$ located in the ortho-position with respect to the NR$_5$ group and with the nitrogen atom substituted with $R_5$, a substituted or unsubstituted, saturated or unsaturated heterocycle comprising 5 or 6 ring members;

The radical $R_6$ is chosen from:

a hydrogen atom;

an optionally substituted $C_1$-$C_{16}$ alkyl radical, optionally interrupted with at least one heteroatom and/or with at least one group comprising at least one heteroatom, wherein the alkyl radical does not comprise any nitro, nitroso, peroxo or diazo function;

an amino radical optionally substituted with one or two $C_1$-$C_4$ alkyl radicals, which may be identical or different, optionally carrying at least one hydroxyl or $C_1$-$C_2$ alkoxy group, it being possible for said alkyl radicals to optionally form, with the nitrogen atom to which they are attached, an optionally substituted, saturated or unsaturated or aromatic heterocycle comprising 5 or 6 ring members, optionally comprising at least one other heteroatom which may be identical to or different from nitrogen;

an alkylcarbonylamino radical (RCO—NR'—) wherein the R radical is a $C_1$-$C_4$ alkyl radical and the R' radical is chosen from a hydrogen and a $C_1$-$C_4$ alkyl radical;

a ureido radical (N(R)$_2$CO—NR'—) wherein the R radicals, independently of one another, are chosen from a $C_1$-$C_4$ alkyl radical, and R' is chosen from a hydrogen and a $C_1$-$C_4$ alkyl radical;

an alkylsulphonylamino radical (RSO$_2$—NR'—) wherein the R radical is a $C_1$-$C_4$ alkyl radical and the R' radical is chosen from a hydrogen and a $C_1$-$C_4$ alkyl radical;

a hydroxycarbonyl radical (HOOC—);

a $C_1$-$C_4$ alkoxycarbonyl radical (RO—CO—);

an optionally substituted phenyl radical; and an optionally substituted benzyl radical;

p is an integer ranging from 0 to 3; p' is an integer ranging from 0 to 4; when p is less than 3, or p' is less than 4, the unsubstituted carbon atom(s) carries a hydrogen atom;

The bond a links the heteroaromatic radical $W_1$ to the carbon atom of the $CR_6$ group;

Z is a $C_2$-$C_{20}$ alkylene radical comprising at least one quaternized nitrogen atom;

the bond d links the cationic group(s) Z to a nitrogen atom of the heteroaromatic radical $W_1$;

the electroneutrality of the compounds of formula (I) being ensured by at least one cosmetically acceptable anion An or a mixture of cosmetically acceptable anions An, which may or may not be identical;

and the following compounds wherein, $R_1$, $R_2$, m, and An are as defined above, for which R is chosen from a hydrogen atom and a methyl radical:

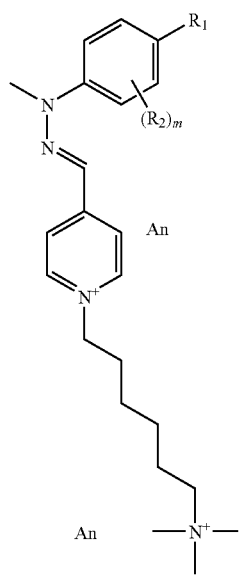

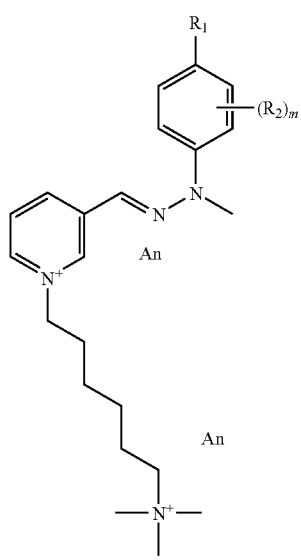

-continued

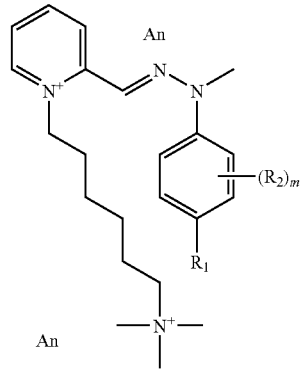

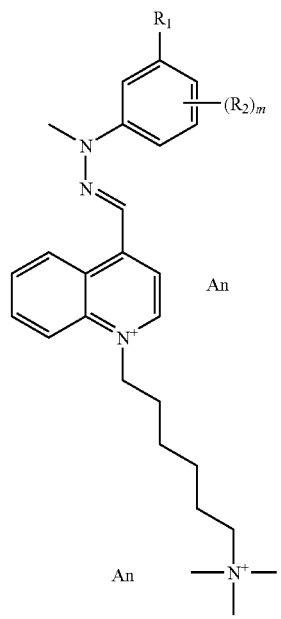

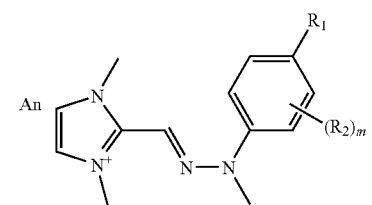

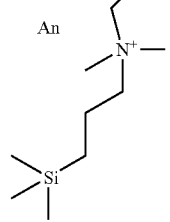

123
-continued
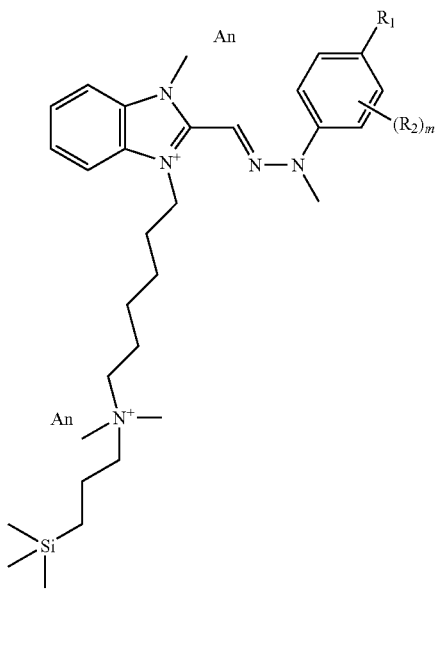
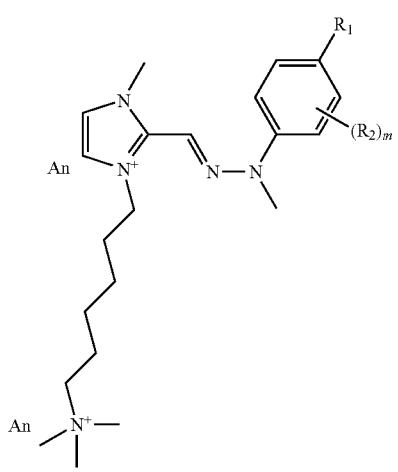
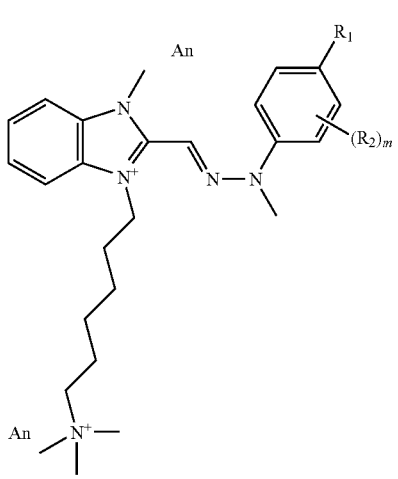
124
-continued
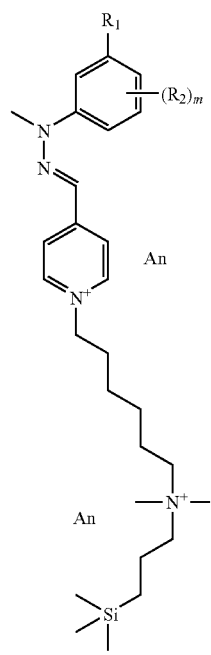
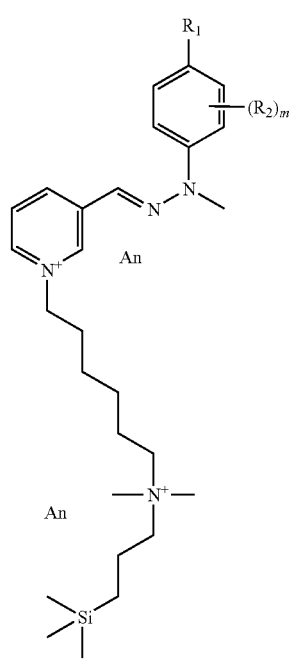

125
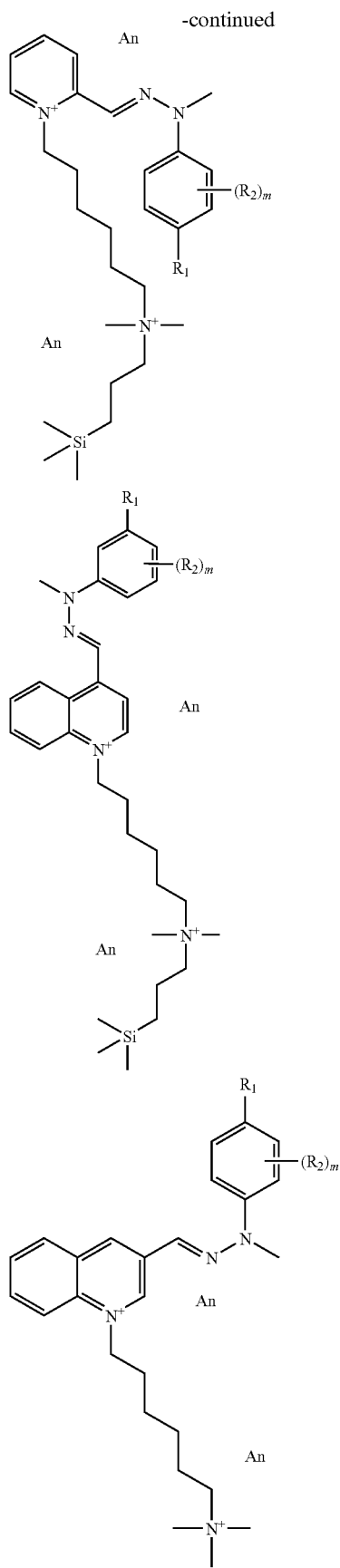
126
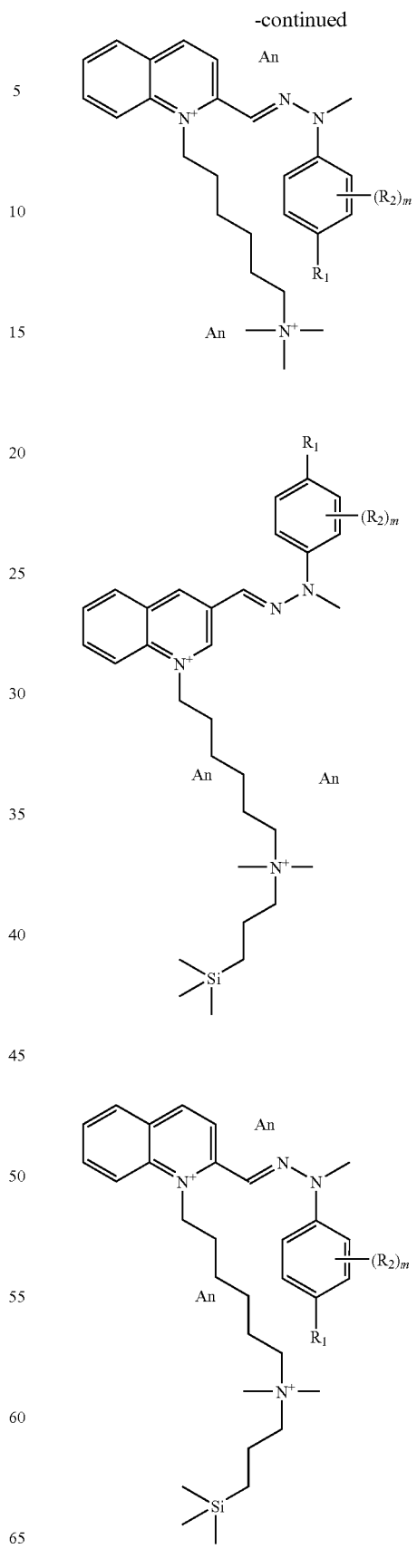

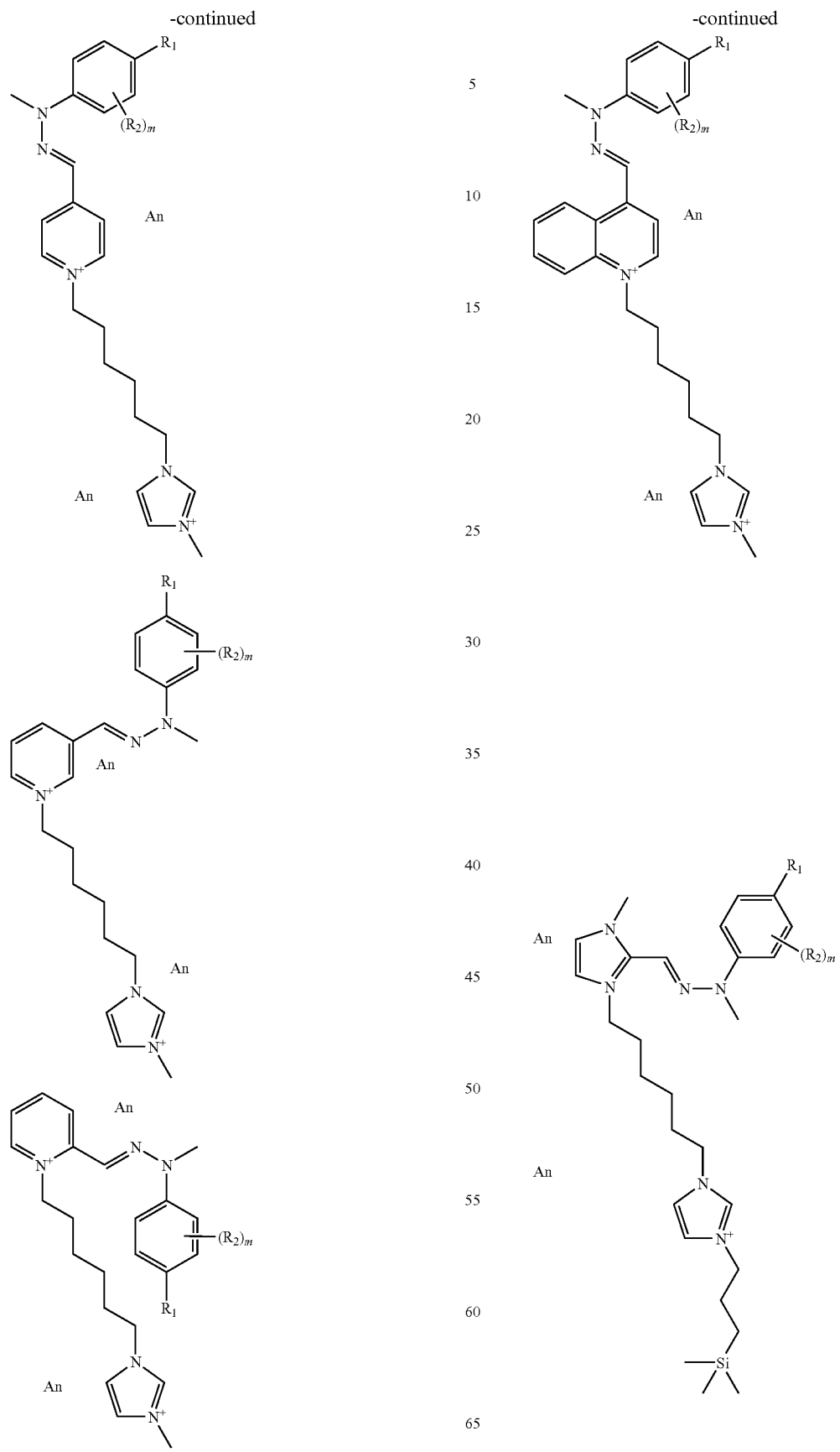

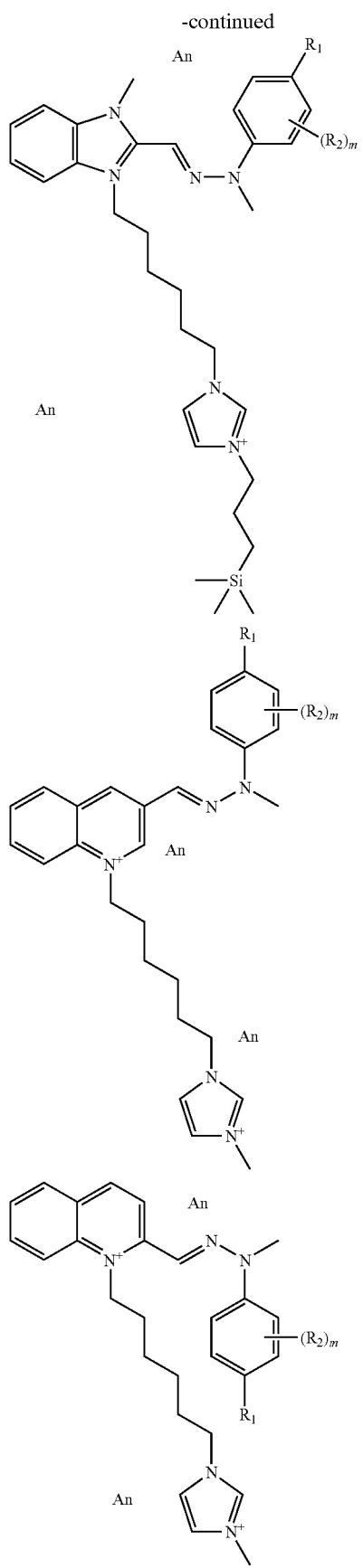
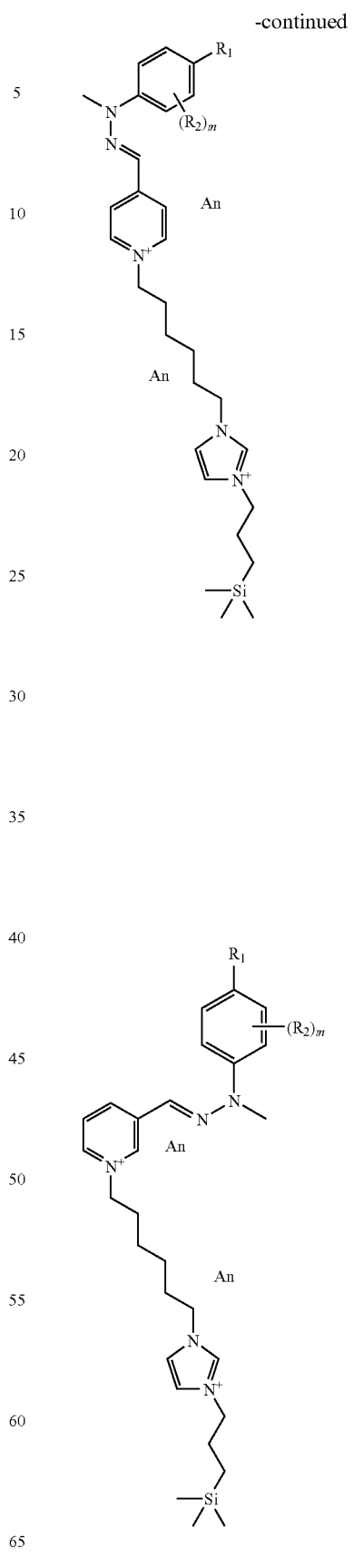

131
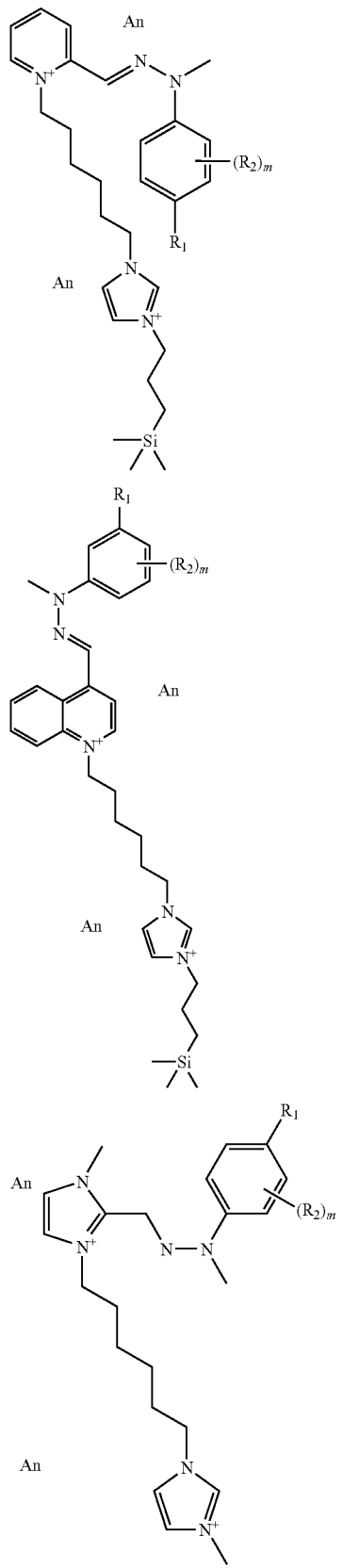
132
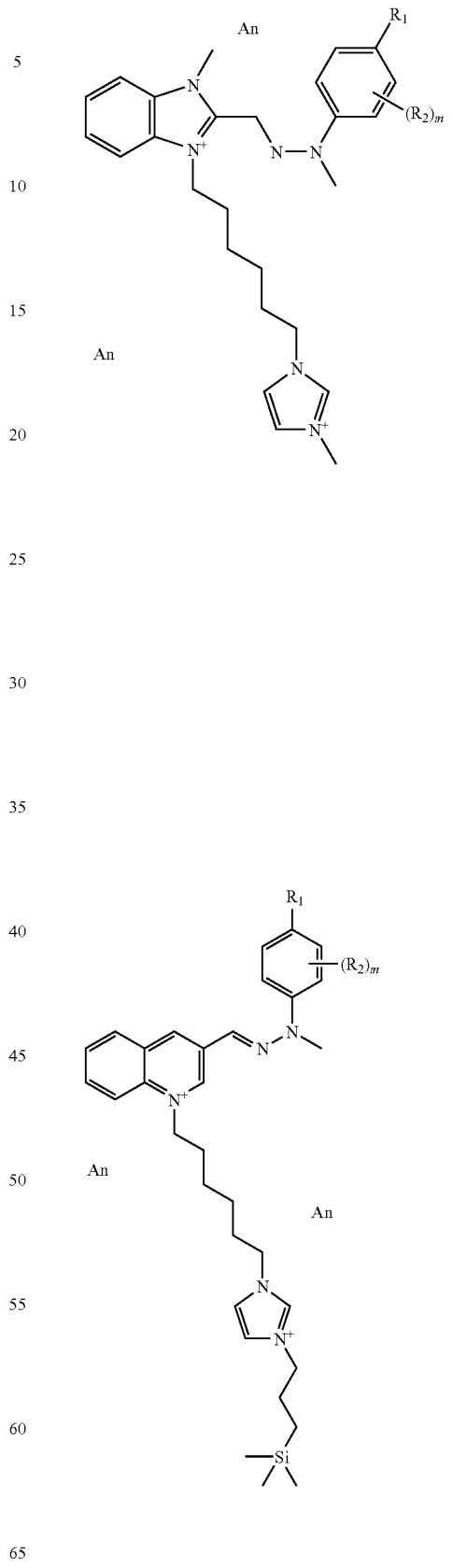

133
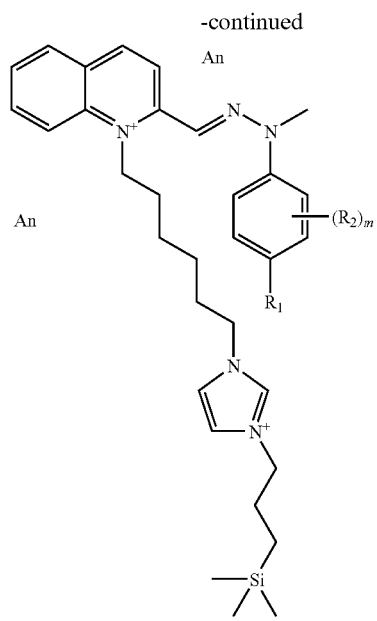
134
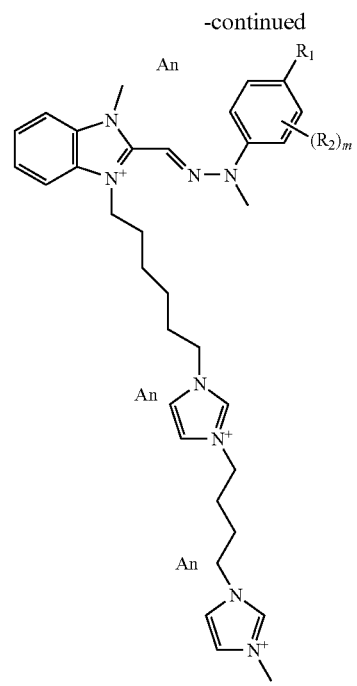
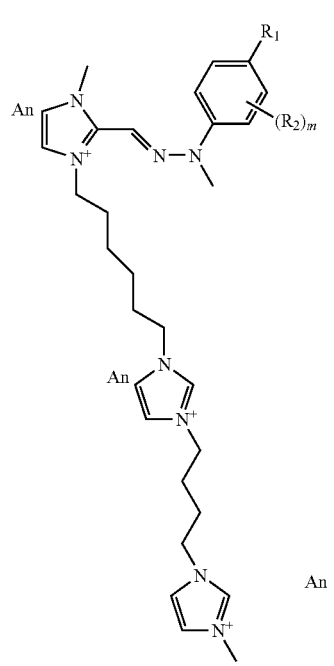
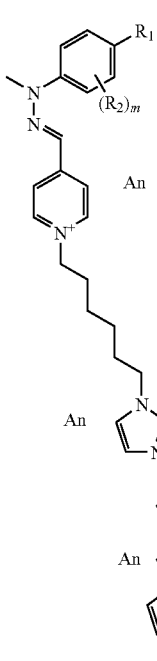

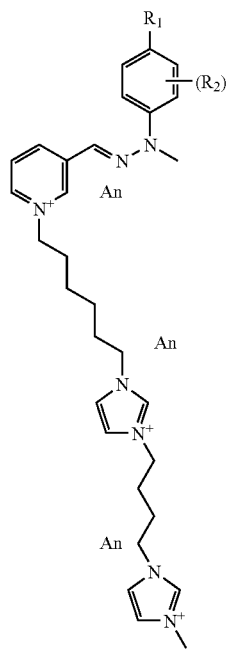
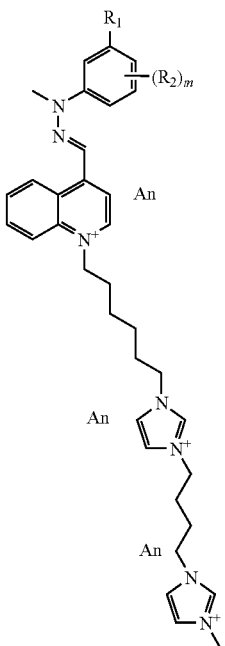
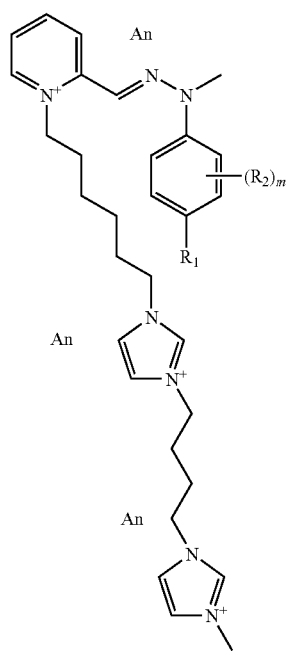
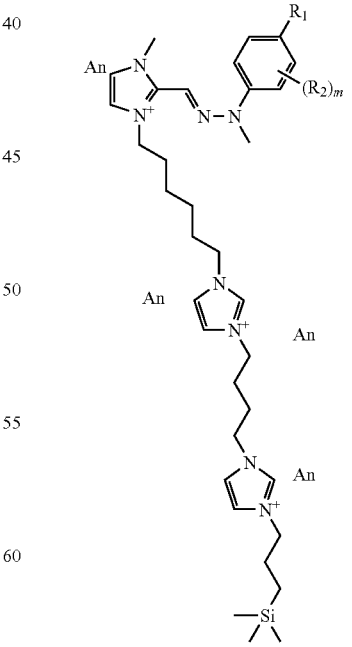

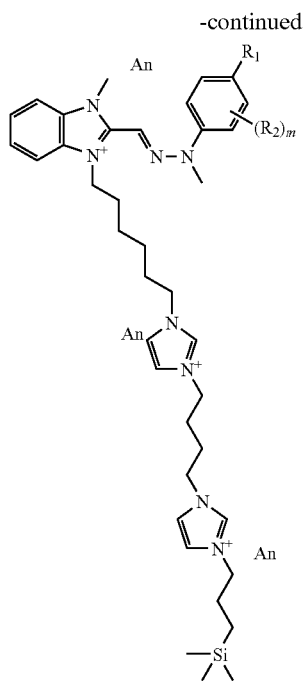
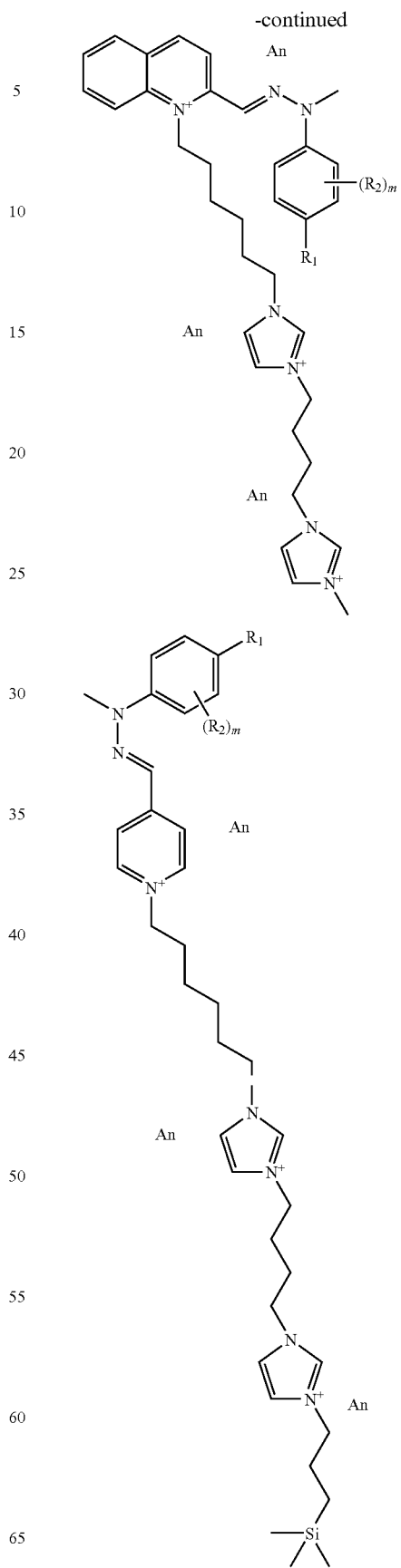

-continued
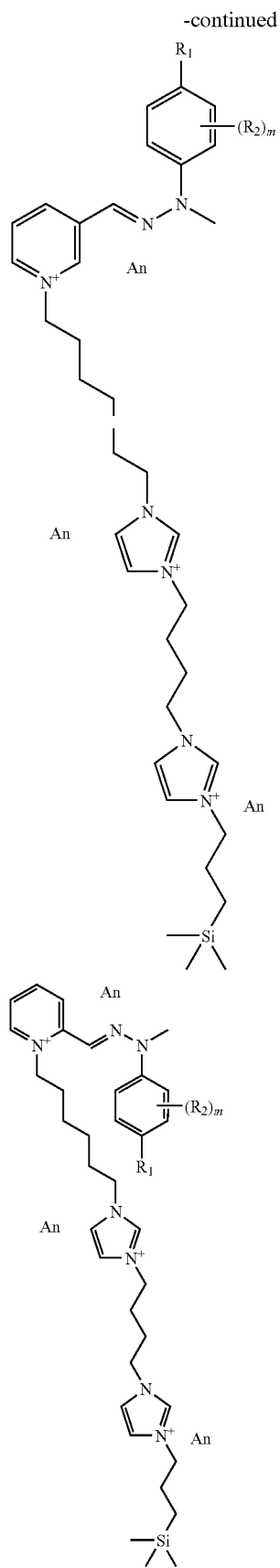
-continued
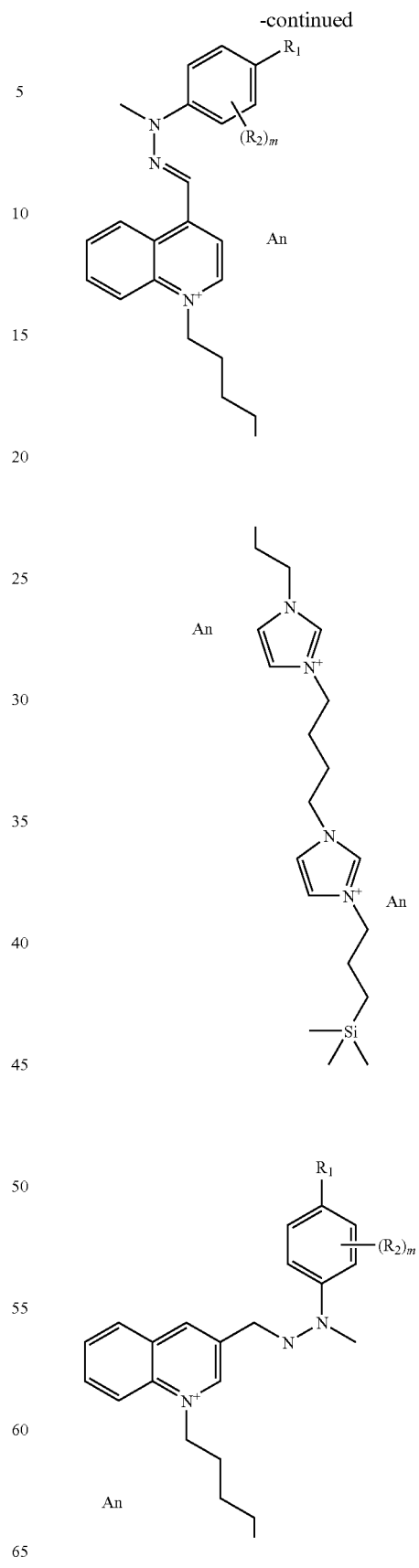

-continued
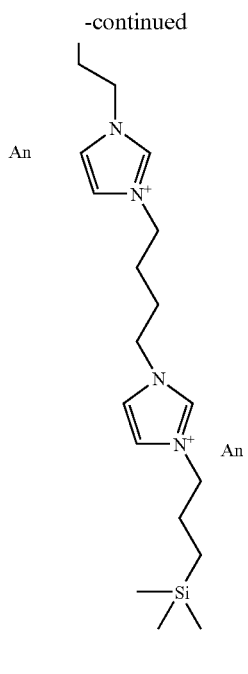
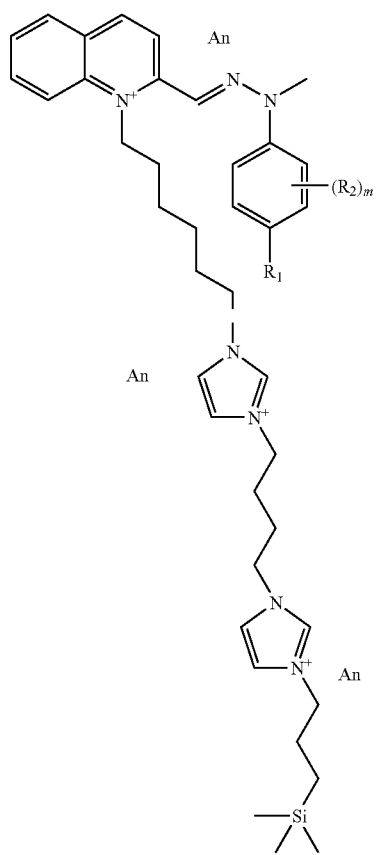
-continued
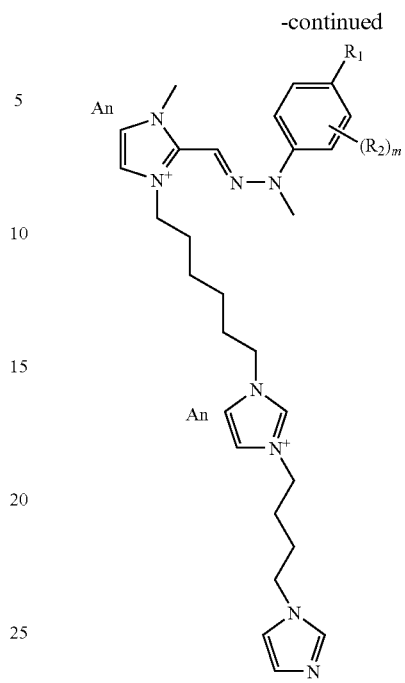
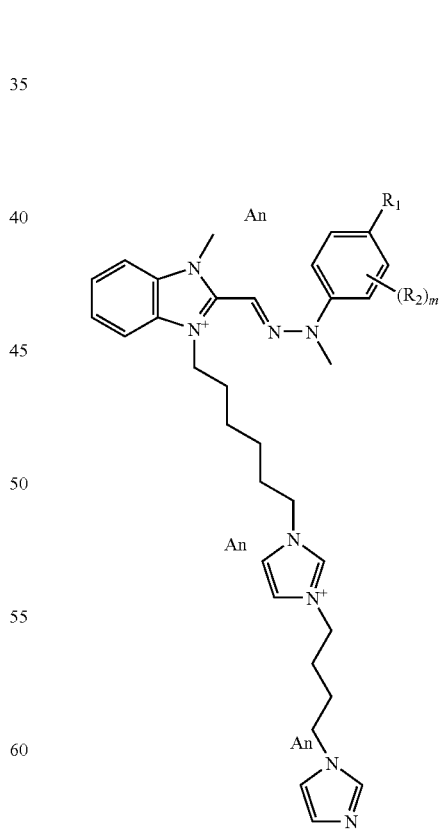

-continued
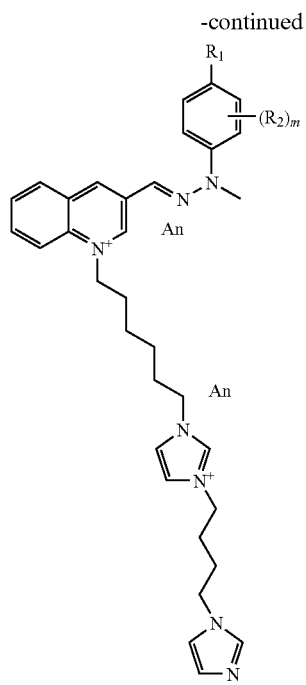
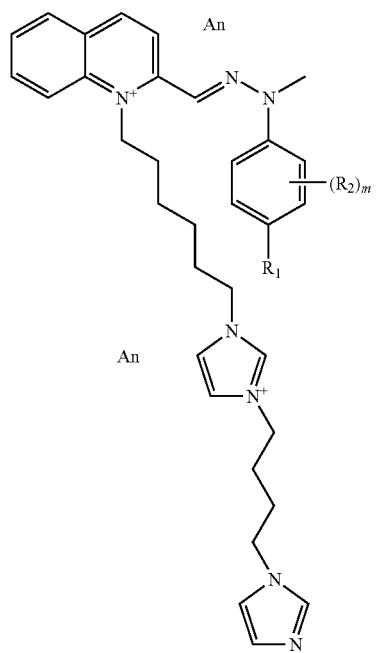
-continued
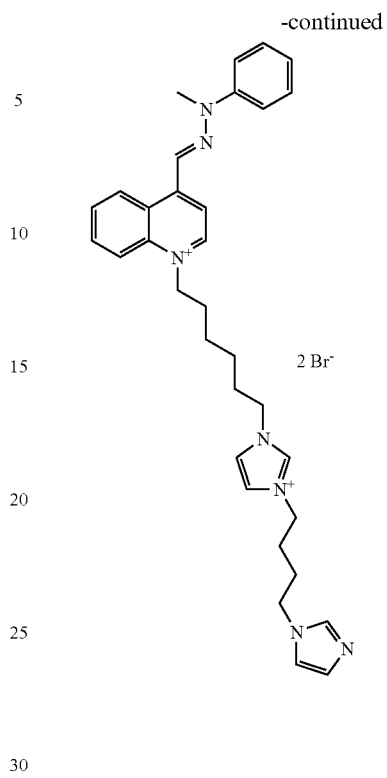
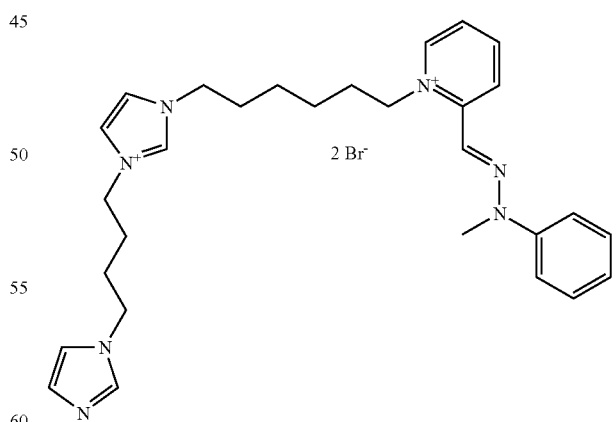

-continued

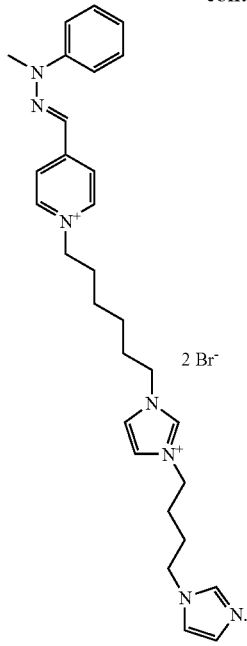

2 Br⁻

18. The composition according to claim 17, wherein the composition comprises from 0.001% to 10% by weight of the at least one polycationic hydrazone entity chosen from compounds of formula (I) relative to the total weight of the composition.

19. The composition according to claim 18, wherein the composition further comprises at least one oxidizing agent chosen from hydrogen peroxide, urea peroxide, alkaline metal bromates, persalts, peracids and oxidase enzymes.

20. A method for dyeing human keratin fibers, comprising:
applying a dye composition to the keratin fibers,
leaving the dye composition to act for a period of time sufficient to obtain a desired effect,
wherein the dye composition comprises at least one polycationic hydrazone entity chosen from compounds of formula (I), tautomeric forms thereof, acid-addition salts thereof and solvates thereof:

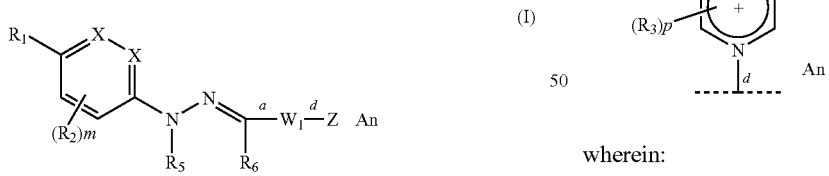

wherein:
$W_1$ is a heteroaromatic radical of following formulae (1) to (8):

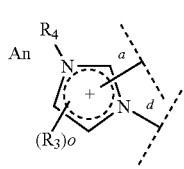

-continued

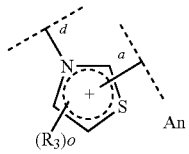

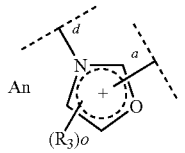

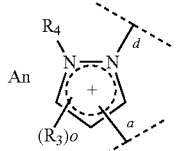

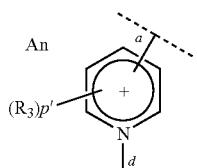

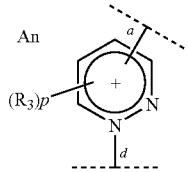

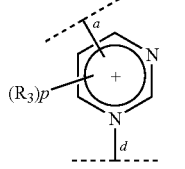

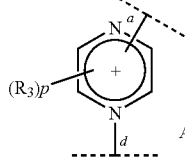

wherein:
the radical $R_1$ is chosen from:
a hydrogen;
an optionally substituted $C_1$-$C_{20}$ alkyl radical, optionally interrupted with at least one heteroatom and/or with at least one group comprising at least one heteroatom, wherein the alkyl radical does not comprise any nitro, nitroso, peroxo or diazo function;
an alkylcarbonyl radical (R—CO—) wherein R is a $C_1$-$C_4$ alkyl radical;
an alkylsulphonyl radical (RSO$_2$—) wherein R is a $C_1$-$C_4$ alkyl radical;
an arylsulphonyl radical (R'SO$_2$—) wherein R' is an optionally substituted phenyl or benzyl radical;

a (di)(alkyl)aminosulphonyl radical ((R)$_2$N—SO$_2$—) wherein the R radicals independently are chosen from a hydrogen and a C$_1$-C$_4$ alkyl radical;

a (di)(alkyl)aminocarbonyl radical ((R)$_2$N—CO—) wherein the R radicals independently are chosen from a hydrogen and a C$_1$-C$_4$ alkyl radical;

a halogen atom;

a hydroxyl group;

a C$_1$-C$_4$ alkoxy group;

a C$_2$-C$_4$ (poly)hydroxyalkoxy group;

a hydroxycarbonyl group;

an alkoxycarbonyl group (RO—CO—) wherein R is a C$_1$-C$_4$ alkyl radical;

an alkylcarbonyloxy radical (RCO—O—) wherein R is a C$_1$-C$_4$ alkyl radical;

an optionally substituted aryloxy group;

an NR$_7$R$_8$ group wherein R$_7$ and R$_8$ are chosen from, independently of one another:
  a hydrogen atom;
  a C$_1$-C$_4$ alkyl radical, optionally carrying at least one hydroxyl or C$_1$-C$_2$ alkoxy group, it being possible for said alkyl radicals to optionally form, with the nitrogen atom to which they are attached, a saturated or unsaturated, optionally substituted, optionally aromatic heterocycle containing from 5 to 7 ring members, optionally comprising another heteroatom which may be identical to or different from nitrogen;
  a phenyl radical; an aminophenyl radical; a 4-N,N-diethylaminophenyl radical; a methoxyphenyl radical;

an alkylcarbonylamino group (RCO—NR'—) wherein the R radical is a C$_1$-C$_4$ alkyl radical and the R' radical is chosen from a hydrogen atom and a C$_1$-C$_4$ alkyl radical;

a ureido group (N(R)$_2$—CO—NR'—) wherein the R and R' radicals, independently of one another, are chosen from a hydrogen atom and C$_1$-C$_4$ alkyl radicals;

an alkylthio group (R—S—) wherein the R group is a C$_1$-C$_4$ alkyl radical;

an alkylsulphonylamino group (RSO$_2$—NR'—) wherein the R' radical is chosen from a hydrogen atom and a C$_1$-C$_4$ alkyl radical, and the R radical is a C$_1$-C$_4$ alkyl radical;

a cyano group; and a trifluoromethyl group (CF$_3$);

The radicals R$_2$ and R$_3$, which may be identical or different, are chosen from, independently of one another:
  a halogen atom;
  an optionally substituted C$_1$-C$_{16}$ alkyl radical, optionally interrupted with at least one heteroatom and/or with at least one group comprising at least one heteroatom; wherein the alkyl radical does not comprise any nitro, nitroso, peroxo or diazo functions;
  a hydroxyl radical;
  a C$_1$-C$_4$ alkoxy radical;
  a C$_2$-C$_4$ (poly)hydroxyalkoxy group;
  a hydroxycarbonyl radical;
  an alkoxycarbonyl radical (RO—CO—) wherein R is a C$_1$-C$_4$ alkyl radical;
  an alkylcarbonyloxy radical (RCO—O) wherein R is a C$_1$-C$_4$ alkyl radical;
  an optionally substituted aryloxy radical;
  an optionally substituted arylamino radical;
  an amino radical optionally substituted with one or two C$_1$-C$_4$ alkyl radicals, which may be identical or different, optionally carrying at least one hydroxyl or C$_1$-C$_2$ alkoxy group, it being possible for said alkyl radicals to optionally form, with the nitrogen atom to which they are attached, a saturated or unsaturated, optionally substituted, optionally aromatic heterocycle containing from 5 to 7 ring members, optionally comprising another heteroatom which may be identical to or different from nitrogen;
  an alkylcarbonylamino radical (RCO—NR'—) wherein the R radical is a C$_1$-C$_4$ alkyl radical and the R' radical is chosen from a hydrogen and a C$_1$-C$_4$ alkyl radical;
  a (di)(alkyl)aminocarbonyl group ((R)$_2$N—CO—) wherein the R radicals, independently of one another, are chosen from a hydrogen and a C$_1$-C$_4$ alkyl radical;
  a ureido radical (N(R)$_2$—CO—NR'—) wherein the R radicals, independently of one another, are chosen from C$_1$-C$_4$ alkyl radicals, and R' is chosen from a hydrogen and a C$_1$-C$_4$ alkyl radical;
  a (di)(alkyl)aminosulphonyl radical ((R)$_2$N—SO$_2$—) wherein the R radical is chosen from a hydrogen atom and a C$_1$-C$_4$ alkyl radical;
  an alkylthio radical (R—S—) wherein the R radical is a C$_1$-C$_4$ alkyl radical;
  an alkylsulphonylamino radical (RSO$_2$—NR'—) wherein the R radical is a C$_1$-C$_4$ alkyl radical, and the R' radical is chosen from a hydrogen atom and a C$_1$-C$_4$ alkyl radical;
  an alkylsulphonyl radical (RSO$_2$—) wherein the R radical is a C$_1$-C$_4$ alkyl radical;
  a cyano radical (—CN); and
  a trifluoromethyl radical (CF$_3$);

Two adjacent radicals R$_2$ can form, with one another and with the carbon atoms to which they are attached, a substituted or unsubstituted, aromatic or nonaromatic (hetero)cyclic radical comprising 5 or 6 ring members;

One of the radicals R$_7$ or R$_8$ can form, with the nitrogen atom to which it is attached and with a radical R$_2$ located in the ortho-position with respect to the NR$_7$R$_8$ group, a substituted or unsubstituted, saturated or unsaturated heterocycle comprising 5 or 6 ring members;

The radicals R$_7$ and R$_8$ can form, with the nitrogen atom to which they are attached and each with a radical R$_2$ located in the ortho-position with respect to the NR$_7$R$_8$ group, a substituted or unsubstituted, saturated or unsaturated heterocycle comprising 5 or 6 ring members;

m is an integer ranging from 0 to 4; when m is less than 4, the unsubstituted carbon atom(s) carries a hydrogen atom;

X, independently of one another, is N or CR$_2$;

o is an integer ranging from 0 to 2; when o is less than 2, the unsubstituted carbon atom(s) carries a hydrogen atom;

Two adjacent radicals R$_3$ can form, with one another and with the carbon atoms to which they are attached, a substituted or unsubstituted aromatic ring comprising 6 ring members;

The radicals R$_4$, which may be identical or different, are chosen from:
  an optionally substituted C$_1$-C$_{20}$ alkyl radical, optionally interrupted with at least one heteroatom and/or with at least one group comprising at least one heteroatom, wherein the alkyl radical does not comprise any nitro, nitroso, peroxo or diazo function;
  a C$_1$-C$_4$ trimethylsilylalkyl radical;
  an optionally substituted phenyl radical; and
  an optionally substituted benzyl radical;

The radical $R_5$ is chosen from:
- a hydrogen;
- an optionally substituted $C_1$-$C_{20}$ alkyl radical, optionally interrupted with at least one heteroatom and/or with at least one group comprising at least one heteroatom, wherein the alkyl radical does not comprise any nitro, nitroso, peroxo or diazo function;
- an optionally substituted phenyl radical;
- an optionally substituted benzyl radical;
- an alkylcarbonyl radical (R—CO—) wherein R is a $C_1$-$C_4$ alkyl radical;
- an alkylsulphonyl radical (RSO$_2$—) wherein R is a $C_1$-$C_4$ alkyl radical;
- an arylsulphonyl radical (R'SO$_2$—) wherein R' is an optionally substituted phenyl or benzyl radical;
- a (di)(alkyl)aminosulphonyl radical ((R)$_2$N—SO$_2$—) wherein the R radicals are independently chosen from a hydrogen and a $C_1$-$C_4$ alkyl radical; and
- a (di)(alkyl)aminocarbonyl radical ((R)$_2$N—CO—) wherein the R radicals are independently chosen from a hydrogen and a $C_1$-$C_4$ alkyl radical;

$R_5$ can form, with a radical $R_2$ located in the ortho-position with respect to the $NR_5$ group and with the nitrogen atom substituted with $R_5$, a substituted or unsubstituted, saturated or unsaturated heterocycle comprising 5 or 6 ring members;

The radical $R_6$ is chosen from:
- a hydrogen atom;
- an optionally substituted $C_1$-$C_{16}$ alkyl radical, optionally interrupted with at least one heteroatom and/or with at least one group comprising at least one heteroatom, wherein the alkyl radical does not comprise any nitro, nitroso, peroxo or diazo function;
- an amino radical optionally substituted with one or two $C_1$-$C_4$ alkyl radicals, which may be identical or different, optionally carrying at least one hydroxyl or $C_1$-$C_2$ alkoxy group, it being possible for said alkyl radicals to optionally form, with the nitrogen atom to which they are attached, an optionally substituted, saturated or unsaturated or aromatic heterocycle comprising 5 or 6 ring members, optionally comprising at least one other heteroatom which may be identical to or different from nitrogen;
- an alkylcarbonylamino radical (RCO—NR'—) wherein the R radical is a $C_1$-$C_4$ alkyl radical and the R' radical is chosen from a hydrogen and a $C_1$-$C_4$ alkyl radical;
- a ureido radical (N(R)$_2$CO—NR'—) wherein the R radicals, independently of one another, are chosen from a $C_1$-$C_4$ alkyl radical, and R' is chosen from a hydrogen and a $C_1$-$C_4$ alkyl radical;
- an alkylsulphonylamino radical (RSO$_2$—NR'—) wherein the R radical is a $C_1$-$C_4$ alkyl radical and the R' radical is chosen from a hydrogen and a $C_1$-$C_4$ alkyl radical;
- a hydroxycarbonyl radical (HOOC—);
- a $C_1$-$C_4$ alkoxycarbonyl radical (RO—CO—);
- an optionally substituted phenyl radical; and
- an optionally substituted benzyl radical;

p is an integer ranging from 0 to 3; p' is an integer ranging from 0 to 4; when p is less than 3, or p' is less than 4, the unsubstituted carbon atom(s) carries a hydrogen atom;

The bond a links the heteroaromatic radical $W_1$ to the carbon atom of the $CR_6$ group;

Z is a $C_2$-$C_{20}$ alkylene radical comprising at least one quaternized nitrogen atom;

the bond d links the cationic group(s) Z to a nitrogen atom of the heteroaromatic radical $W_1$;

the electroneutrality of the compounds of formula (I) being ensured by at least one cosmetically acceptable anion An or a mixture of cosmetically acceptable anions An, which may or may not be identical;

and the following compounds wherein, $R_1$, $R_2$, m, and An are as defined above, for which R is chosen from a hydrogen atom and a methyl radical:

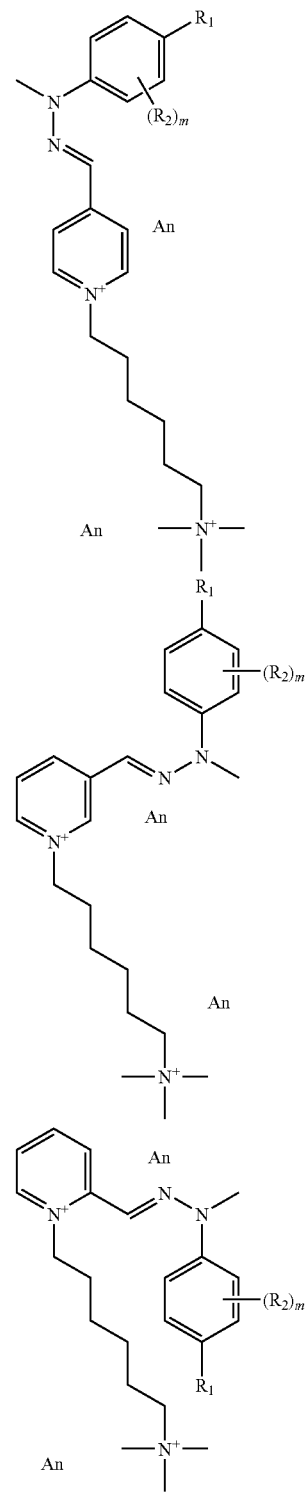

-continued
151
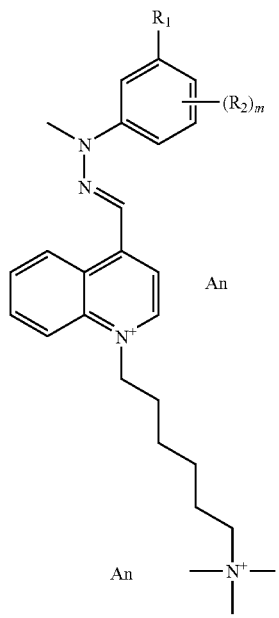
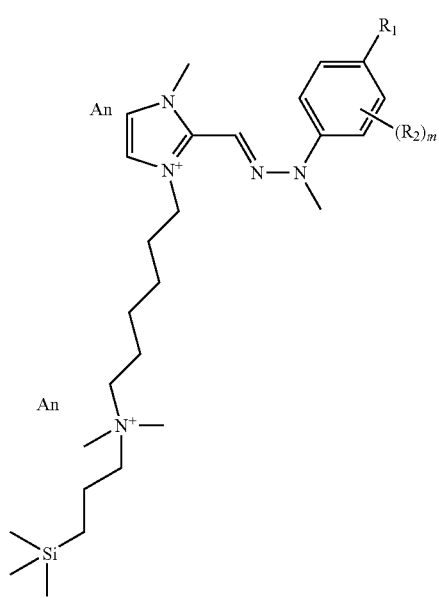
152
-continued
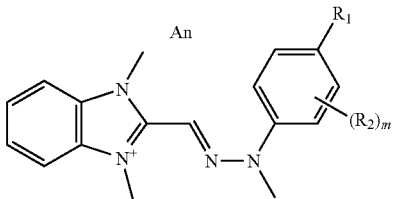
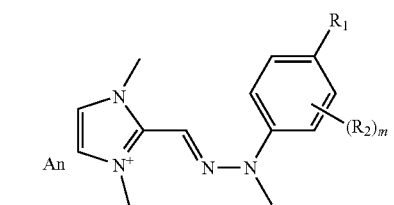
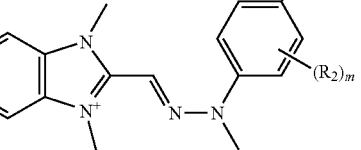
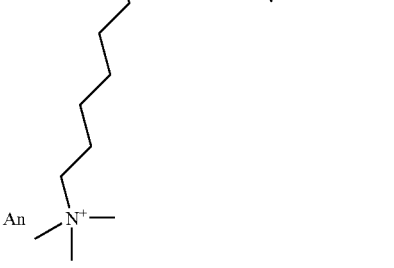

-continued
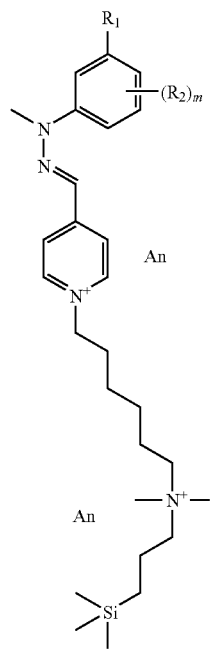
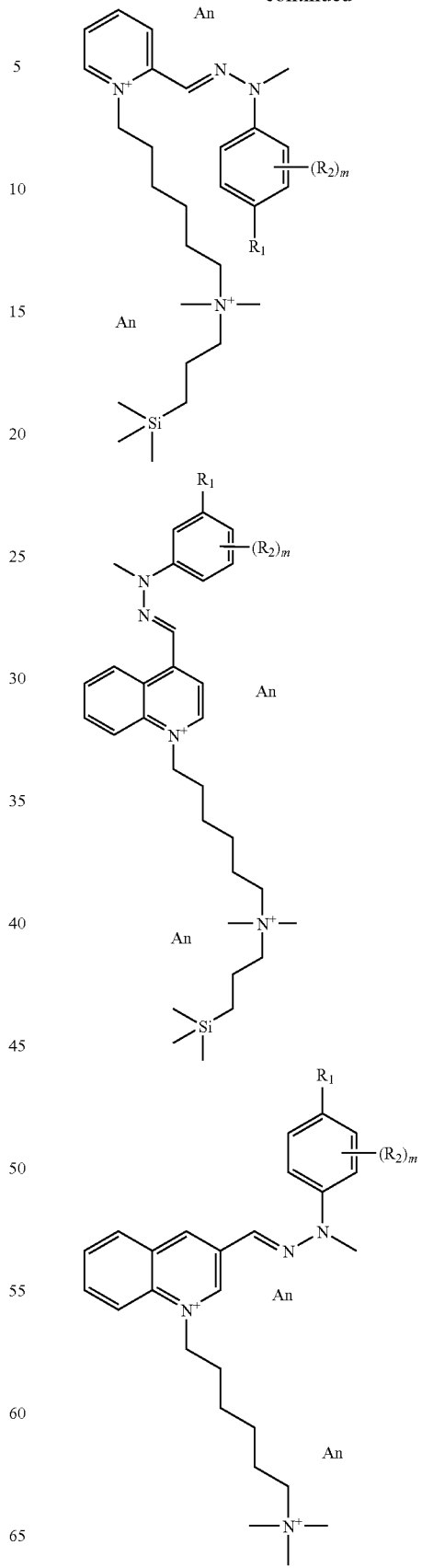

-continued
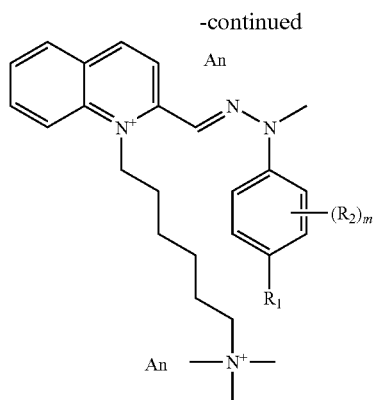
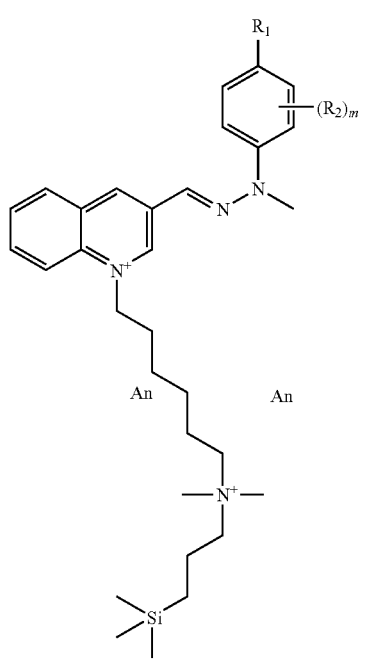
-continued
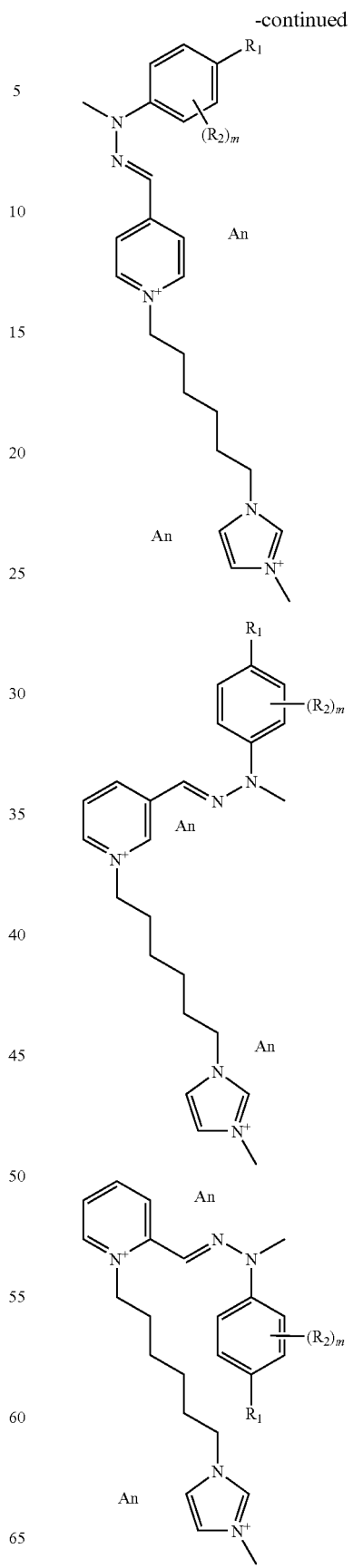
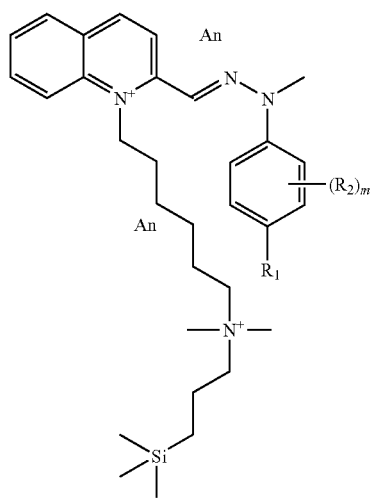

157
-continued
158
-continued
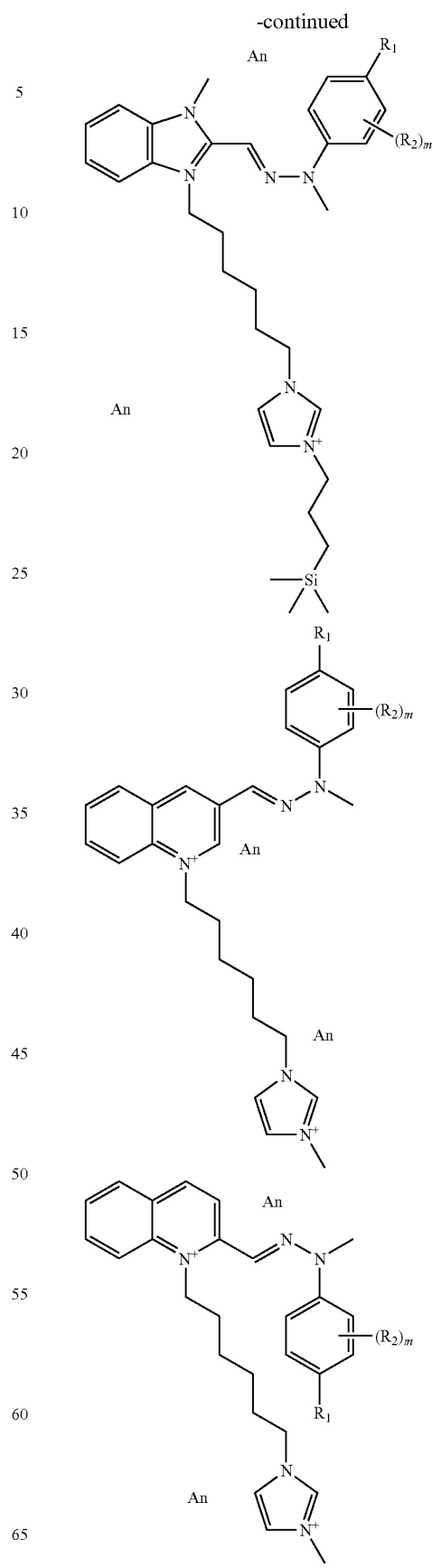

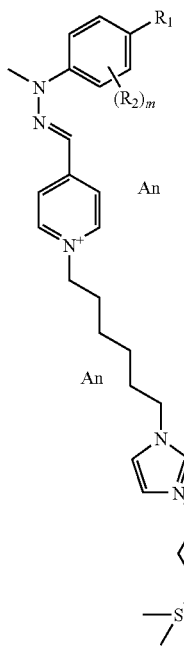
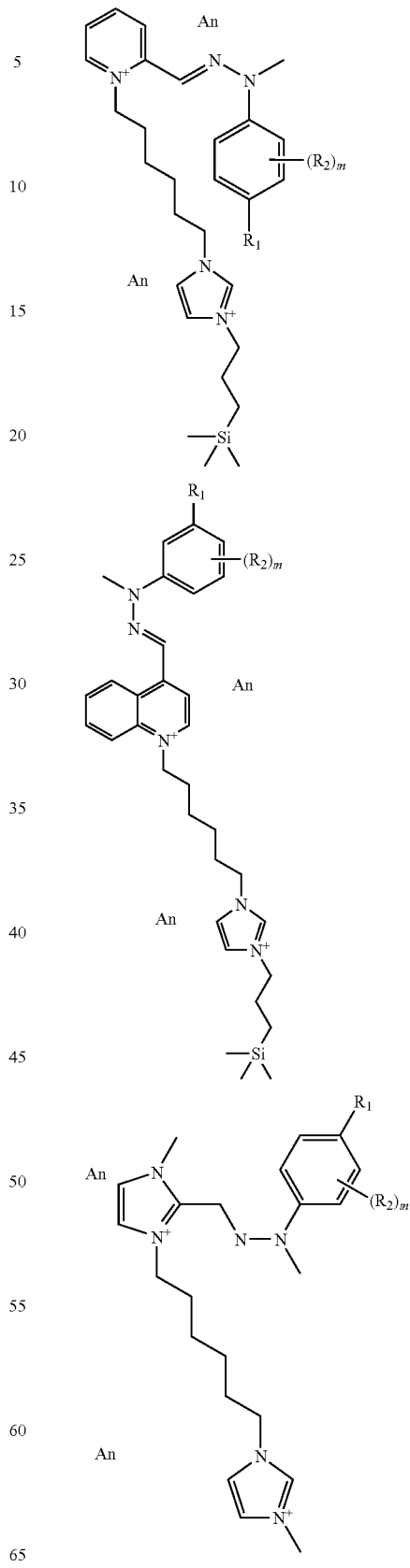

161
-continued
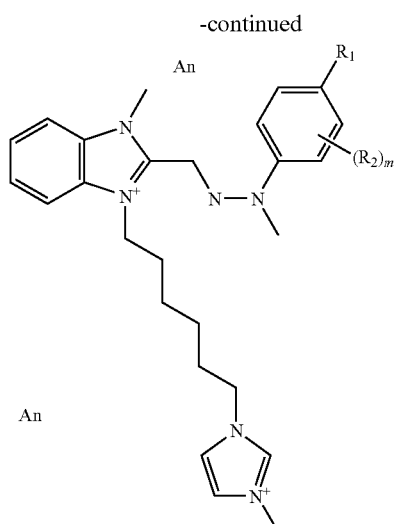
162
-continued
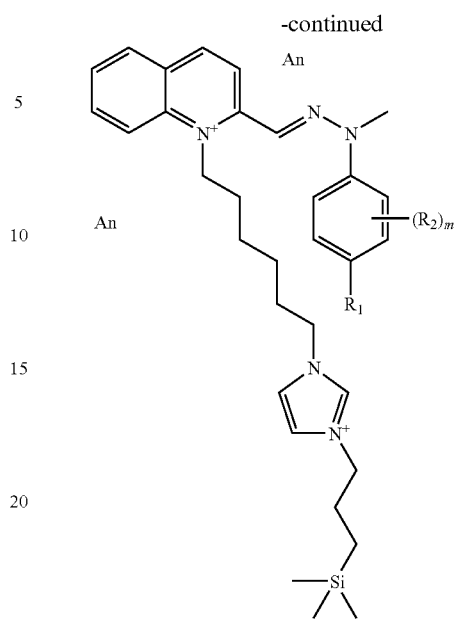
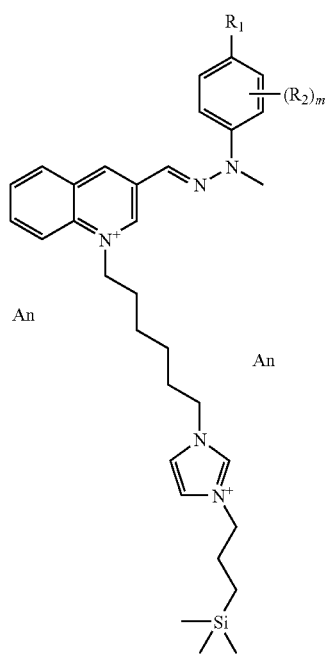
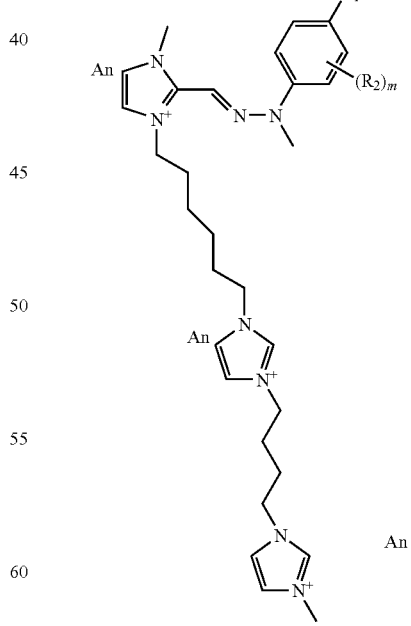

-continued
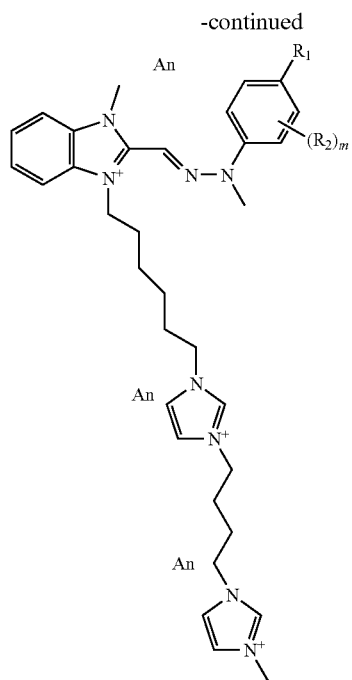
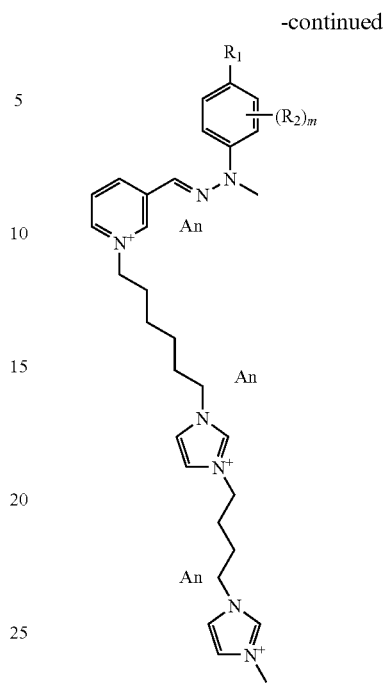
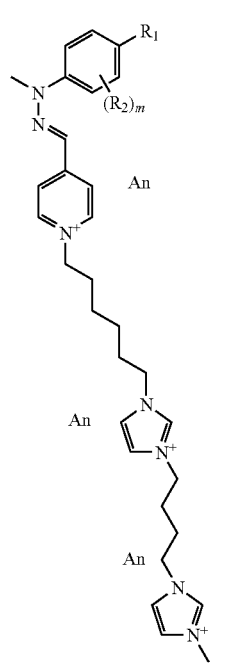
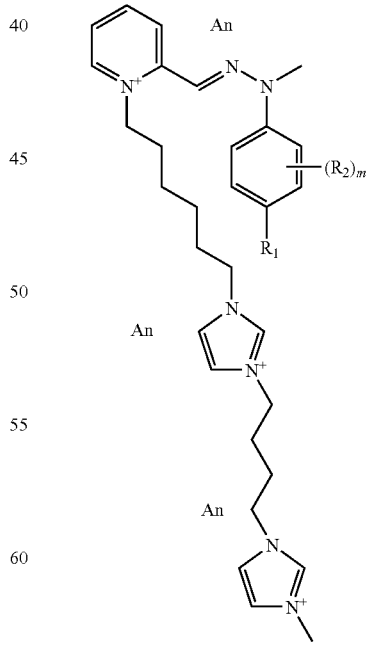

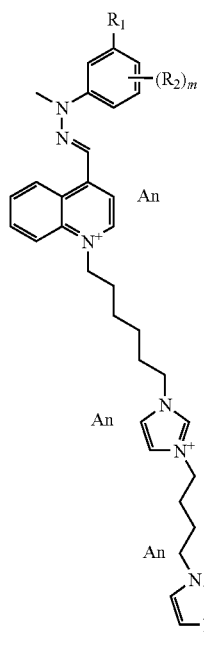
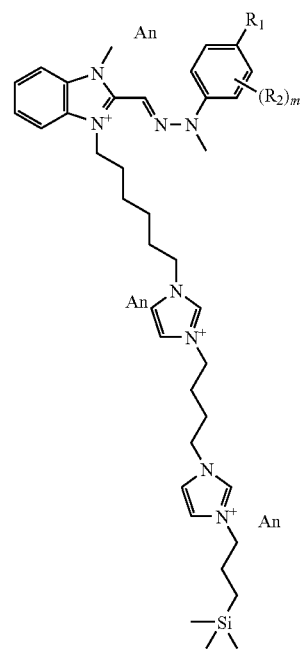
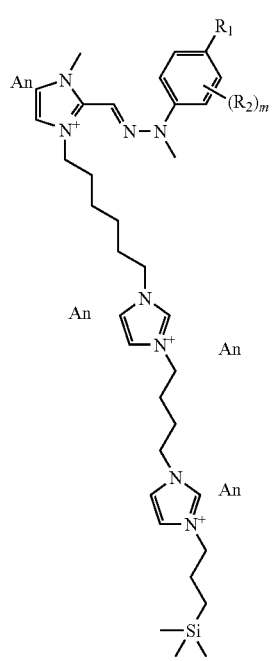
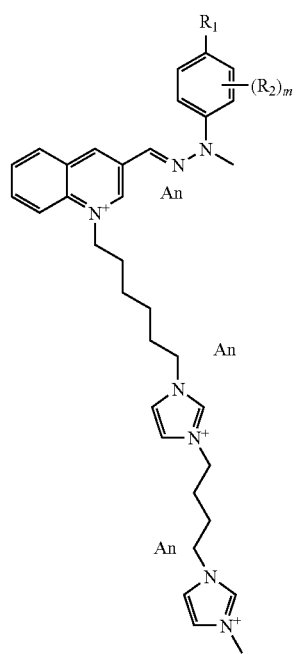

-continued
167
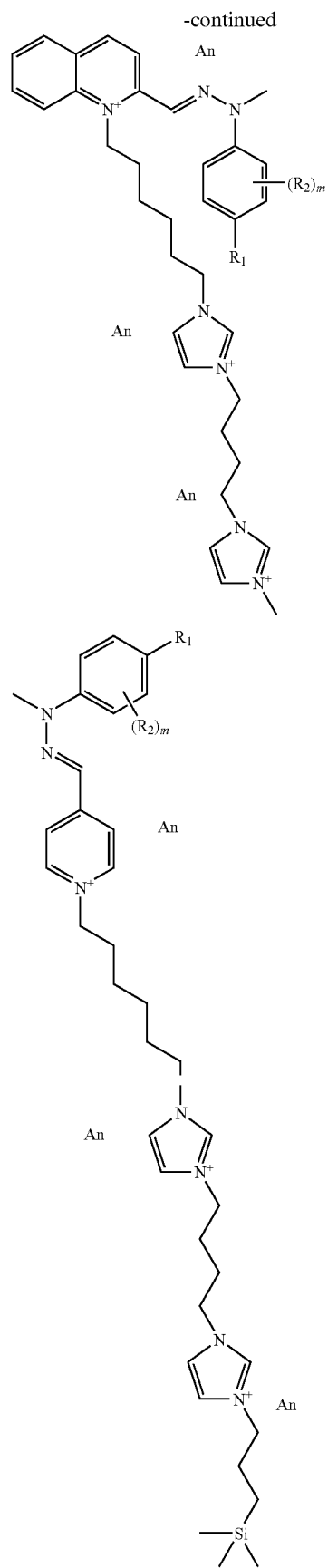
168
-continued
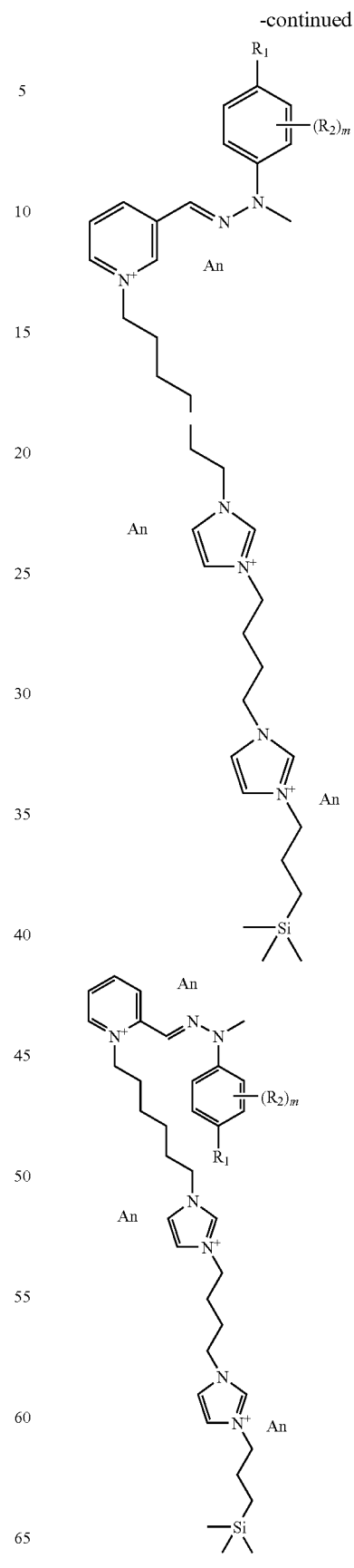

169
-continued
170
-continued
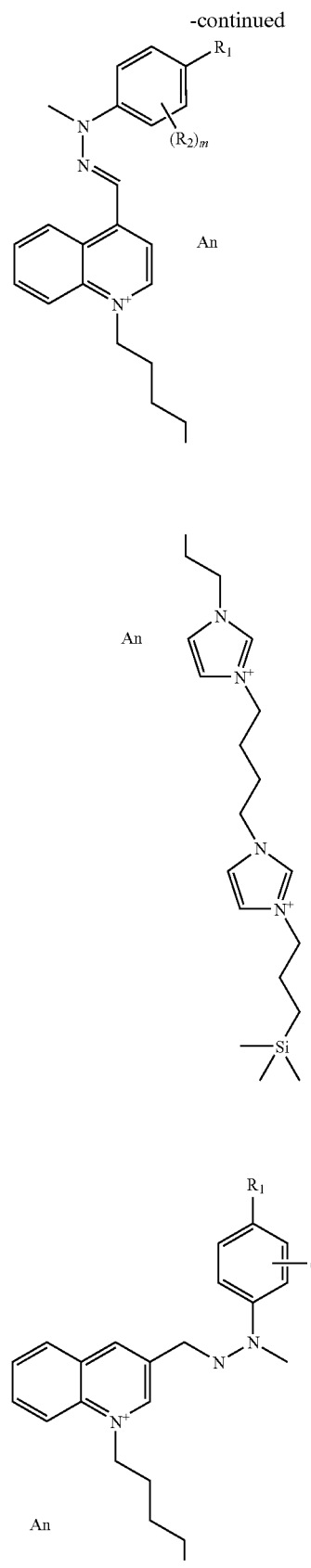
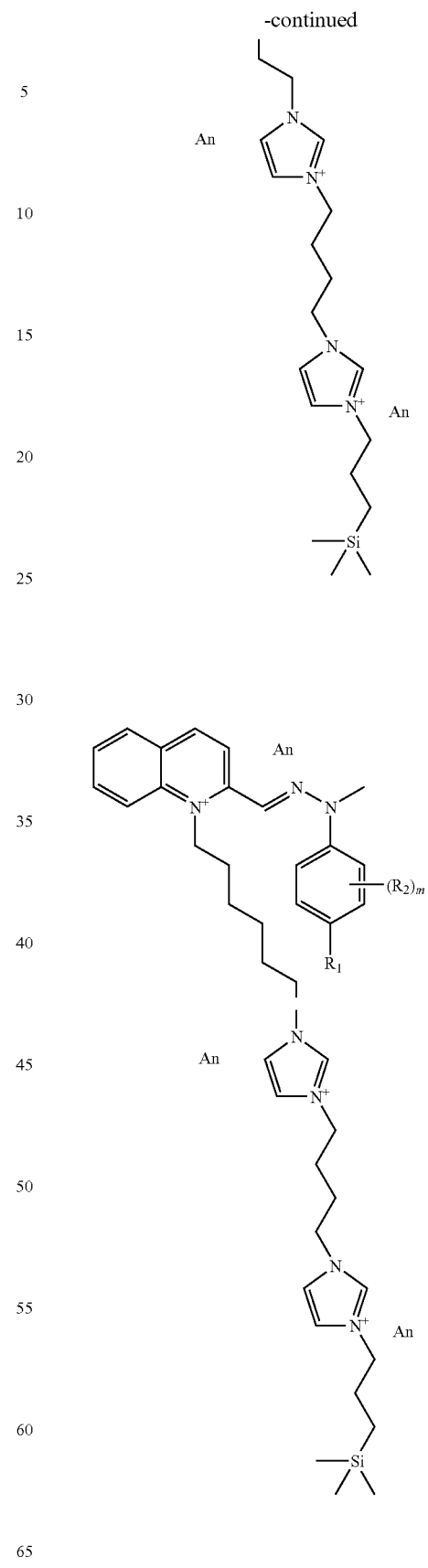

-continued
171
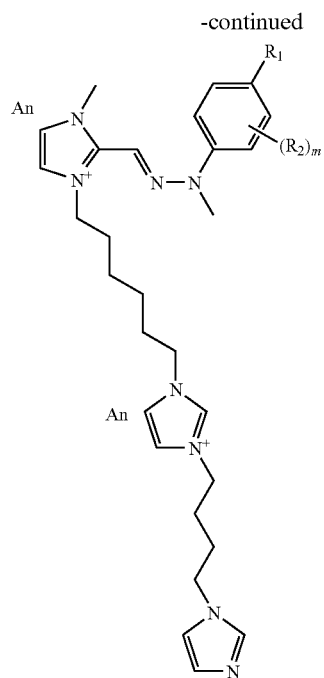
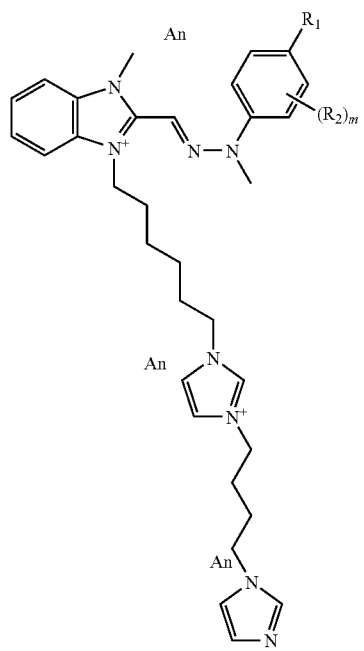
172
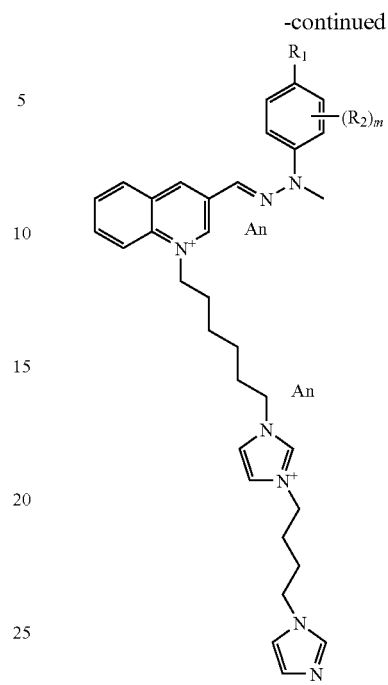
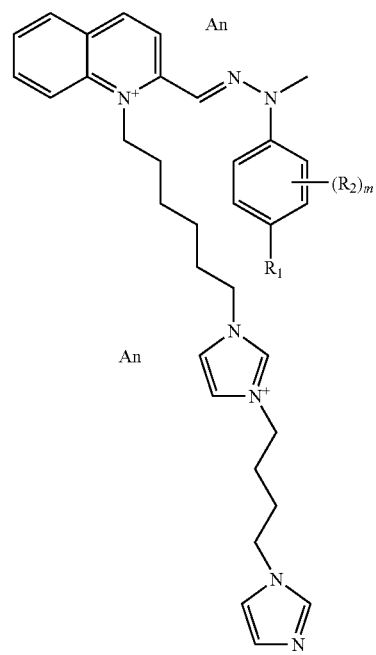

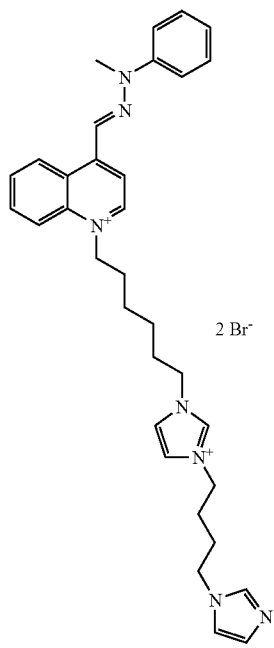

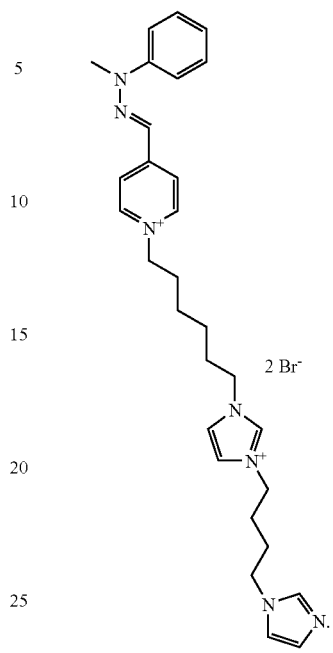

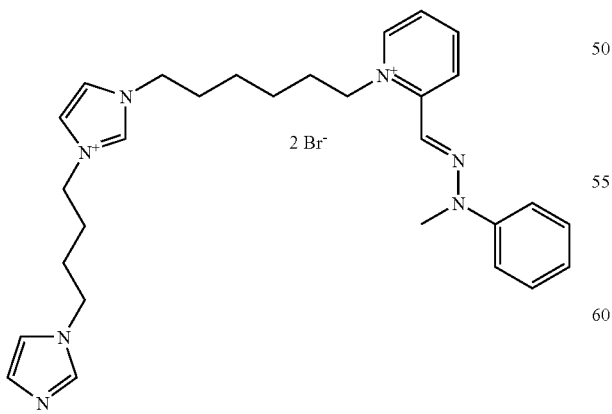

21. A multicompartment device, wherein the device comprises a first compartment comprising a dye composition, wherein the dye composition comprises at least one polycationic hydrazone entity chosen from compounds of formula (I), tautomeric forms thereof, acid-addition salts thereof and solvates thereof:

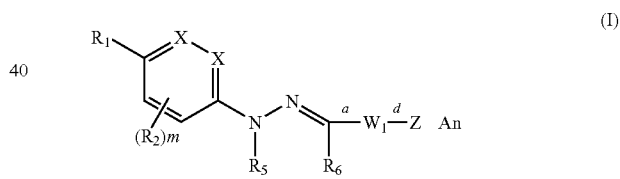

wherein:

$W_1$ is a heteroaromatic radical of following formulae (1) to (8):

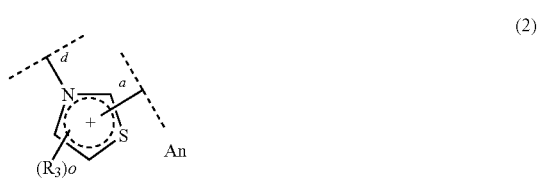

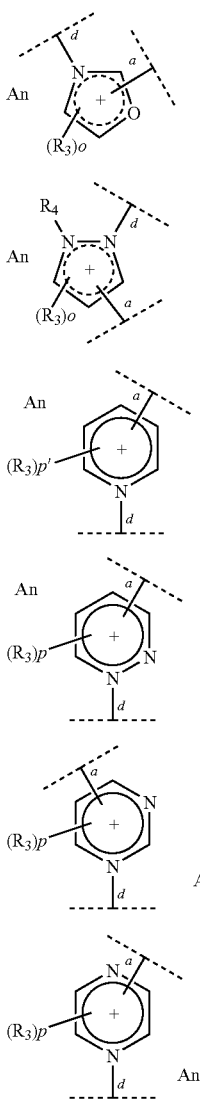

wherein:
the radical $R_1$ is chosen from:
a hydrogen;
an optionally substituted $C_1$-$C_{20}$ alkyl radical, optionally interrupted with at least one heteroatom and/or with at least one group comprising at least one heteroatom, wherein the alkyl radical does not comprise any nitro, nitroso, peroxo or diazo function;
an alkylcarbonyl radical (R—CO—) wherein R is a $C_1$-$C_4$ alkyl radical;
an alkylsulphonyl radical (RSO$_2$—) wherein R is a $C_1$-$C_4$ alkyl radical;
an arylsulphonyl radical (R'SO$_2$—) wherein R' is an optionally substituted phenyl or benzyl radical;
a (di)(alkyl)aminosulphonyl radical ((R)$_2$N—SO$_2$—) wherein the R radicals independently are chosen from a hydrogen and a $C_1$-$C_4$ alkyl radical;
a (di)(alkyl)aminocarbonyl radical ((R)$_2$N—CO—) wherein the R radicals independently are chosen from a hydrogen and a $C_1$-$C_4$ alkyl radical;
a halogen atom;
a hydroxyl group;
a $C_1$-$C_4$ alkoxy group;
a $C_2$-$C_4$ (poly)hydroxyalkoxy group;
a hydroxycarbonyl group;
an alkoxycarbonyl group (RO—CO—) wherein R is a $C_1$-$C_4$ alkyl radical;
an alkylcarbonyloxy radical (RCO—O—) wherein R is a $C_1$-$C_4$ alkyl radical;
an optionally substituted aryloxy group;
an NR$_7$R$_8$ group wherein R$_7$ and R$_8$ are chosen from, independently of one another:
a hydrogen atom;
a $C_1$-$C_4$ alkyl radical, optionally carrying at least one hydroxyl or $C_1$-$C_2$ alkoxy group, it being possible for said alkyl radicals to optionally form, with the nitrogen atom to which they are attached, a saturated or unsaturated, optionally substituted, optionally aromatic heterocycle containing from 5 to 7 ring members, optionally comprising another heteroatom which may be identical to or different from nitrogen;
a phenyl radical; an aminophenyl radical; a 4-N,N-diethylaminophenyl radical; a methoxyphenyl radical;
an alkylcarbonylamino group (RCO—NR'—) wherein the R radical is a $C_1$-$C_4$ alkyl radical and the R' radical is chosen from a hydrogen atom and a $C_1$-$C_4$ alkyl radical;
a ureido group (N(R)$_2$—CO—NR'—) wherein the R and R' radicals, independently of one another, are chosen from a hydrogen atom and $C_1$-$C_4$ alkyl radicals;
an alkylthio group (R—S—) wherein the R group is a $C_1$-$C_4$ alkyl radical;
an alkylsulphonylamino group (RSO$_2$—NR'—) wherein the R' radical is chosen from a hydrogen atom and a $C_1$-$C_4$ alkyl radical, and the R radical is a $C_1$-$C_4$ alkyl radical;
a cyano group; and
a trifluoromethyl group (CF$_3$);
The radicals $R_2$ and $R_3$, which may be identical or different, are chosen from, independently of one another:
a halogen atom;
an optionally substituted $C_1$-$C_{16}$ alkyl radical, optionally interrupted with at least one heteroatom and/or with at least one group comprising at least one heteroatom; wherein the alkyl radical does not comprise any nitro, nitroso, peroxo or diazo functions;
a hydroxyl radical;
a $C_1$-$C_4$ alkoxy radical;
a $C_2$-$C_4$ (poly)hydroxyalkoxy group;
a hydroxycarbonyl radical;
an alkoxycarbonyl radical (RO—CO—) wherein R is a $C_1$-$C_4$ alkyl radical;
an alkylcarbonyloxy radical (RCO—O) wherein R is a $C_1$-$C_4$ alkyl radical;
an optionally substituted aryloxy radical;
an optionally substituted arylamino radical;
an amino radical optionally substituted with one or two $C_1$-$C_4$ alkyl radicals, which may be identical or different, optionally carrying at least one hydroxyl or $C_1$-$C_2$ alkoxy group, it being possible for said alkyl radicals to optionally form, with the nitrogen atom to which they are attached, a saturated or unsaturated, optionally substituted, optionally aromatic heterocycle containing from 5 to 7 ring members, optionally comprising another heteroatom which may be identical to or different from nitrogen;

an alkylcarbonylamino radical (RCO—NR'—) wherein the R radical is a $C_1$-$C_4$ alkyl radical and the R' radical is chosen from a hydrogen and a $C_1$-$C_4$ alkyl radical;

a (di)(alkyl)aminocarbonyl group (($R$)$_2$N—CO—) wherein the R radicals, independently of one another, are chosen from a hydrogen and a $C_1$-$C_4$ alkyl radical;

a ureido radical (N(R)$_2$—CO—NR'—) wherein the R radicals, independently of one another, are chosen from $C_1$-$C_4$ alkyl radicals, and R' is chosen from a hydrogen and a $C_1$-$C_4$ alkyl radical;

a (di)(alkyl)aminosulphonyl radical (($R$)$_2$N—SO$_2$—) wherein the R radical is chosen from a hydrogen atom and a $C_1$-$C_4$ alkyl radical;

an alkylthio radical (R—S—) wherein the R radical is a $C_1$-$C_4$ alkyl radical;

an alkylsulphonylamino radical (RSO$_2$—NR'—) wherein the R radical is a $C_1$-$C_4$ alkyl radical, and the R' radical is chosen from a hydrogen atom and a $C_1$-$C_4$ alkyl radical;

an alkylsulphonyl radical (RSO$_2$—) wherein the R radical is a $C_1$-$C_4$ alkyl radical;

a cyano radical (—CN); and a trifluoromethyl radical (CF$_3$);

Two adjacent radicals $R_2$ can form, with one another and with the carbon atoms to which they are attached, a substituted or unsubstituted, aromatic or nonaromatic (hetero)cyclic radical comprising 5 or 6 ring members;

One of the radicals $R_7$ or $R_8$ can form, with the nitrogen atom to which it is attached and with a radical $R_2$ located in the ortho-position with respect to the NR$_7$R$_8$ group, a substituted or unsubstituted, saturated or unsaturated heterocycle comprising 5 or 6 ring members;

The radicals $R_7$ and $R_8$ can form, with the nitrogen atom to which they are attached and each with a radical $R_2$ located in the ortho-position with respect to the NR$_7$R$_8$ group, a substituted or unsubstituted, saturated or unsaturated heterocycle comprising 5 or 6 ring members;

m is an integer ranging from 0 to 4; when m is less than 4, the unsubstituted carbon atom(s) carries a hydrogen atom;

X, independently of one another, is N or CR$_2$;

o is an integer ranging from 0 to 2; when o is less than 2, the unsubstituted carbon atom(s) carries a hydrogen atom;

Two adjacent radicals $R_3$ can form, with one another and with the carbon atoms to which they are attached, a substituted or unsubstituted aromatic ring comprising 6 ring members;

The radicals $R_4$, which may be identical or different, are chosen from:
an optionally substituted $C_1$-$C_{20}$ alkyl radical, optionally interrupted with at least one heteroatom and/or with at least one group comprising at least one heteroatom, wherein the alkyl radical does not comprise any nitro, nitroso, peroxo or diazo function;
a $C_1$-$C_4$ trimethylsilylalkyl radical;
an optionally substituted phenyl radical; and
an optionally substituted benzyl radical;

The radical $R_5$ is chosen from:
a hydrogen;
an optionally substituted $C_1$-$C_{20}$ alkyl radical, optionally interrupted with at least one heteroatom and/or with at least one group comprising at least one heteroatom, wherein the alkyl radical does not comprise any nitro, nitroso, peroxo or diazo function;
an optionally substituted phenyl radical;
an optionally substituted benzyl radical;
an alkylcarbonyl radical (R—CO—) wherein R is a $C_1$-$C_4$ alkyl radical;
an alkylsulphonyl radical (RSO$_2$—) wherein R is a $C_1$-$C_4$ alkyl radical;
an arylsulphonyl radical (R'SO$_2$—) wherein R' is an optionally substituted phenyl or benzyl radical;
a (di)(alkyl)aminosulphonyl radical (($R$)$_2$N—SO$_2$—) wherein the R radicals are independently chosen from a hydrogen and a $C_1$-$C_4$ alkyl radical; and
a (di)(alkyl)aminocarbonyl radical (($R$)$_2$N—CO—) wherein the R radicals are independently chosen from a hydrogen and a $C_1$-$C_4$ alkyl radical;

$R_5$ can form, with a radical $R_2$ located in the ortho-position with respect to the NR$_5$ group and with the nitrogen atom substituted with $R_5$, a substituted or unsubstituted, saturated or unsaturated heterocycle comprising 5 or 6 ring members;

The radical $R_6$ is chosen from:
a hydrogen atom;
an optionally substituted $C_1$-$C_{16}$ alkyl radical, optionally interrupted with at least one heteroatom and/or with at least one group comprising at least one heteroatom, wherein the alkyl radical does not comprise any nitro, nitroso, peroxo or diazo function;
an amino radical optionally substituted with one or two $C_1$-$C_4$ alkyl radicals, which may be identical or different, optionally carrying at least one hydroxyl or $C_1$-$C_2$ alkoxy group, it being possible for said alkyl radicals to optionally form, with the nitrogen atom to which they are attached, an optionally substituted, saturated or unsaturated or aromatic heterocycle comprising 5 or 6 ring members, optionally comprising at least one other heteroatom which may be identical to or different from nitrogen;
an alkylcarbonylamino radical (RCO—NR'—) wherein the R radical is a $C_1$-$C_4$ alkyl radical and the R' radical is chosen from a hydrogen and a $C_1$-$C_4$ alkyl radical;
a ureido radical (N(R)$_2$CO—NR'—) wherein the R radicals, independently of one another, are chosen from a $C_1$-$C_4$ alkyl radical, and R' is chosen from a hydrogen and a $C_1$-$C_4$ alkyl radical;
an alkylsulphonylamino radical (RSO$_2$—NR'—) wherein the R radical is a $C_1$-$C_4$ alkyl radical and the R' radical is chosen from a hydrogen and a $C_1$-$C_4$ alkyl radical;
a hydroxycarbonyl radical (HOOC—);
a $C_1$-$C_4$ alkoxycarbonyl radical (RO—CO—);
an optionally substituted phenyl radical; and
an optionally substituted benzyl radical;

p is an integer ranging from 0 to 3; p' is an integer ranging from 0 to 4; when p is less than 3, or p' is less than 4, the unsubstituted carbon atom(s) carries a hydrogen atom;

The bond a links the heteroaromatic radical $W_1$ to the carbon atom of the CR$_6$ group;

Z is a $C_2$-$C_{20}$ alkylene radical comprising at least one quaternized nitrogen atom;

the bond d links the cationic group(s) Z to a nitrogen atom of the heteroaromatic radical $W_1$;

the electroneutrality of the compounds of formula (I) being ensured by at least one cosmetically acceptable anion An or a mixture of cosmetically acceptable anions An, which may or may not be identical;

and the following compounds wherein, $R_1$, $R_2$, m, and An are as defined above, for which R is chosen from a hydrogen atom and a methyl radical:

179
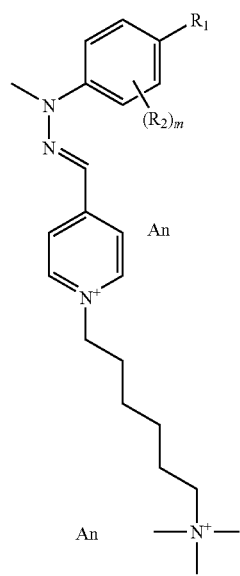
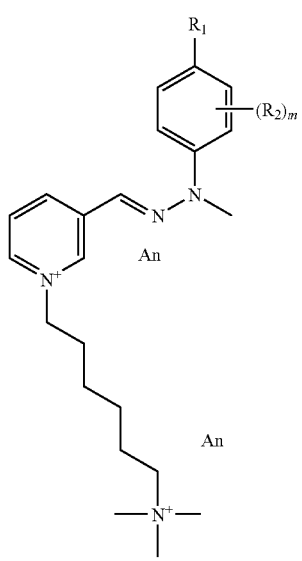
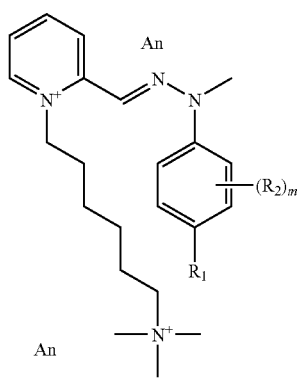
180
-continued
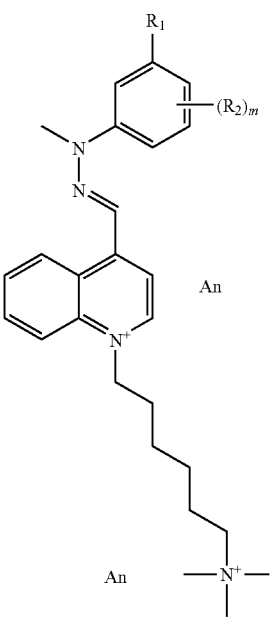
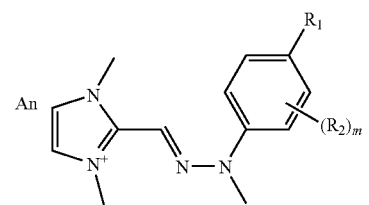
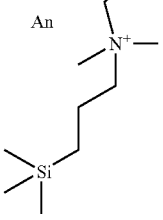

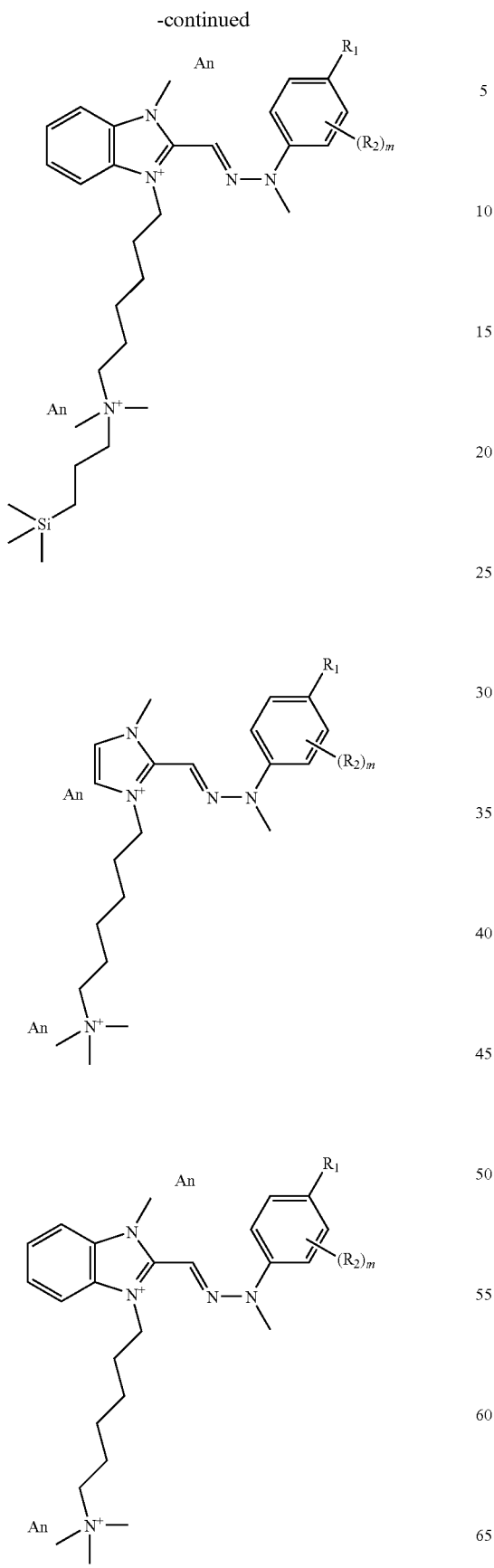
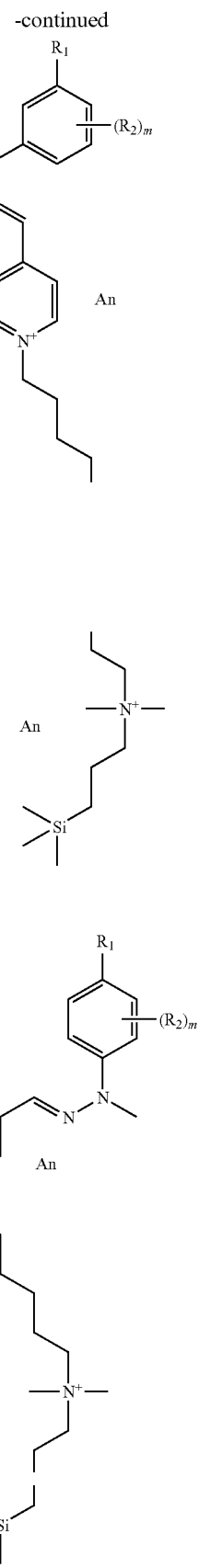

183
-continued
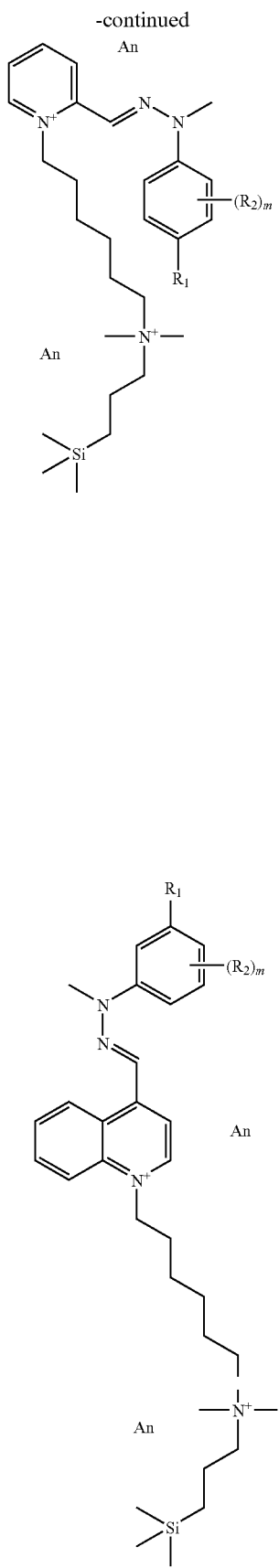
184
-continued
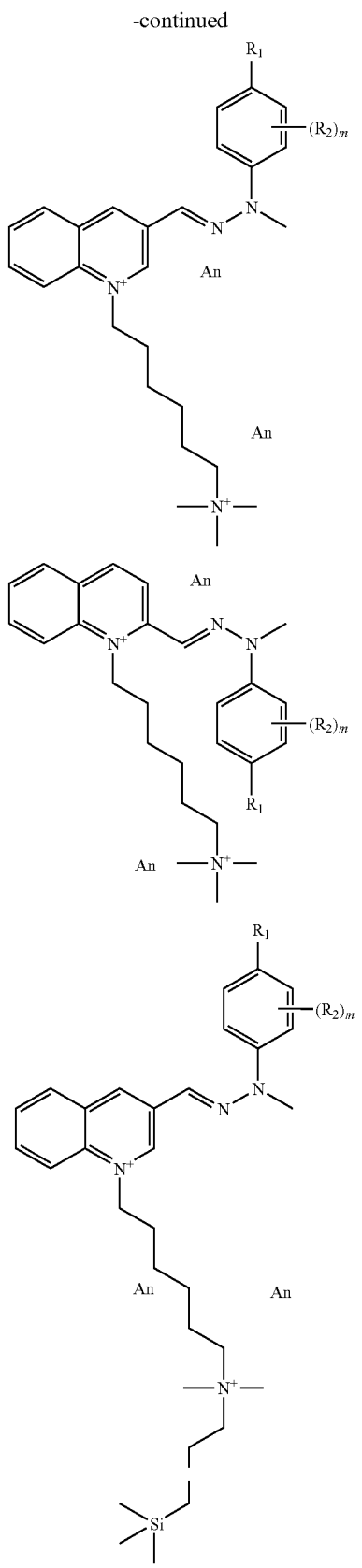

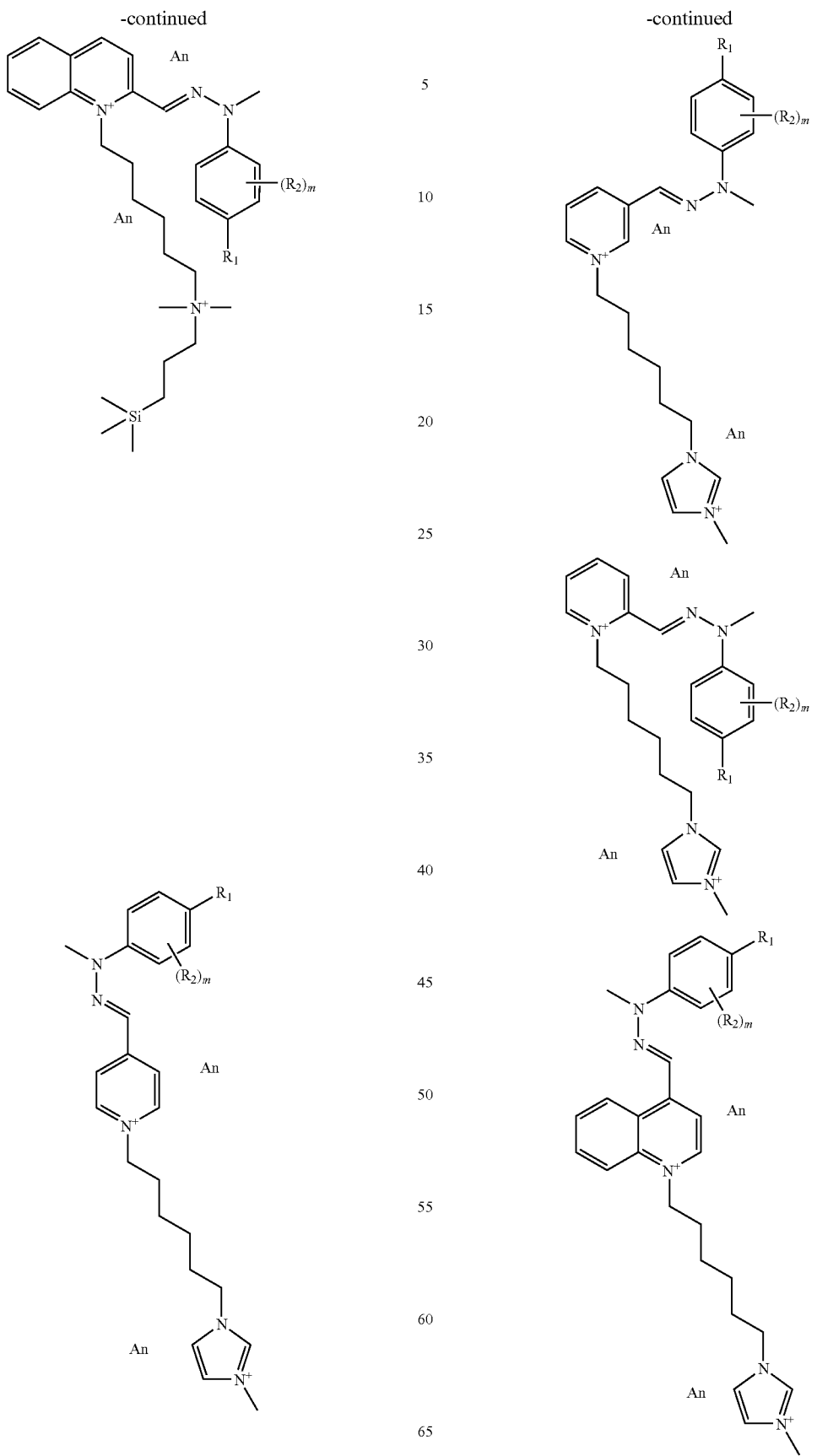

187
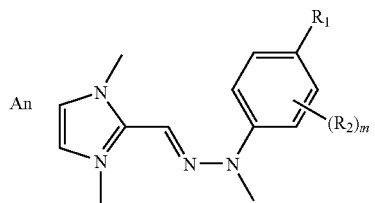
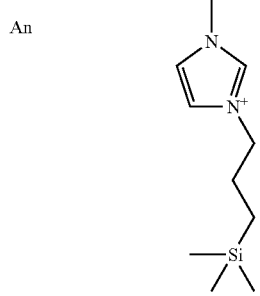
188
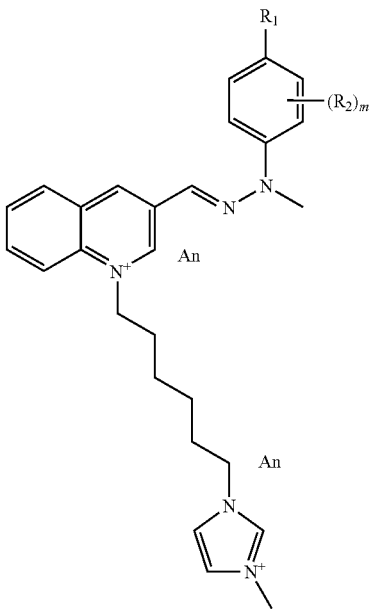
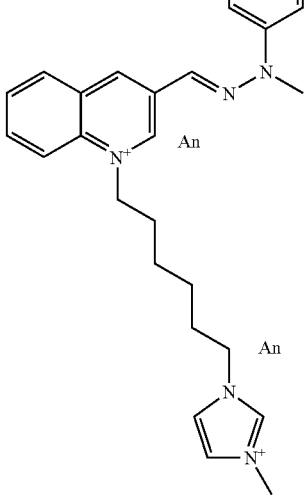
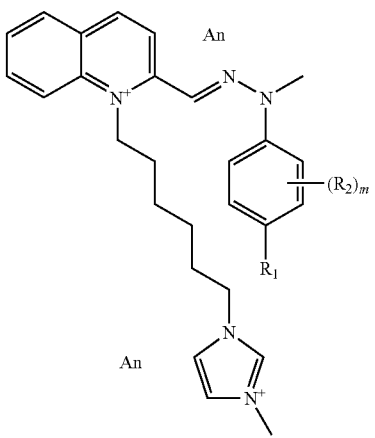

-continued
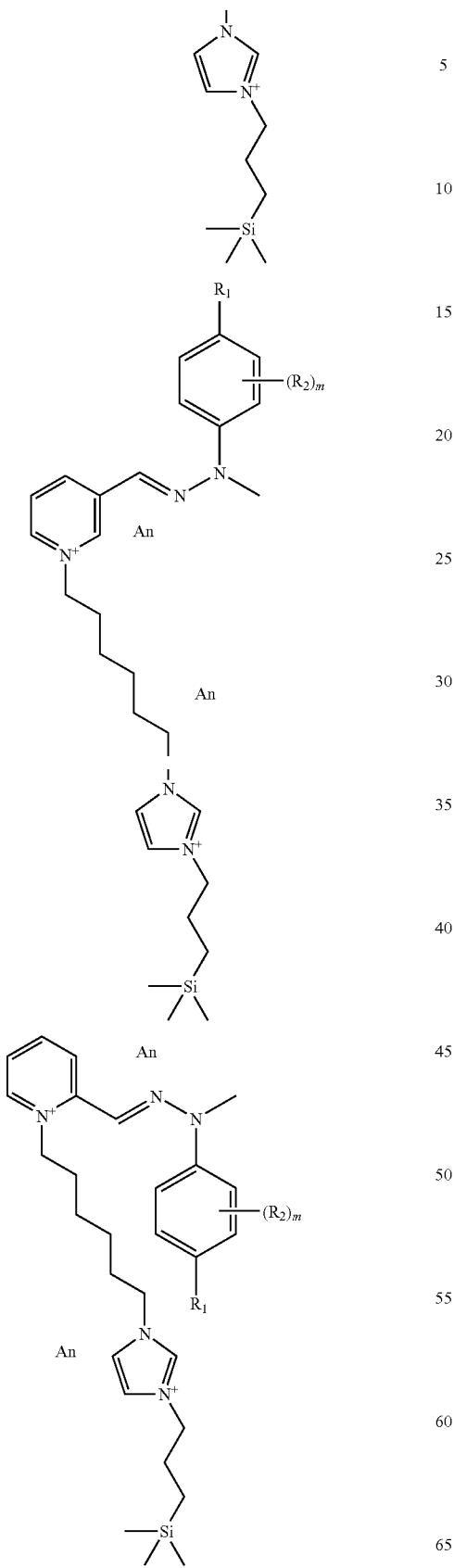
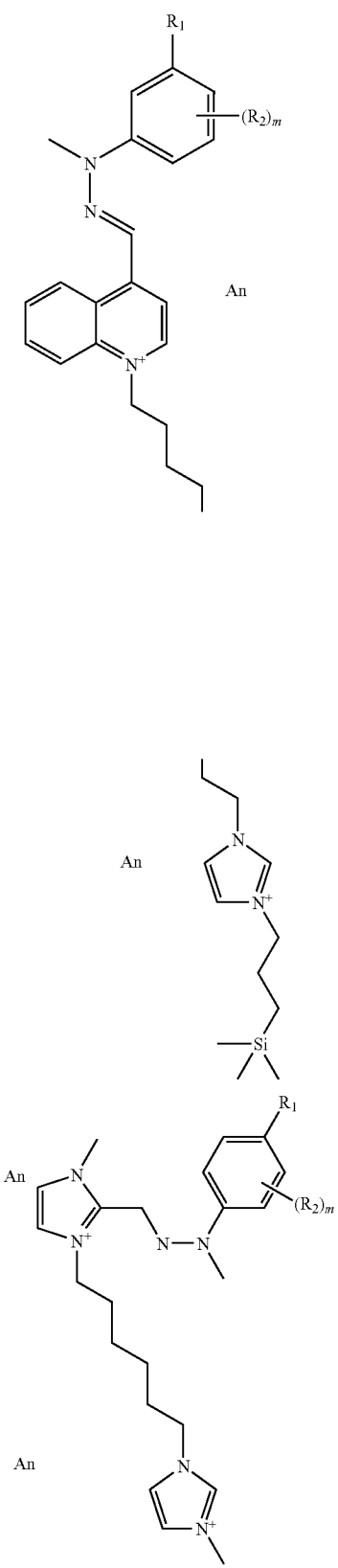

-continued
191
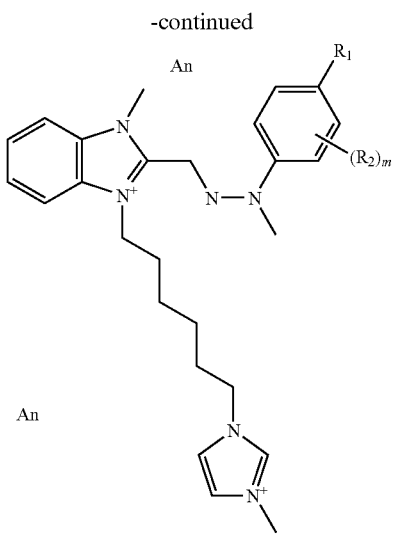
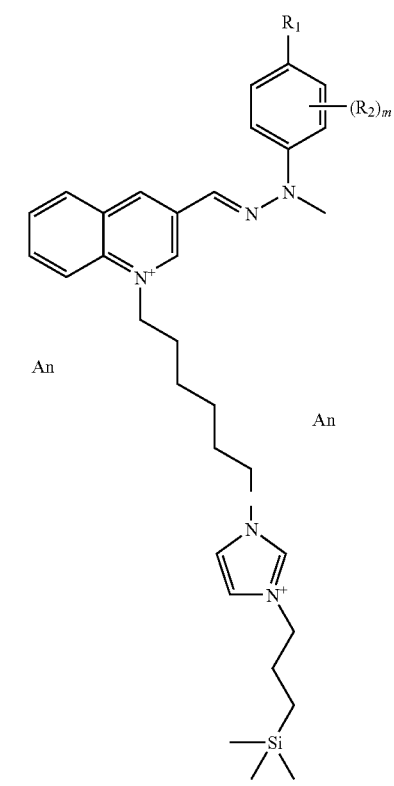
192
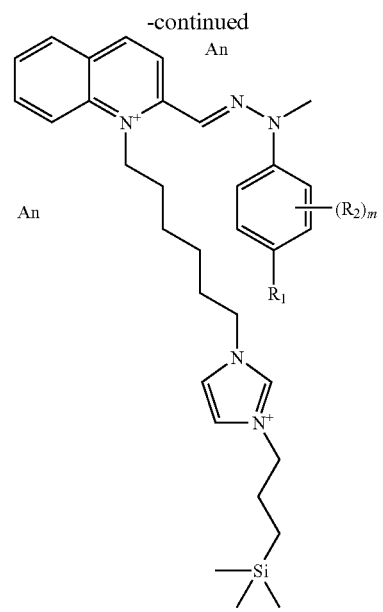
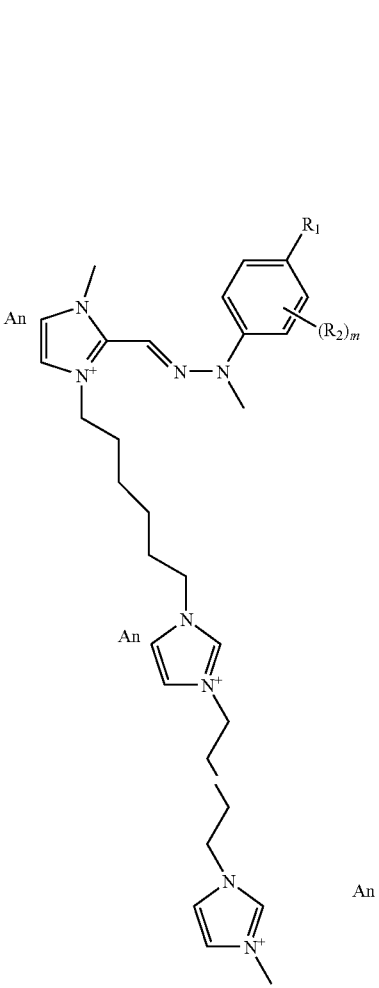

193
-continued
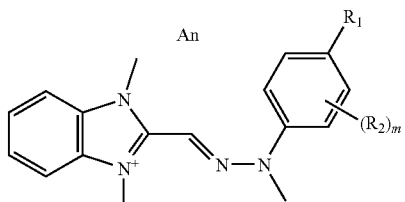
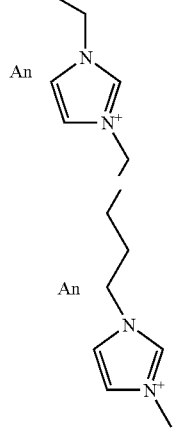
194
-continued
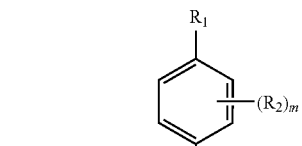
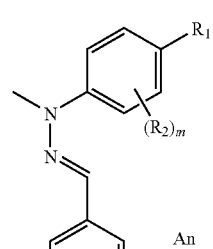

195
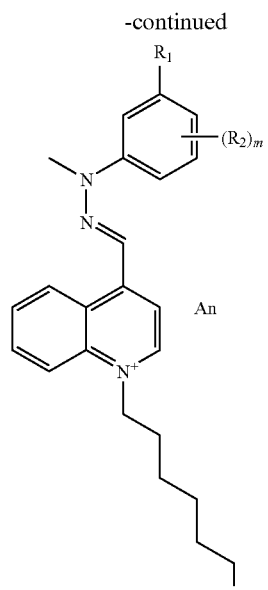
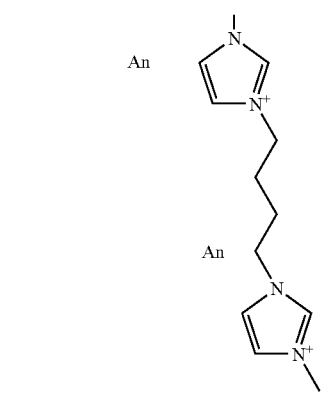
196
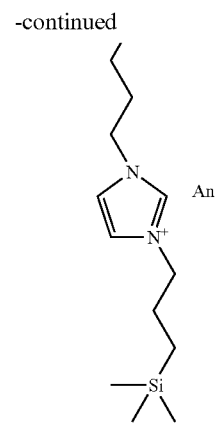
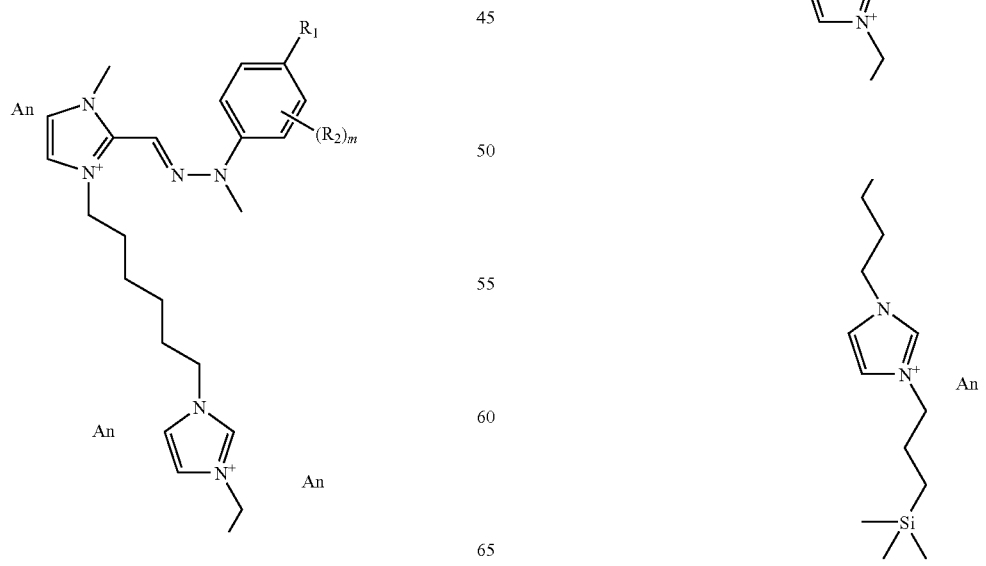
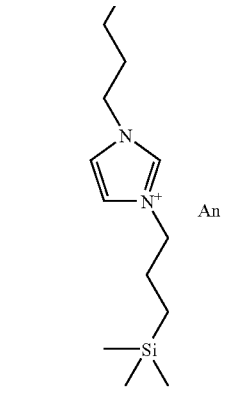

-continued
197
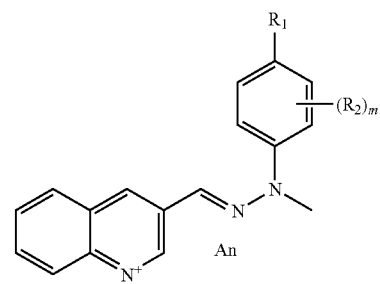
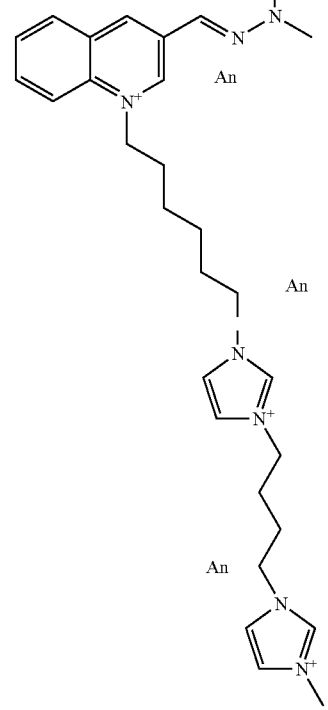
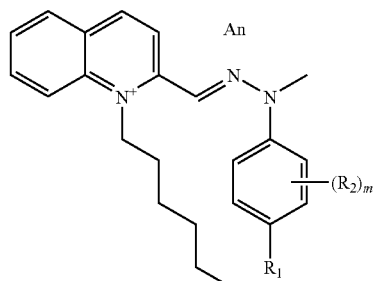
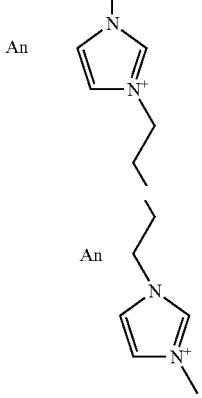
198
-continued
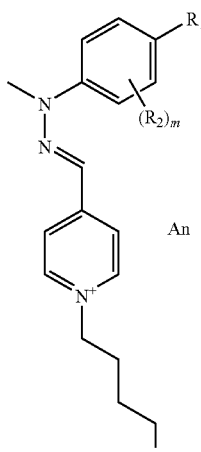
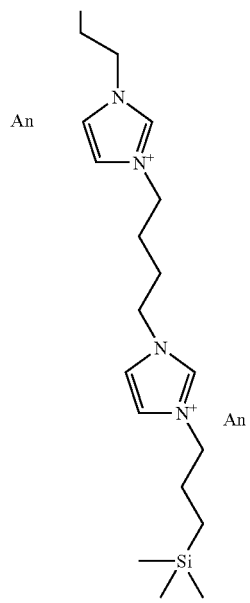
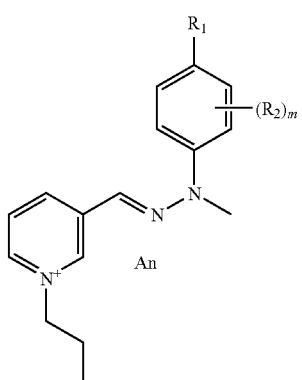

-continued
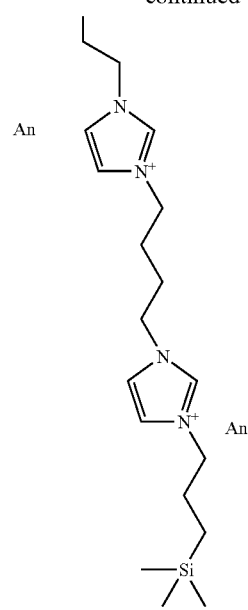
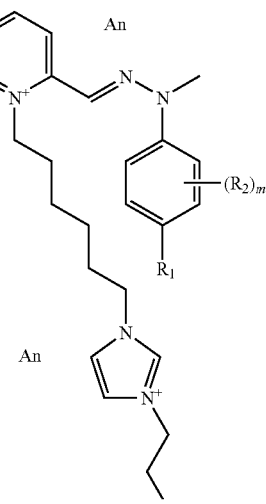
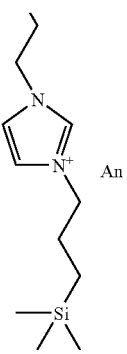
-continued
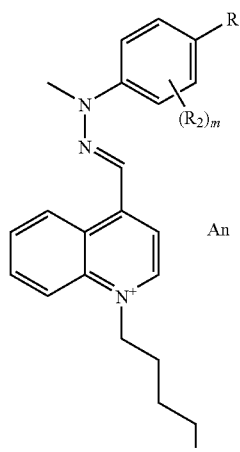
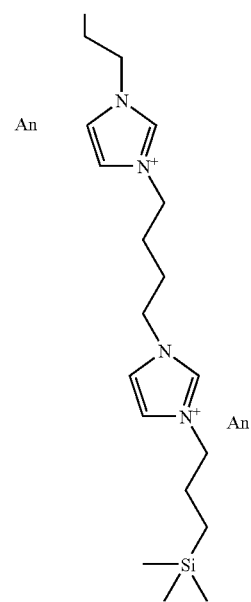
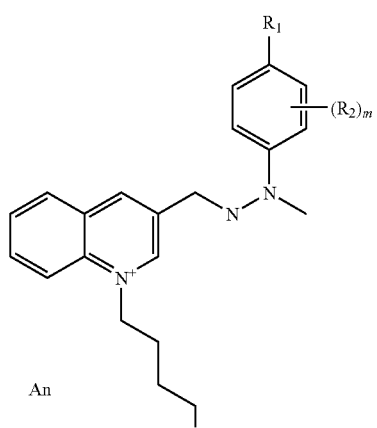

201
-continued
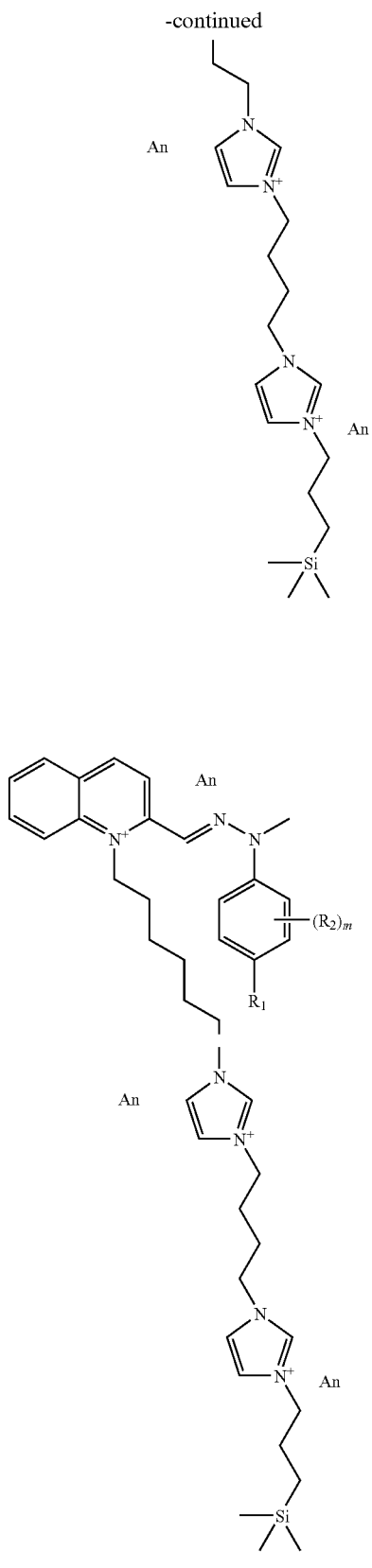
202
-continued
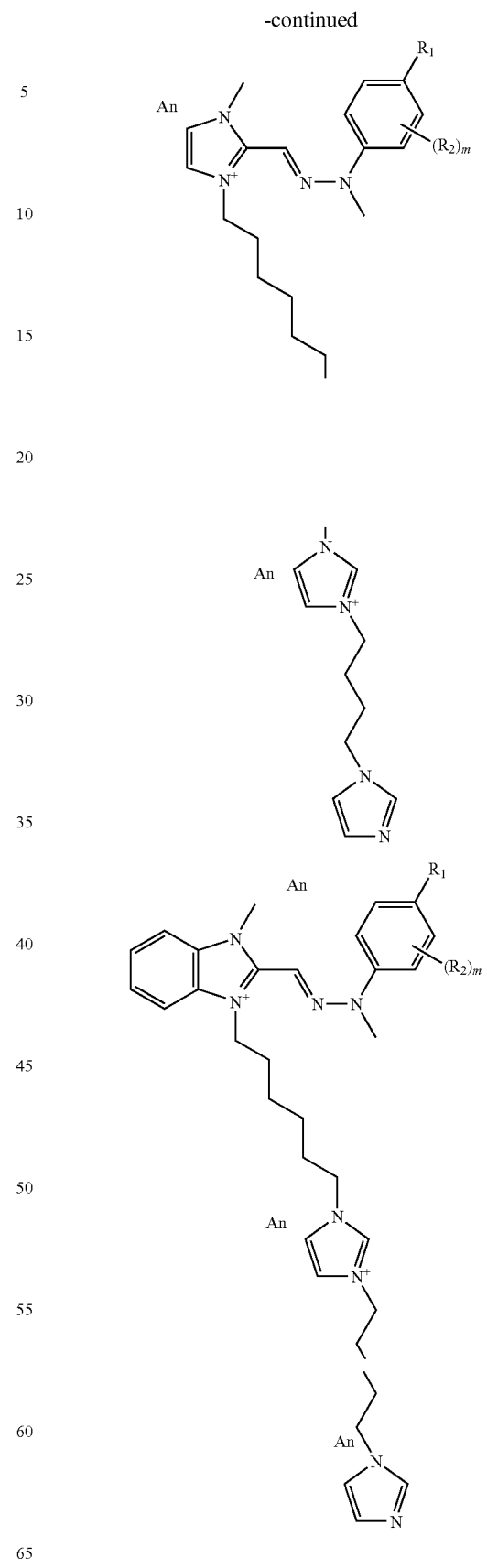

203
-continued
204
-continued
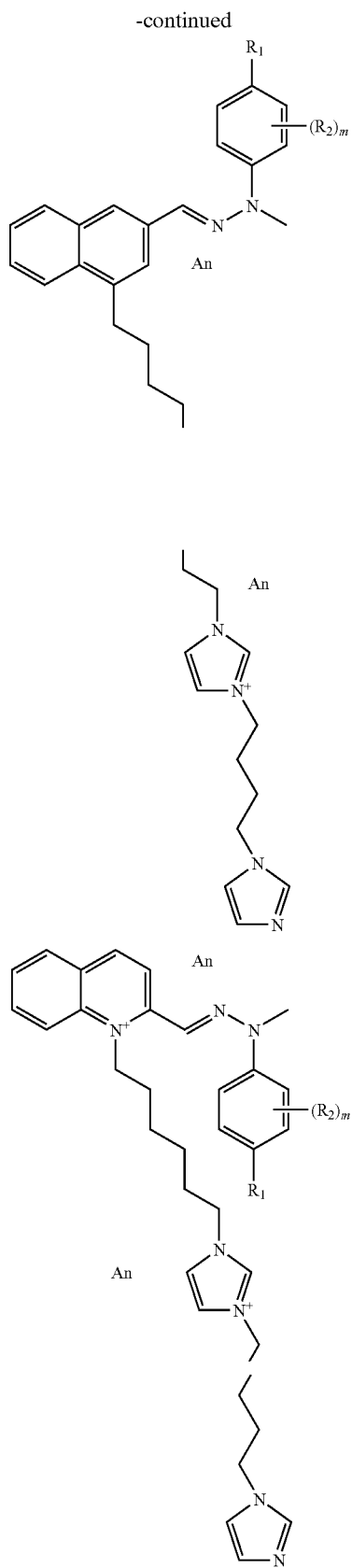
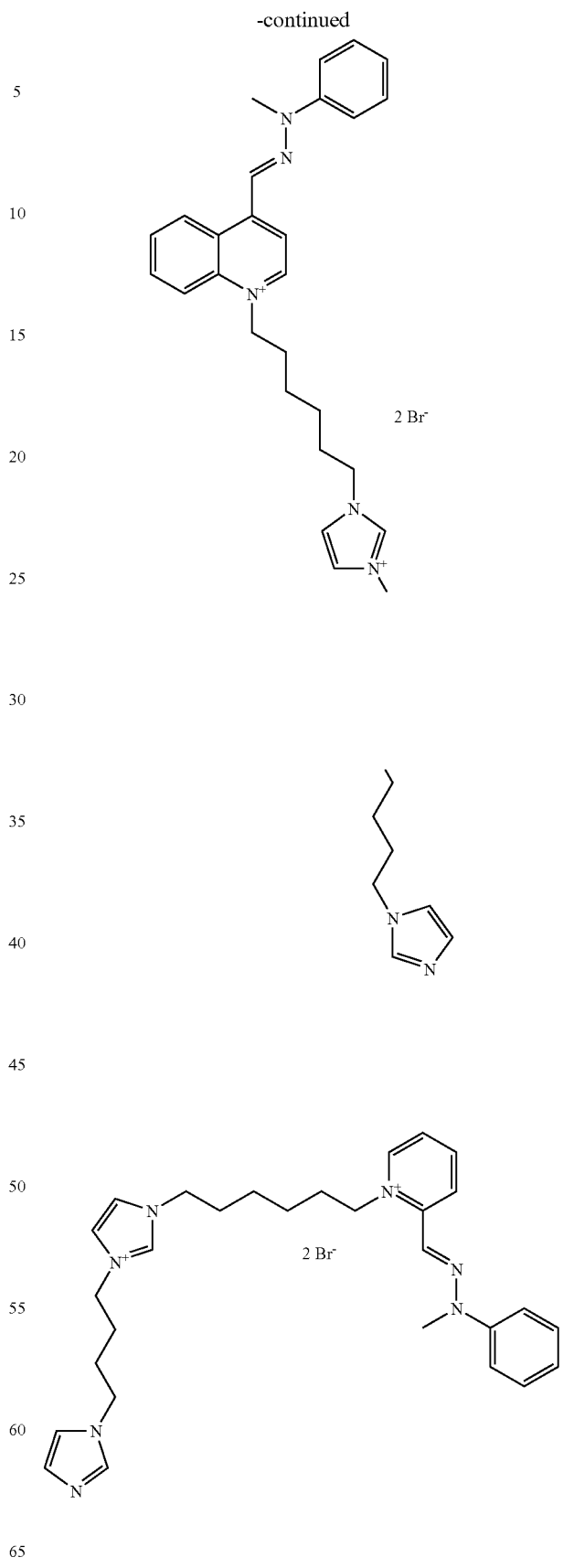

-continued
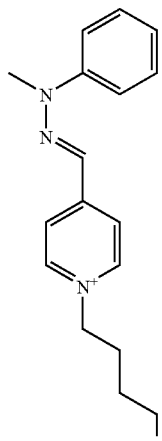
-continued
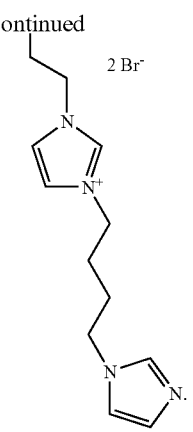
and
a second compartment comprising a composition comprising at least one oxidizing agent.
* * * * *

UNITED STATES PATENT AND TRADEMARK OFFICE
CERTIFICATE OF CORRECTION

PATENT NO.         : 7,569,079 B2                                    Page 1 of 1
APPLICATION NO.    : 12/081288
DATED              : August 4, 2009
INVENTOR(S)        : Hervé David and Nadége Murguet It is certified that error appears in the above-identified patent and that said Letters Patent is hereby corrected as shown below:

On the Title Page, item 57 in the Abstract, line 11, delete "1" before --The--

Signed and Sealed this

Twenty-seventh Day of October, 2009

David J. Kappos
*Director of the United States Patent and Trademark Office*